(12) United States Patent
Loebrich

(10) Patent No.: US 10,913,795 B2
(45) Date of Patent: Feb. 9, 2021

(54) COMPOSITIONS AND METHODS FOR ANTIBODY PRODUCTION

(71) Applicant: ImmunoGen, Inc., Waltham, MA (US)

(72) Inventor: Sven Loebrich, Waltham, MA (US)

(73) Assignee: ImmunoGen, Inc., Waltham, MA (US)

( * ) Notice: Subject to any disclaimer, the term of this patent is extended or adjusted under 35 U.S.C. 154(b) by 0 days.

(21) Appl. No.: 15/981,297

(22) Filed: May 16, 2018

(65) Prior Publication Data

US 2019/0119374 A1 Apr. 25, 2019

Related U.S. Application Data

(60) Provisional application No. 62/507,528, filed on May 17, 2017.

(51) Int. Cl.
C07K 16/00 (2006.01)
C07K 16/28 (2006.01)
C07K 16/30 (2006.01)

(52) U.S. Cl.
CPC ............. C07K 16/28 (2013.01); C07K 16/00 (2013.01); C07K 2317/14 (2013.01); C07K 2317/24 (2013.01); C07K 2317/94 (2013.01)

(58) Field of Classification Search
CPC .... C07K 16/28; C07K 16/00; C07K 2317/24; C07K 2317/94; C07K 2317/14; C07K 16/3007; C07K 16/3092; C07K 16/2863; C07K 16/2896; C07K 1/1133; C12P 21/00; C12N 2500/10; C12N 2500/22; C12N 2500/44; C12N 2500/20
See application file for complete search history.

(56) References Cited

U.S. PATENT DOCUMENTS

| 5,385,842 | A | 1/1995 | Weimer et al. |
| 6,916,909 | B1 | 7/2005 | Nicolas et al. |
| 8,574,869 | B2 | 11/2013 | Kao et al. |
| 2007/0238153 | A1 | 10/2007 | Squires |
| 2009/0053786 | A1* | 2/2009 | Kao ................. A61K 39/39591 435/184 |
| 2017/0002393 | A1 | 1/2017 | Singh et al. |

FOREIGN PATENT DOCUMENTS

| WO | WO-2015085003 A1 * | 6/2015 |
| WO | 2015085003 A1 | 6/2016 |

OTHER PUBLICATIONS

Lloyd et al. Protein Engineering, Design & Selection 22:159-168 (Year: 2009).*
Edwards et al., J Mol Biol. 334(1): 103-118 (Year: 2003).*
Rudikoff et al., PNAS 79: 1979-1983 (Year: 1982).*
International Search Report and the Written Opinion for PCT/US2014/068440, dated Apr. 15, 2015.
Bader, M.W., et al., "Disulfide Bonds are Generated by Quinone Reduction," The Journal of Biological Chemistry, vol. 275, No. 34, pp. 26082-26088, Aug. 25, 2000.

* cited by examiner

Primary Examiner — Phuong Huynh
(74) Attorney, Agent, or Firm — Nixon & Vanderhye, PC

(57) ABSTRACT

Compositions and methods for minimizing antibody disulfide bond reduction are described. In one aspect, a composition is provided for culturing mammalian host cells to express an antibody including an anti-reduction agent that minimizes reduction of a disulfide bond in the antibody or fragment thereof. In some other aspects, methods for minimizing disulfide bond reduction; increasing production of an antibody or fragment thereof with intact native disulfide bonds; increasing a ratio of non-reduced to reduced antibody or fragment thereof; producing a therapeutic antibody or fragment thereof by adding a sufficient amount of an anti-reduction agent to a cell culture media, pre-harvest cell culture fluid, or harvest cell culture fluid are described. In another aspect, minimizing disulfide bond reduction in an antibody or fragment thereof culturing the host cell in a concentration of at least about 20% $O_2$ is described.

19 Claims, 29 Drawing Sheets
Specification includes a Sequence Listing.

AQS

Control, unreduced antibody

Lipoic acid

Control, unreduced antibody

FIG. 12 B

| Sample | Time | % Fragments | % Intact IgG |
|---|---|---|---|
| Untreated | 0 h | 7.4 | 92.6 |
| No AQC | 2 h | 31.1 | 68.9 |
| + AQC | 2 h | None | 100 |
| No AQC | 6 h | 77.2 | 22.8 |
| + AQC | 6 h | 6.3 | 93.7 |
| No AQC | 24 h | 89.6 | 5.7 |
| + AQC | 24 h | 5.0 | 90.3 |
| No AQC | 48 h | 98.2 | 1.8 |
| + AQC | 48 h | 5.2 | 94.8 |
| No AQC | 68 h | 97.8 | 2.2 |
| + AQC | 68 h | 10.4 | 89.6 |

Cystine dimethyl ester (CDME)

Control, unreduced antibody

SEQUENCE LISTING

```
<160> NUMBER OF SEQ ID NOS: 9

<210> SEQ ID NO 1
<211> LENGTH: 257
<212> TYPE: PRT
<213> ORGANISM: Homo sapiens

<400> SEQUENCE: 1

Met Ala Gln Arg Met Thr Thr Gln Leu Leu Leu Leu Leu Val Trp Val
1               5                   10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Arg Lys Asn Ala
    50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
        115                 120                 125
```

```
Val Leu Asn Val Pro Leu Cys Lys Glu Asp Cys Glu Gln Trp Trp Glu
    130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser

<210> SEQ ID NO 2
<211> LENGTH: 771
<212> TYPE: DNA
<213> ORGANISM: Homo sapiens

<400> SEQUENCE: 2
atggctcagc ggatgacaac acagctgctg ctccttctag tgtgggtggc tgtagtaggg      60
gaggctcaga caaggattgc atgggccagg actgagcttc tcaatgtctg catgaacgcc     120
aagcaccaca aggaaaagcc aggccccgag acaagttgc atgagcagtg tcgaccctgg      180
aggaagaatg cctgctgttc taccaacacc agccaggaag cccataagga tgtttcctac     240
ctatatagat tcaactggaa ccactgtgga gagatggcac ctgcctgcaa acggcatttc     300
atccaggaca cctgcctcta cgagtgctcc cccaacttgg ggccctggat ccagcaggtg     360
gatcagagct ggcgcaaaga gcgggtactg aacgtgcccc tgtgcaaaga ggactgtgag     420
caatggtggg aagattgtcg cacctcctac acctgcaaga gcaactggca caagggctgg     480
aactggactt cagggtttaa caagtgcgca gtgggagctg cctgccaacc tttccatttc     540
tacttcccca cacccactgt tctgtgcaat gaaatctgga ctcactccta caaggtcagc     600
aactacagcc agggagtggg ccgctgcatc cagatgtggt tcgacccagc ccagggcaac     660
cccaatgagg aggtggcgag gttctatgct gcagccatga gtggggctgg gccctgggca     720
gcctggcctt tcctgcttag cctggcccta atgctgctgt ggctgctcag c              771

<210> SEQ ID NO 3
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
```

```
                35                  40                  45
Gly Arg Ile His Pro Tyr Asp Gly Asp Thr Phe Tyr Asn Gln Lys Phe
 50                  55                  60
Gln Gly Lys Ala Thr Leu Thr Val Asp Lys Ser Ser Asn Thr Ala His
 65                  70                  75                  80
Met Glu Leu Leu Ser Leu Thr Ser Glu Asp Phe Ala Val Tyr Tyr Cys
                 85                  90                  95
Thr Arg Tyr Asp Gly Ser Arg Ala Met Asp Tyr Trp Gly Gln Gly Thr
                100                 105                 110
Thr Val Thr Val Ser Ser
                115

<210> SEQ ID NO 4
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Val Leu Thr Gln Ser Pro Leu Ser Leu Ala Val Ser Leu Gly
 1               5                  10                  15
Gln Pro Ala Ile Ile Ser Cys Lys Ala Ser Gln Ser Val Ser Phe Ala
                20                  25                  30
Gly Thr Ser Leu Met His Trp Tyr His Gln Lys Pro Gly Gln Gln Pro
                35                  40                  45
Arg Leu Leu Ile Tyr Arg Ala Ser Asn Leu Glu Ala Gly Val Pro Asp
 50                  55                  60
Arg Phe Ser Gly Ser Gly Ser Lys Thr Asp Phe Thr Leu Asn Ile Ser
 65                  70                  75                  80
Pro Val Glu Ala Glu Asp Ala Ala Thr Tyr Tyr Cys Gln Gln Ser Arg
                 85                  90                  95
Glu Tyr Pro Tyr Thr Phe Gly Gly Gly Thr Lys Leu Glu Ile Lys Arg
                100                 105                 110

<210> SEQ ID NO 5
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Val Leu Thr Gln Ser Pro Leu Ser Leu Ala Val Ser Leu Gly
 1               5                  10                  15
Gln Pro Ala Ile Ile Ser Cys Lys Ala Ser Gln Ser Val Ser Phe Ala
                20                  25                  30
Gly Thr Ser Leu Met His Trp Tyr His Gln Lys Pro Gly Gln Gln Pro
                35                  40                  45
Arg Leu Leu Ile Tyr Arg Ala Ser Asn Leu Glu Ala Gly Val Pro Asp
 50                  55                  60
Arg Phe Ser Gly Ser Gly Ser Lys Thr Asp Phe Thr Leu Thr Ile Ser
 65                  70                  75                  80
Pro Val Glu Ala Glu Asp Ala Ala Thr Tyr Tyr Cys Gln Gln Ser Arg
                 85                  90                  95
Glu Tyr Pro Tyr Thr Phe Gly Gly Gly Thr Lys Leu Glu Ile Lys Arg
```

<210> SEQ ID NO 6
<211> LENGTH: 218
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

Asp Val Val Met Thr Gln Ser Pro Leu Ser Leu Pro Val Thr Leu Gln
1               5                   10                  15

Pro Ala Ser Ile Ser Cys Arg Ser Ser Gln Ile Ile Ile His Ser Asp
            20                  25                  30

Gly Asn Thr Tyr Leu Glu Trp Phe Gln Gln Arg Pro Gly Gln Ser Pro
        35                  40                  45

Arg Arg Leu Ile Tyr Lys Val Ser Asn Arg Phe Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Phe Gln Gly Ser
                85                  90                  95

His Val Pro His Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 7
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Gly Ser Phe Thr Ile Tyr Tyr Ala Asp Ser Val
    50                  55                  60

Lys Gly Arg Phe Thr Ile Ser Arg Asp Asn Ser Lys Asn Thr Leu Tyr

```
            65                  70                  75                  80
Leu Gln Met Asn Ser Leu Arg Ala Glu Asp Thr Ala Val Tyr Tyr Cys
                    85                  90                  95

Ala Arg Met Arg Lys Gly Tyr Ala Met Asp Tyr Trp Gly Gln Gly Thr
                100                 105                 110

Leu Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 8
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 8

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ile Ile Ile His Ser
            20                  25                  30

Asp Gly Asn Thr Tyr Leu Glu Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro His Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 9
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Gly Ser Phe Thr Ile Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Arg Lys Gly Tyr Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125
```

```
Leu Ala Pro Ser Ser Lys Ser Thr Ser Gly Gly Thr Ala Ala Leu Gly
        130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
                180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
        210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
                260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
        290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
        370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly Lys
        435                 440                 445
```

COMPOSITIONS AND METHODS FOR ANTIBODY PRODUCTION

PRIORITY CLAIM

This application claims priority to U.S. Provisional Application No. 62/507,528, filed May 17, 2017. The entire contents of that application are hereby incorporated herein.

SEQUENCE LISTING

The instant application contains a Sequence Listing which has been submitted electronically in ASCII format and is hereby incorporated by reference in its entirety. Said ASCII copy, created on Dec. 12, 2018, is named P188 US002 SL.txt and is 18,907 bytes in size.

BACKGROUND OF THE INVENTION

Antibodies, or immunoglobulins, contain heavy and light chains that are held together by non-covalent interactions as well as by covalent interchain disulfide bonds. Human immunoglobulin G (IgG) isotypes, IgG1, IgG2, IgG3, and IgG4, contain one disulfide bond between the heavy chain and light chain, whereas the number of disulfide bonds between the two heavy chains is two for IgG1 and IgG4, four for IgG2, and eleven for IgG3. The inter-chain disulfide bonds in the antibody are more accessible to solvent than intrachain disulfide bonds, and can be reduced to thiol residues by dithiol agents, such as dithiothreitol.

Several monoclonal antibody based therapeutics, which include the antibody-drug conjugates brentuximab vedotin and ado-trastuzumab emtansine, are currently approved for clinical use in various indications, such as oncology and rheumatoid arthritis. These recombinant monoclonal antibodies are produced at high titers in cells, such as CHO, SP2/0, and NS0 cells. The recombinant antibodies are generated by mammalian cells that secrete the antibodies into the medium. At the end of the antibody production process, the cells are separated from the antibody-containing medium using methods, such as tangential flow micro filtration, centrifugation, depth filtration, flocculation or precipitation and then purified, for example, by affinity chromatography. During the cell separation step, cell damage may occur causing the release of intracellular reducing proteins. Without wishing to be bound by theory, the release of such proteins could undesirably reduce the inter-chain disulfide bonds present in antibodies or other recombinant proteins.

The cysteine content of mammalian proteins is typically about two percent, of which about 70% cysteine thiols are exposed and available for redox reactions. This suggests that a large number of intracellular proteins could be involved in intracellular redox homeostasis. In one study, 24 thiol proteins sensitive to oxidation were identified in a human cell line, including glyceraldehyde-3-phosphate dehydrogenase, peroxyredoxin 2, glutathione-S-transferase P1-1, enolase, Protein kinase A subunit, annexin VI, serine/threonine kinase BUB1β, heat-shock protein 90β, and proteosome components. Other studies have reported the anti-oxidant functions of thioredoxin and glutaredoxin systems in cells. A significantly high percentage (5%) of soluble cellular proteins have vicinal thiol groups, which could have high reduction potential. About 5-15% of mitochondrial proteins are reported to have vicinal thiol groups. All of these thiol-containing intracellular proteins could be released by cell damage during the cell separation step prior to the antibody purification step, and could lead to the reduction of the antibody inter-chain disulfide groups. Given that the native, inter-chain disulfide bonds in the antibody contribute to the thermodynamic stability of the antibody, any reduction could lead to instability of the antibody, which is undesirable in a therapeutic antibody or antibody drug conjugate. Improved methods for protecting disulfide bonds present in antibodies and/or other recombinant proteins are needed.

SUMMARY OF THE INVENTION

As described below, the invention features compositions and methods for minimizing fragmentation and disulfide bond reduction in antibodies and recombinant proteins.

In one aspect, the invention provides a cell culture, harvest or pre-harvest composition (e.g., cell culture media, harvest cell culture fluid, or pre-harvest cell culture fluid) containing an effective amount of an anti-reduction agent that is any one or more of methylene blue, a quinone (e.g., a substituted benzoquinone; 1,2-naphthoquinone-4-sulfonic acid; and anthraquinone-2-sulfonic acid); a coenzyme Q analog (e.g., coenzyme Q0 and/or coenzyme Q2), a disulfide (e.g., disulfiram; lipoic acid; a soluble cystine analog); a combination of glutathione reductase and oxidized glutathione (GSSG); oxidized glutathione alkyl esters (e.g., oxidized glutathione methyl esters; oxidized glutathione ethyl esters; oxidized glutathione isopropyl esters); 5,5'-dithiobis (2-nitrobenzoic acid) (DTNB), a salt thereof and any combinations thereof.

In one embodiment, the substituted benzoquinone is represented by formula (I):

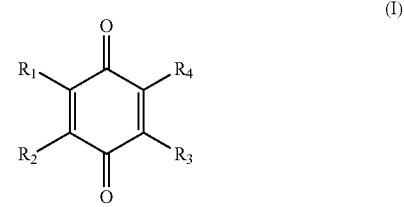

where $R_1$, $R_2$, $R_3$, and $R_4$ is each independently selected from the group consisting of H, alkyl, alkoxy, COOH, and $SO_3H$.

In one embodiment, the cystine analog is any one or more of cystine dimethyl ester, cystine diethyl ester, cystine methyl ester, cystine ethyl ester, di-N-acetyl cystine, cystine bis(t-butyl ester), cystine mono(t-butyl ester), monoesters of cystine, asymmetric (i.e., mixed) esters of cystine, and combinations thereof. In another embodiment, the composition contains one or more of a mixture of anthraquinone-2-sulfonic acid and cystine dimethyl ester; a mixture of lipoic acid and anthraquinone-2-sulfonic acid; and a mixture of lipoic acid and cystine dimethyl ester.

In another aspect, the invention provides a cell culture, harvest or pre-harvest composition (e.g., cell culture media, harvest cell culture fluid, or pre-harvest cell culture fluid) containing an effective amount of one or more of methylene blue; a substituted benzoquinone; 1,2-naphthoquinone-4-sulfonic acid; anthraquinone-2-sulfonic acid; lipoic acid; disulfiram; a soluble cystine analog; a combination of glutathione reductase and oxidized glutathione (GSSG); oxidized glutathione alkyl esters (e.g., oxidized glutathione methyl esters; oxidized glutathione ethyl esters; oxidized glutathione isopropyl esters); and 5,5'-dithiobis(2-nitrobenzoic acid) (DTNB).

In yet another aspect, the invention provides a method for minimizing disulfide bond reduction in a recombinant protein, antibody or fragment thereof expressed in a host cell, the method involving adding an anti-reduction agent to a cell culture media, pre-harvest culture fluid, or harvest culture fluid, containing the antibody or fragment thereof, where the anti-reduction agent is any one or more of methylene blue, a quinone, a disulfide, a salt thereof and any combinations thereof.

In yet another aspect, the invention provides a method of increasing a ratio of non-reduced to reduced protein, antibody, or fragment thereof, that is produced by a mammalian host cell, the method involving adding a sufficient amount of an anti-reduction agent to a cell culture media, pre-harvest cell culture fluid, or harvest cell culture fluid, containing the antibody or fragment thereof, where the anti-reduction agent is any one or more of methylene blue, a quinone, a disulfide, a salt thereof, and combinations thereof.

In yet another aspect, the invention provides a method for preventing or minimizing disulfide bond reduction or fragmentation in an antibody, antibody fragment, or recombinantly expressed protein, the method involving contacting the protein with an anti-reduction agent that is any one or more selected from the group consisting of methylene blue; a substituted benzoquinone; 1,2-naphthoquinone-4-sulfonic acid; anthraquinone-2-sulfonic acid; lipoic acid; disulfiram; a soluble cystine analog; a combination of glutathione reductase and oxidized glutathione (GSSG); oxidized glutathione alkyl esters; and 5,5'-dithiobis(2-nitrobenzoic acid) (DTNB), where the antibody, antibody fragment, or recombinantly expressed protein is contacted during expression in a host cell, during cell culture, pre-harvest, or harvest.

In still another aspect, the invention provides a method of increasing production of a protein, antibody or fragment thereof with intact native disulfide bonds that is expressed in a mammalian host cell, the method involving adding an effective amount of an anti-reduction agent to a cell culture media, pre-harvest culture fluid, or harvest culture fluid, containing the antibody or fragment thereof, where the anti-reduction agent is any one or more selected from the group consisting of methylene blue, a quinone, a disulfide, a salt thereof, and combinations thereof.

In still another aspect, the invention provides a method of producing a therapeutic antibody, or fragment thereof, the method involving exposing a mammalian host cell that produces the therapeutic antibody or fragment thereof, to a composition containing a sufficient amount of an anti-reduction agent in a cell culture media, pre-harvest cell culture fluid, or harvest cell culture fluid, where the anti-reduction agent is any one or more selected from the group consisting of methylene blue, a quinone, a disulfide, a salt thereof, and any combinations thereof.

In still another aspect, the invention provides a method of minimizing disulfide bond reduction in a recombinant protein, antibody or fragment thereof that is expressed in a mammalian host cell, the method involving sparging the cell culture medium, pre-harvest cell culture fluid, or harvest cell culture fluid with oxygen to a concentration of at least about 20% dissolved $O_2$. In one embodiment, the concentration of dissolved $O_2$ is in a range of about 20% to about 100%.

A method of minimizing disulfide bond reduction in a recombinant protein, antibody or fragment thereof that is expressed in a mammalian host cell, the method comprising sparging the cell culture medium, pre-harvest cell culture fluid, or harvest cell culture fluid with a combination of air and oxygen to a concentration of at least about 20% dissolved $O_2$. In one embodiment, the concentration of dissolved $O_2$ is in a range of about 20% to about 100%.

In various embodiments of the above aspects or any other aspect of the invention delineated herein, the anti-reduction agent does not covalently modify the protein, antibody or fragment thereof. In other embodiments of the above aspects or any other aspect of the invention, the anti-reduction agent is at a sub-stoichiometric concentration to that of total thiol in the solution. In other embodiments of the above aspects or any other aspect of the invention, the anti-reduction agent is present at a concentration from about 0.01 mM to about 100 mM (e.g., 0.01, 0.05, 0.1, 0.5, 1, 2, 5, 10, 20, 30, 40, 50, 60, 70, 80, 90, 100); from about 0.1 mM to about 10 mM (e.g., 0.1, 0.2, 0.3, 0.4, 0.5, 0.6, 0.7, 0.8, 0.9, 1, 2, 3, 4, 5, 6, 7, 8, 9, 10). In other embodiments of the above aspects or any other aspect of the invention, the composition is cell culture media, harvest cell culture fluid, or pre-harvest cell culture fluid. In other embodiments of the above aspects or any other aspect of the invention, the protein, antibody, or fragment thereof, has a thiol:antibody ratio of at least about 25, 50, 75, 90, 95, or even 100% lower in the presence of the anti-reduction agent than in the absence of the anti-reduction agent. In other embodiments of the above aspects or any other aspect of the invention, the ratio is decreased by at least about 2, 5, 10, or 20-fold.

In other embodiments of the above aspects or any other aspect of the invention delineated herein, a quinone is any one or more of a substituted benzoquinone; 1,2-naphthoquinone-4-sulfonic acid; anthraquinone-2-sulfonic acid; a coenzyme Q, and combinations thereof. In one embodiment, a quinone is anthraquinone-2-sulfonic acid. In another embodiment, the substituted benzoquinone is represented by formula (I):

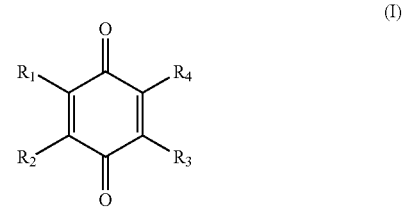

where $R_1$, $R_2$, $R_3$, and $R_4$ is each independently selected from the group consisting of H, alkyl, alkoxy, COOH, and $SO_3H$.

In other embodiments of the above aspects or any other aspect of the invention, the coenzyme Q analog is coenzyme Q0 and/or coenzyme Q2. In other embodiments of the above aspects or any other aspect of the invention, the disulfide is any one or more of a disulfiram; lipoic acid; a soluble cystine analog; a combination of glutathione reductase and oxidized glutathione (GSSG); oxidized glutathione alkyl esters (e.g., oxidized glutathione methyl esters; oxidized glutathione ethyl esters; oxidized glutathione isopropyl esters); 5,5'-dithiobis(2-nitrobenzoic acid) (DTNB) and combinations thereof. In one embodiment, the disulfide is lipoic acid. In other embodiments of the above aspects or any other aspect of the invention, the cystine analog is any one or more of cystine dimethyl ester, cystine diethyl ester, cystine methyl ester, cystine ethyl ester, di-N-acetyl cystine, cystine bis(t-butyl ester), monesters of cystine, asymmetric esters of cystine, and combinations thereof. In one embodiment, the cystine analog is cystine dimethyl ester, cystine bis(t-butyl ester), or any combinations thereof. In another embodiment, the cystine analog is cystine bis(t-butyl ester). In yet another embodiment, the cystine analog comprises cystine dimethyl ester (CDME) and cystine bis(t-butyl ester). In one preferred embodiment, the cystine bis(t-butyl ester) comprises L-cystine bis (t-butyl ester)(CDBE). In another preferred embodiment, the cystine analog is cystine dimethyl ester. In other embodiments of the above aspects or any other aspect of the invention, the composition contains a mixture of anthraquinone-2-sulfonic acid and cystine dimethyl ester; a mixture of lipoic acid and anthraquinone-2-sulfonic acid; or a mixture of lipoic acid and cystine dimethyl ester. In other embodiments of the above aspects or any other aspect of the invention, the method involves adding the anti-reduction agent to the cell culture medium (e.g., within about 15 minutes, 30 minutes, 45 minutes, 60 minutes, 75 minutes, 90 minutes, 105 minutes, 2 hours, 4 hours, 6 hours, 8 hours, 10 hours, 12 hours, 24 hours, 48 hours of harvesting the cell culture). In one embodiment, the method comprises adding the anti-reduction agent to the cell culture medium within about 15 minutes of harvesting the cell culture.

In other embodiments of the above aspects or any other aspect of the invention, the step of adding the anti-reduction agent does not decrease viability of the cells by greater than about 15%. In other embodiments of the above aspects or any other aspect of the invention, the method involves adding the anti-reduction agent to the pre-harvest cell culture fluid or to the harvest cell culture fluid. In other embodiments of the above aspects or any other aspect of the invention, the anti-reduction agent is added at a sub-stoichiometric concentration to that of total thiol in the solution.

In other embodiments of the above aspects or any other aspect of the invention, the anti-reduction agent is added at a molar ratio of about 0.1 to about 0.8 of a total thiol concentration in the cell culture media, pre-harvest cell culture fluid, or harvest cell culture fluid. In another embodiment, the anti-reduction agent is added at a molar ratio of about 0.1 to about 10 of a total thiol concentration in the cell culture media, pre-harvest cell culture fluid, or harvest cell culture fluid. In other embodiments of the above aspects or any other aspect of the invention, the anti-reduction agent is added to a final concentration in a range from about 0.01 mM to about 100 mM. In other embodiments of the above aspects or any other aspect of the invention, the final concentration of the anti-reduction agent ranges from about 0.1 mM to about 10 mM. In other embodiments of the above aspects or any other aspect of the invention, the method involves sparging the cell culture medium, pre-harvest cell culture fluid, or harvest cell culture fluid with air or oxygen to a concentration of at least about 20% dissolved $O_2$. In other embodiments of the above aspects or any other aspect of the invention, the concentration of dissolved $O_2$ is in a range of about 20% to about 100% (e.g., 20, 25, 50, 75, 90, 95, 99, 100%).

In other embodiments of the above aspects or any other aspect of the invention, the mammalian host cell is a Chinese Hamster Ovary (CHO) cell. In other embodiments of the above aspects or any other aspect of the invention, the antibody is any one or more of an anti-FOLR1 antibody (e.g., SEQ ID NO.: 3, 4, or 5), an anti-CD56 antibody (e.g., huN901), an anti-CD37 antibody, an anti-EGFR antibody, an anti-IGF-1R antibody, an anti-MUC1, an anti-CA6 glycotope, an anti-CD19 antibody, and an anti-CD33 antibody. In other embodiments of the above aspects or any other aspect of the invention, the antibody is at least one of an IgG1, IgG2, IgG3, and IgG4 isotype. In one embodiment, the antibody is an IgG1 isotype. In other embodiments of the above aspects or any other aspect of the invention, the antibody or fragment thereof is not covalently modified by the anti-reduction agent. In other embodiments of the above aspects or any other aspect of the invention, the method does not increase immunogenicity of the antibody or fragment thereof. In other embodiments of the above aspects or any other aspect of the invention, the antibody is recombinantly expressed in the host cell. In other embodiments of the above aspects or any other aspect of the invention, the antibody is any one or more of a therapeutic antibody, a modified antibody and a conjugated antibody.

In another aspect, the disclosure provides a method for minimizing disulfide bond reduction in a recombinant protein, antibody or fragment thereof expressed in a host cell. The method comprises adding an anti-reduction agent to a cell culture media, pre-harvest cell culture fluid, or harvest cell culture fluid, comprising the antibody or fragment thereof, wherein the anti-reduction agent is selected from the group consisting of methylene blue, a quinone, a disulfide, a salt thereof and any combinations thereof.

In yet another aspect, the disclosure provides a method for preventing or minimizing disulfide bond reduction or fragmentation in an antibody, antibody fragment, or recombinantly expressed protein. The method comprises contacting the protein with an anti-reduction agent selected from the group consisting of methylene blue; a substituted benzoquinone; 1,2-naphthoquinone-4-sulfonic acid; anthraquinone-2-sulfonic acid; lipoic acid; disulfiram; a soluble cystine analog; a combination of glutathione reductase and oxidized glutathione (GSSG); oxidized glutathione alkyl esters; oxidized glutathione methyl esters; oxidized glutathione ethyl esters; oxidized glutathione isopropyl esters; and 5,5'-dithiobis(2-nitrobenzoic acid) (DTNB), wherein the antibody, antibody fragment, or recombinantly expressed protein is contacted during expression in a host cell, during cell culture, pre-harvest, or harvest.

In some embodiments of the methods disclosed herein, the protein, antibody, or fragment thereof, has a thiol:antibody ratio of at least about 25% lower in the presence of the anti-reduction agent than in the absence of the anti-reduction agent.

In some embodiments of the methods disclosed herein, the protein, antibody, or fragment thereof, has a thiol:antibody ratio of at least about 50% lower in the presence of the anti-reduction agent than in the absence of the anti-reduction agent.

In another aspect, the disclosure provides a method of increasing production of a protein, antibody or fragment thereof with intact native disulfide bonds that is expressed in a mammalian host cell. The method comprises adding an effective amount of an anti-reduction agent to a cell culture media, pre-harvest cell culture fluid, or harvest cell culture fluid, comprising the antibody or fragment thereof, wherein the anti-reduction agent is selected from the group consisting of methylene blue, a quinone, a disulfide, a salt thereof, and any combinations thereof.

In some embodiments of the methods disclosed herein, the protein, antibody, or fragment thereof, has a thiol:antibody ratio of at least about 25% lower in the presence of the anti-reduction agent than in the absence of the anti-reduction agent.

In some embodiments of the methods disclosed herein, the protein, antibody, or fragment thereof, has a thiol:antibody ratio of at least about 50% lower in the presence of the anti-reduction agent than in the absence of the anti-reduction agent.

Another aspect of the disclosure provides a method of increasing a ratio of non-reduced to reduced protein, antibody, or fragment thereof, that is produced by a mammalian host cell. The method comprises adding a sufficient amount of an anti-reduction agent to a cell culture media, pre-harvest cell culture fluid, or harvest cell culture fluid, comprising the antibody or fragment thereof, wherein the anti-r agent is selected from the group consisting of methylene blue, a quinone, a disulfide, a salt thereof, and combinations thereof.

In some embodiments of the methods disclosed herein, the ratio is increased by at least about 2-fold. In some embodiments of the methods disclosed herein, the ratio is increased by at least about 10-fold.

Another aspect of the disclosure provides a method of producing a therapeutic antibody, or fragment thereof. The method comprises exposing a mammalian host cell that produces the therapeutic antibody or fragment thereof, to a composition comprising a sufficient amount of an anti-reduction agent in a cell culture media, pre-harvest cell culture fluid, or harvest cell culture fluid, wherein the anti-reduction agent is at least one selected from the group consisting of methylene blue, a quinone, a disulfide, a salt thereof, and any combinations thereof.

In some embodiments, the quinone is selected from the group consisting of a substituted benzoquinone; 1,2-naphthoquinone-4-sulfonic acid; anthraquinone-2-sulfonic acid; a coenzyme Q, and combinations thereof. In certain embodiments, the quinone is anthraquinone-2-sulfonic acid. In some embodiments, the substituted benzoquinone is represented by formula (I):

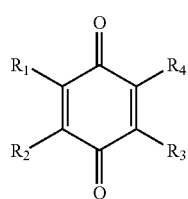

(I)

wherein R1, R2, R3, and R4 is each independently selected from the group consisting of H, alkyl, alkoxy, COOH, and SO3H.

In some embodiments of the methods disclosed herein, the coenzyme Q analog is selected from the group consisting of coenzyme Q0, coenzyme Q2, and combinations thereof.

In some embodiments of the methods disclosed herein, the disulfide is selected from the group consisting of a disulfiram; lipoic acid; a soluble cystine analog; a combination of glutathione reductase and oxidized glutathione (GSSG); oxidized glutathione alkyl esters;

oxidized glutathione methyl esters; oxidized glutathione ethyl esters; oxidized glutathione isopropyl esters; 5,5'-dithiobis(2-nitrobenzoic acid) (DTNB) and any combinations thereof. In some embodiments, the disulfide is lipoic acid.

In some embodiments of the methods disclosed herein, the cystine analog is selected from the group consisting of cystine dimethyl ester, cystine diethyl ester, cystine methyl ester, cystine ethyl ester, di-N-acetyl cystine, L-cystine bis(methyl ester), L-cystine bis(t-butyl ester), and combinations thereof. In some embodiments, the cystine analog is cystine dimethyl ester, L-cystine bis(t-butyl ester), or combinations thereof.

In some embodiments of the methods disclosed herein, the composition comprises one or more selected from the group consisting of a mixture of anthraquinone-2-sulfonic acid and cystine dimethyl ester; a mixture of anthraquinone-2-sulfonic acid and cystine bis(t-butyl) ester; a mixture of lipoic acid and anthraquinone-2-sulfonic acid; a mixture of lipoic acid and cystine dimethyl ester; a mixture of lipoic acid and cystine bis(t-butyl) ester, or any combinations thereof.

In some embodiments of the methods disclosed herein, the method comprises adding the anti-reduction agent to the cell culture medium. In some embodiments, the method comprises adding the anti-reduction agent to the cell culture medium within about 48 hours of harvesting the cell culture. In some embodiments, the method comprises adding the anti-reduction agent to the cell culture medium within about 24 hours of harvesting the cell culture. In still other embodiments, the method comprises adding the anti-reduction agent to the cell culture medium within about 12 hours of harvesting the cell culture. In further embodiments, the method comprises adding the anti-reduction agent to the cell culture medium within about 15 minutes of harvesting the cell culture.

In some embodiments of the methods disclosed herein, the step of adding the anti-reduction agent does not decrease viability of the cells by greater than about 15%.

In some embodiments of the methods disclosed herein, the method comprises adding the anti-reduction agent to the pre-harvest cell culture fluid.

In some embodiments of the methods disclosed herein, the method comprises adding the anti-reduction agent to the harvest cell culture fluid.

In some embodiments of the methods disclosed herein, the anti-reduction agent is added at a sub-stoichiometric concentration.

In some embodiments of the methods disclosed herein, the anti-reduction agent is added at a molar ratio of about 0.1 to about 10 of a total thiol concentration in the cell culture media, pre-harvest cell culture fluid, or harvest cell culture fluid. In some embodiments, the anti-reduction agent is added to a final concentration in a range from about 0.01 mM to about 100 mM. In further embodiments, the final concentration of the anti-reduction agent ranges from about 0.1 mM to about 10 mM.

In some embodiments of the methods disclosed herein, the method comprises sparging the cell culture medium, pre-harvest cell culture fluid, or harvest cell culture fluid with air or oxygen to a concentration of at least about 20% dissolved O2. In some embodiments, the concentration of dissolved O2 is in a range of about 20% to about 100%.

Yet another aspect of this disclosure provides a method of minimizing disulfide bond reduction in a recombinant protein, antibody or fragment thereof that is expressed in a mammalian host cell. The method comprises sparging the cell culture medium, pre-harvest cell culture fluid, or harvest cell culture fluid with oxygen to a concentration of at least about 20% dissolved $O_2$.

One aspect of the disclosure provides a method of minimizing disulfide bond reduction in a recombinant protein, antibody or fragment thereof that is expressed in a mammalian host cell. The method comprises sparging the cell culture medium, pre-harvest cell culture fluid, or harvest cell culture fluid with a combination of air and oxygen to a concentration of at least about 20% dissolved O2.

In some embodiments of the methods disclosed herein, the concentration of dissolved O2 is in a range of about 20% to about 100%.

In some embodiments of the methods disclosed herein, the mammalian host cell is a Chinese Hamster Ovary (CHO) cell.

In some embodiments of the methods disclosed herein, the antibody is selected from an anti-FOLR1 antibody, an anti-CD56 antibody, an anti-CD37 antibody, an anti-EGFR antibody, an anti-IGF-1R antibody, an anti-MUC1, an anti-CA6 glycotope, an anti-CD19 antibody, and an anti-CD33 antibody. In some embodiments, the anti-FOLR1 antibody comprises a heavy chain or light chain variable region sequence represented by SEQ ID NO.: 3, 4, or 5. In some embodiments, the anti-CD56 antibody is huN901.

In some embodiments of the methods disclosed herein, the antibody is at least one of an IgG1, IgG2, IgG3, and IgG4 isotype. In certain embodiments, the antibody is an IgG1 isotype.

In some embodiments of the methods disclosed herein, the antibody or fragment thereof is not covalently modified by the anti-reduction agent.

In some embodiments of the methods disclosed herein, the method does not increase immunogenicity of the antibody or fragment thereof.

In some embodiments, the antibody is recombinantly expressed in the host cell. In some embodiments, the antibody is selected from the group consisting of a therapeutic antibody, a modified antibody and a conjugated antibody.

In another aspect, the disclosure provides a cell culture, harvest or pre-harvest composition comprising an effective amount of an anti-reduction agent selected from the group consisting of methylene blue, a quinone, a disulfide, a salt thereof and any combinations thereof. In some embodiments, the quinone is at least one of a substituted benzoquinone; 1,2-naphthoquinone-4-sulfonic acid; and anthraquinone-2-sulfonic acid; a coenzyme Q analog, and combinations thereof. In some embodiments, the substituted benzoquinone is represented by formula (I):

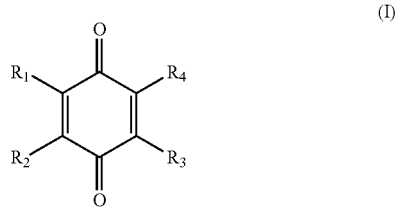

wherein $R_1$, $R_2$, $R_3$, and $R_4$ is each independently selected from the group consisting of H, alkyl, alkoxy, COOH, and $SO_3H$.

In some embodiments, the coenzyme Q analog is one or more selected from the group consisting of coenzyme Q0, coenzyme Q2, and combinations thereof.

In some embodiments, the disulfide is one or more selected from the group consisting of disulfiram; lipoic acid; a soluble cystine analog; a combination of glutathione reductase and oxidized glutathione (GSSG); oxidized glutathione alkyl esters; oxidized glutathione methyl esters; oxidized glutathione ethyl esters; oxidized glutathione isopropyl esters; 5,5'-dithiobis(2-nitrobenzoic acid) (DTNB), and any combinations thereof.

In some embodiments, the cystine analog is one or more selected from the group consisting of cystine dimethyl ester, cystine diethyl ester, cystine bis(t-butyl) ester, cystine methyl ester, cystine ethyl ester, cystine t-butyl ester, di-N-acetyl cystine, L-cystine bis(methyl ester), L-cystine bis(t-butyl ester), and any combinations thereof.

In some embodiments, the composition comprises one or more selected from the group consisting of a mixture of anthraquinone-2-sulfonic acid and cystine dimethyl ester; a mixture of anthraquinone-2-sulfonic acid and cystine bis(t-butyl) ester; a mixture of lipoic acid and anthraquinone-2-sulfonic acid; a mixture of lipoic acid and cystine dimethyl ester; a mixture of lipoic acid and cystine bis(t-butyl) ester, and any combinations thereof.

In certain embodiments, the anti-reduction agent does not covalently modify the antibody or fragment thereof. In some embodiments, the anti-reduction agent is at a sub-stoichiometric concentration. In some embodiments, the anti-reduction agent is present at a concentration from about 0.01 mM to about 100 mM. In further embodiments, the anti-reduction agent is present at a concentration from about 0.1 mM to about 10 mM.

In another aspect, the disclosure provides a cell culture, harvest or pre-harvest composition comprising an effective amount of one or more selected from the group consisting of methylene blue; a substituted benzoquinone; 1,2-naphthoquinone-4-sulfonic acid; anthraquinone-2-sulfonic acid; lipoic acid; disulfiram; a soluble cystine analog; a combination of glutathione reductase and oxidized glutathione (GSSG); oxidized glutathione alkyl esters; oxidized glutathione alkyl esters; oxidized glutathione methyl esters; oxidized glutathione ethyl esters; oxidized glutathione isopropyl esters; and 5,5'-dithiobis(2-nitrobenzoic acid) (DTNB).

In some embodiments of the methods and compositions disclosed herein, the composition is cell culture media, harvest cell culture fluid, or pre-harvest cell culture fluid.

Another aspect of this disclosure provides method of inhibiting disulfide bond reduction in a recombinant protein, antibody, or fragment thereof expressed in a host cell. The method comprises adding an anti-reduction agent to a cell culture media, pre-harvest cell culture fluid, or harvest cell culture fluid, comprising the antibody or fragment thereof, wherein the anti-reduction agent is an organic redox active anti-reduction agent or an inorganic redox active anti-reduction agent. In some embodiments, the anti-reduction agent is selected from the group consisting of $ZnSO_4$, $CuSO_4$, $NiSO_4$, $NaNO_3$, and any combinations thereof.

A further aspect of this disclosure provides a method of inhibiting disulfide bond reduction or fragmentation in an antibody, antibody fragment, or recombinantly expressed protein. The method comprises contacting the antibody, antibody fragment, or recombinantly expressed protein with an anti-reduction agent, wherein the anti-reduction agent is an organic redox active anti-reduction agent or an inorganic redox active anti-reduction agent. In some embodiments, the anti-reduction agent is selected from the group consisting of $ZnSO_4$, $CuSO_4$, $NiSO_4$, $NaNO_3$, and any combinations thereof, wherein the antibody, antibody fragment, or recombinantly expressed protein is contacted during expression in a host cell, during cell culture, pre-harvest, or harvest.

Yet another aspect of this disclosure provides a method of increasing production of a protein, antibody, or antibody fragment with intact native disulfide bonds that is expressed in a mammalian host cell, the method comprising adding an effective amount of an anti-reduction agent to a cell culture media, pre-harvest cell culture fluid, or harvest cell culture fluid, comprising the antibody or fragment thereof, wherein the anti-reduction agent is an organic redox active anti-reduction agent or an inorganic redox active anti-reduction agent. In some embodiments, the anti-reduction agent is selected from the group consisting of $ZnSO_4$, $CuSO_4$, $NiSO_4$, $NaNO_3$, and any combinations thereof.

In some embodiments of the methods disclosed herein, greater than about 80% of the protein, antibody, or antibody fragment produced has intact native disulfide bonds. In further embodiments, greater than about 90% of the protein, antibody, or antibody fragment produced has intact native disulfide bonds.

In some embodiments of the methods disclosed herein, the method comprises adding the anti-reduction agent to the cell culture media. In some embodiments, the method comprises adding the anti-reduction agent to the cell culture medium within about 48 hours of harvesting the cell culture. In some embodiments, the method comprises adding the anti-reduction agent to the cell culture medium within about 24 hours of harvesting the cell culture. In some embodiments, the method comprises adding the anti-reduction agent to the cell culture medium within about 12 hours of harvesting the cell culture. In some embodiments, the method comprises adding the anti-reduction agent to the cell culture medium within about 15 minutes of harvesting the cell culture. In some embodiments, the method comprises adding the anti-reduction agent to the pre-harvest cell culture fluid.

In some embodiments of the methods disclosed herein, the method comprises adding the anti-reduction agent to the harvest cell culture fluid.

In some embodiments of the methods disclosed herein, the anti-reduction agent is added to a final concentration in a range from about 0.01 mM to about 100 mM.

In some embodiments of the methods disclosed herein, the mammalian host cell is a Chinese Hamster Ovary (CHO) cell.

In some embodiments of the methods disclosed herein, the antibody is selected from an anti-FOLR1 antibody, an anti-CD56 antibody, an anti-CD37 antibody, an anti-EGFR antibody, an anti-IGF-1R antibody, an anti-MUC1, an anti-CA6 glycotope, an anti-CD19 antibody, and an anti-CD33 antibody. In some embodiments, the anti-FOLR1 antibody comprises a heavy chain or light chain variable region sequence represented by SEQ ID NO.: 3, 4, or 5. In some embodiments, the anti-FOLR1 antibody is huMov19. In further embodiments, the anti-FOLR1 antibody is huN901.

Another aspect of this disclosure provides a cell culture, harvest, or pre-harvest composition comprising an effective amount of an anti-reduction agent, wherein the anti-reduction agent is an organic redox active anti-reduction agent or an inorganic redox active anti-reduction agent. In some embodiments, the anti-reduction agent is selected from the group consisting of $ZnSO_4$, $CuSO_4$, $NiSO_4$, $NaNO_3$, and any combinations thereof. In some embodiments the agent is an organic redox active anti-reduction agent. In some embodiments, the agent is an inorganic redox active anti-reduction agent. In some embodiments, the anti-reduction agent is present at a concentration ranging from about 0.01 mM to about 100 mM. In some embodiments, the anti-reduction agent is present at a concentration ranging from about 0.1 mM to about 10 mM. In some embodiments, the anti-reduction agent is present at a concentration of about 1 mM.

In some embodiments, the composition is cell culture media, harvest cell culture fluid, or pre-harvest cell culture fluid.

Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "antibody" or "antibodies" is meant an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact monoclonal antibodies, antibody fragments (such as Fab, Fab', F(ab')2, and Fv fragments), single chain antibodies, linear antibodies, diabodies (dAb), single domain heavy chain antibodies, a single domain light chain antibodies, single chain Fv (scFv), multispecific antibodies such as bispecific antibodies generated from at least two intact antibodies, chimeric antibodies, humanized antibodies, human antibodies, fusion proteins comprising an antigen binding portion of an antibody, and any other modified antibody or immunoglobulin molecule comprising an antigen recognition site so long as the antibodies exhibit the desired biological activity. In one example, the modified antibody is a probody or an antibody or antibody fragment coupled to a masking moiety or a cleavable moiety, wherein the masking moiety or cleavable moiety is capable of being removed, cleaved, reduced or photolysed. In another example the modified antibody is an antibody that includes a site specific (e.g., N-terminus, C-terminus, or cysteine modified or engineered) modification. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins or radioisotopes. In one example, the antibody is conjugated to a cytotoxic agent (e.g., a maytansinoid) to form an antibody-drug-conjugate (ADC).

By "anti-folate receptor 1 (FOLR1) antibody" is meant an antibody or fragment thereof that specifically binds a folate receptor 1 polypeptide. Non-limiting examples of an anti-FOLR1 antibody include mov19 and humanized (e.g., CDR grafted or resurfaced) versions thereof (huMov19"). The sequences for exemplary anti-FOLR1 antibodies are disclosed, for example, in U.S. Pat. No. 8,557,966, and in U.S. Patent Publication Nos. 2012/0282175 and 2012/0009181, each of which is incorporated by reference herein in its entirety. In particular embodiments, the anti-FOLR1 antibody comprises a variable heavy chain and/or variable light chain that is substantially identical (e.g., at least about 85%, 90%, 95%) to one of the following exemplary sequences:

huMov19 vHC

SEQ ID NO: 3
QVQLVQSGAEVVKPGASVKISCKASGYTFTGYFMNWVKQSPGQSLEWIGR

```
IHPYDGDTFYNQKFQGKATLTVDKSSNTAHMELLSLTSEDFAVYYCTRYD
GSRAMDYWGQGTTVTVSS huMov19 vLCv1.00
                                        SEQ ID NO: 4
DIVLTQSPLSLAVSLGQPAIISCKASQSVSFAGTSLMHWYHQKPGQQPRL
LTYRASNLEAGVPDRFSGSGSKTDFTLNISPVEAEDAATYYCQQSREYPY
TFGGGTKLEIKR huMov19 vLCv1.60
                                        SEQ ID NO: 5
DIVLTQSPLSLAVSLGQPAIISCKASQSVSFAGTSLMHWYHQKPGQQPRL
LTYRASNLEAGVPDRFSGSGSKTDFTLTISPVEAEDAATYYCQQSREYPY
TFGGGTKLEIKR
```

By "anti-CD56 antibody" is meant an antibody or fragment thereof that specifically binds a CD56 polypeptide. One example of an anti-CD56 antibody is the N901 antibody and humanized (e.g., CDR grafted and resurfaced) versions thereof. The preparation and exemplary sequences of versions of humanized N901 ("huN901"), are described, for example, by Roguska et al, Proc. Natl. Acad. Sci. USA, 91:969-973 (1994), and Roguska et al, Protein Eng., 9:895:904 (1996), the disclosures of which are incorporated by reference herein in their entirety.

To denote a humanized antibody, the letters "hu" or "h" appear before the name of the antibody. For example, humanized N901 may be referred to as huN901 or hN901. The sequences for huN901 are disclosed, for example, in U.S. Patent Publication No. 2012/0269827 which is incorporated by reference herein in its entirety. Exemplary N901 sequences are provided below.

```
N901LCv1.1 light chain 1
                                        SEQ ID NO: 6
DVVMTQSPLSLPVTLQPASISCRSSQIIIHSDGNTYLEWFQQRPGQSPRR

LIYKVSNRFSGVPDRFSGSGSGTDFTLKISRVEAEDVGVYYCFQGSHVPH

TFGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC

N901HCv1.1 heavy chain 2
                                        SEQ ID NO: 7
QVQLVESGGGVVQPGRSLRLSCAASGFTFSSFGMHWVRQAPGKGLEWVAY

ISSGSFTIYYADSVKGRFTISRDNSKNTLYLQMNSLRAEDTAVYYCARMR

KGYAMDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK

Other exemplary sequences of human N901 are
provided below:

gN901LCv1.1
                                        SEQ ID NO: 8
DVVMTQSPLSLPVTLGQPASISCRSSQIIIHSDGNTYLEWFQQRPGQSPR

RLIYKVSNRFSGVPDRFSGSGSGTDFTLKISRVEAEDVGVYYCFQGSHVP

HTFGQGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC gN901HCv1.1
                                        SEQ ID NO: 9
QVQLVESGGGVVQPGRSLRLSCAASGFTFSSFGMHWVRQAPGKGLEWVAY

ISSGSFTIYYADSVKGRFTISRDNSKNTLYLQMNSLRAEDTAVYYCARMR

KGYAMDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLEPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK
```

As used herein, the term "alkyl," by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$) alkyl, such as, but not limited to, ethyl, methyl, isopropyl, isobutyl, n-pentyl, n-hexyl and cyclopropylmethyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, such as, but not limited to, ethoxy and methoxy.

"Anti-reduction agent" refers to any small molecule compound that is capable of minimizing reduction of disulfide groups in other molecules, such as antibodies or recombinant proteins. Anti-reduction agents of the present invention are useful to lower the thiol to antibody ratio, minimize disulfide bond reduction of an antibody or fragment thereof, retain intact native disulfide bonds of an antibody or fragment thereof, and/or increase a ratio of non-reduced to reduced antibody, or fragment thereof. Some examples of anti-reduction agents include methylene blue; a quinone such as a substituted benzoquinone; 1,2-naphthoquinone-4-sulfonic acid; anthraquinone-2-sulfonic acid; and a coenzyme Q analog; and a disulfide such as a disulfiram; lipoic acid; a soluble cystine analog; a combination of glutathione reductase and oxidized glutathione (GSSG); and 5,5'-dithiobis(2-nitrobenzoic acid) (DTNB). A substituted benzoquinone can include such structures as represented by formula I:

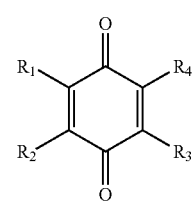

(I)

where $R_1$, $R_2$, $R_3$, and $R_4$ is each independently selected from H, alkyl, alkoxy, COOH, and $SO_3H$. Coenzyme Q analogs include such examples as coenzyme Q0, coenzyme Q2, and combinations thereof. Cystine analogs can include cystine, cystine dimethyl ester, cystine diethyl ester, cystine methyl ester, cystine ethyl ester, di-N-acetyl cystine, cystine bis(t-butyl ester) (CDBE), monoesters of cystine, asymmetric esters of cystine, and any combinations thereof. In one embodiment, the cystine analog is L-cystine bis (t-butyl ester).

By "cell culture" is meant the in vitro growth of cells.

By "cell culture medium" or "cell culture media" is meant a solution used during culturing, growth, or maintenance of a cell. Exemplary cells are mammalian host cells.

As used herein, the term "cystine" refers to a dimer of cysteine or a derivative thereof. Cystines may be asymmetric (i.e., mixed, wherein the two cysteines in the cystine are not identical) or symmetric (i.e., wherein the two cysteines in the cystine are identical). As used herein, a cystine refers to a dimer of two L-cysteines or derivatives thereof, a dimer of two D-cysteines or derivatives thereof, a dimer of one L-cysteine or a derivative thereof and one D-cysteine or a derivative thereof, and any combinations thereof. In certain embodiments, the cystine is a dimer of two L-cysteines or derivatives thereof. In other embodiments, the cystine is a dimer of two D-cysteines or derivatives thereof. In yet other embodiments, the cystine is a dimer of one L-cysteine or a derivative thereof and one D-cysteine or a derivative thereof. In still other embodiments, where the cystine is L-cystine bis(t-butyl) ester (CDBE) or cystine dimethyl ester (CDME) the cystine is not sourced from animals and is transmissible spongiform encephalopathy (TSE) safe. In other embodiments, the cystine is animal-derived cystine dimethyl ester (CDME), but is non-rodent derived and is TSE safe. In still other embodiments, custom synthesis is carried out using non-animal L-cystine.

The term "pre-harvest cell culture fluid" refers to the solution present after cell culture and before cell harvest. A pre-harvest cell culture fluid includes, but is not limited to, cell culture medium to which one or more agents of the invention are optionally added. Pre-harvest marks the beginning of cell harvesting operations when culture conditions are no longer optimized for cell growth. The cell culture media and/or pre-harvest cell culture fluid may contain proteins or antibodies that are released (e.g., secreted) into the media or solution by the cells during culturing. Cell culture media is optimized for cell growth, whereas the pre-harvest and harvest cell culture fluids are optimized for cell separation and antibody purification. For example, the pre-harvest step can include preparation of the culture for harvest by reducing temperature, changing the pH (usually lowering to a pH of about 5 to a pH of less than about 7), adding anti-reduction agents, such as via the pumps that add feed media during culture, and flocculation. The pre-harvest step can be optional as the cell culture media can be pumped directly from the bioreactor where the cells are being cultured to the centrifuge or filter for the harvesting step.

"Harvest cell culture fluid" refers to the solution present during the cell separation process and after separation of the cells from the cell culture media via methods, such as centrifugation or filtration. A harvest cell culture fluid typically includes antibodies or recombinant proteins secreted by the cells during cell culture. A harvest cell culture fluid includes, but is not limited to cell culture medium to which one or more anti-reduction agents of the invention are optionally added.

By "disulfide" is meant a compound with a linked pair of sulfur atoms. Examples of a disulfide include, but are not limited to, disulfiram, lipoic acid, a soluble cystine analog, a combination of glutathione reductase and oxidized glutathione (GSSG), oxidized glutathione alkyl esters (including methyl esters, ethyl esters, and isopropyl esters), and 5,5'-dithiobis(2-nitrobenzoic acid) (DTNB). A "disulfide bond" refers to one or more linked pairs of sulfur atoms or a covalent linkage of two thiol groups in a compound, antibody, or fragment thereof.

By "effective amount" is meant an amount of an anti-reduction agent of the invention sufficient to minimize disulfide bond reduction. Preferably disulfide bond reduction is minimized by at least about 10%, 20%, 25%, 50%, 75%, or by 100%, such that it is virtually undetectable as compared to an untreated sample.

By "fragment" is meant a portion of an antibody, antibody molecule, or protein molecule. This portion contains, preferably, at least 10%, 20%, 30%, 40%, 50%, 60%, 70%, 80%, or 90% of the entire length of the antibody molecule. A fragment may contain 10, 20, 30, 40, 50, 60, 70, 80, 90, or 100, 200, 300, 400, 500, 600, 700, 800, 900, or 1000 amino acids of the antibody.

"Fragmentation" refers to cleavage of the immunoglobulin molecule into fragments or smaller portions than the original expressed molecule. The fragmentation phenomenon can occur during the antibody production process, such as the use of excessive mechanical cell shear that releases reducing agents that reduce the antibody's interchain disulfide bonds during culture or harvest, or proteases that digest or cleave certain portions of the immunoglobulin protein structure. Measurements of fragmentation, such as thiol to antibody ratio, can be visualized on a gel, or by measuring thiol amount in the antibody by Ellman's assay or by an HPLC assay using derivatization of thiol.

By "large scale" or "production scale" is meant 80 L, 200 L, 500 L, 1200 L, 600 L, and 12,000 L and various numbers in between.

By "minimizing a disulfide bond reduction" is meant decreasing the thiol to antibody ratio by more than about 25%, more than about 50%, more than about 75%, more than about 80%, more than about 85%, more than about 90%, more than about 95%, more than about 98%, more than about 99%, or more. Minimizing also refers to decreasing the percentage of fragmentation by more than about 25%, 50%, 75%, 80%, 85%, 90%, 95%, 98%, 99%, or more. Minimizing also refers to decreasing the amount of non-intact antibody, or retaining intact antibody, present at any stage in the purification process by at least about 50% of the total antibody (intact antibody+reduced antibody fragments), at least about 75%, at least about 80%, at least about 85%, at least about 90%, at least about 95%, at least about 98%, at least about 99%, or more. Measurements of minimizing thiol to antibody ratio, decreasing fragmentation, or decreasing non-intact antibody can be assessed from assays such as, for example, quantification of antibody fragmentation on a gel.

By "quinone" is meant oxidized aromatic compounds. For example, some known quinones include substituted benzoquinone; 1,2-naphthoquinone-4-sulfonic acid; and anthraquinone-2-sulfonic acid; coenzyme Q0 and coenzyme Q2-3.

By "reduction" is meant the cleavage of a disulfide bond in a protein, such as an antibody, or fragment thereof by a reducing agent.

By "sparging" is meant the addition of air or dissolved $O_2$ to the cell culture media, pre-harvest cell culture fluid, and/or harvest cell culture fluid to achieve an $O_2$ concentration of at least about 20% to about 100%. Sparging with O$_2$ can include achieving a dissolved concentration of greater than about 20%, or between about 20% to about 100%. Sparging with O$_2$ also includes increasing the percentage of O$_2$ saturation in the cell culture media, pre-harvest cell culture fluid, and/or harvest cell culture fluid to be in a range of about 100% of air saturation (about 20% O$_2$) to about 500% of air saturation (about 100% O$_2$) (e.g., 100%, 110%, 120%, 125%, 130%, 140%, 150%, 160%, 170%, 175%, 180%, 190%, 200%, 225%, 250% air saturation). In other embodiments, air saturation ranges in the cell culture media, pre-harvest cell culture fluid, and/or harvest cell culture fluid are between about 100-125%, 100-150%, 125-150%, 150-200%, and 200-250%.

"Sub-stoichiometric" refers to a molar concentration of the agent that is less than the molar concentration of total thiol in a solution.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The terms "isolated," "purified," or "biologically pure" refers to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, an antibody or fragment thereof is purified if it is substantially free of cellular material, viral material, or culture medium when produced by recombinant techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that the antibody or fragment thereof gives rise to essentially one band in an electrophoretic gel.

By an "isolated antibody or fragment thereof" is meant an antibody or fragment thereof of the invention that has been separated from components that naturally accompany it. Typically, the antibody or fragment thereof is isolated when it is at least 60%, by weight, free from the cellular proteins and naturally-occurring organic molecules with which it is naturally associated. Preferably, the preparation is at least 75%, more preferably at least 90%, and most preferably at least 99%, by weight, an antibody or fragment thereof of the invention. An isolated antibody or fragment thereof of the invention may be obtained, for example, by extraction from a natural source, by recombinant expression; or by chemical synthesis. Purity can be measured by any appropriate method, for example, column chromatography, polyacrylamide gel electrophoresis, or by HPLC analysis.

As used herein, "obtaining" as in "obtaining an agent" includes synthesizing, purchasing, or otherwise acquiring the agent.

The methods of producing the antibody or fragment thereof of the invention in general comprise large scale or production scale of the antibody or fragment thereof, such that the antibody or fragment thereof is a therapeutic antibody or fragment thereof for administration to a subject (e.g., animal, human) in need thereof, including a mammal, particularly a human.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 12A shows results of a non-reducing Protein Lab Chip electrophoresis. FIG. 12B is a table showing the quantitative analysis of antibody fragmentation and intact antibody using a non-reducing Protein Lab Chip analysis. Samples treated at various time points with a combination of AQS and CDME (AQC) are compared to control samples without any AQS or CDME added.

DETAILED DESCRIPTION OF THE INVENTION

Figure 1:
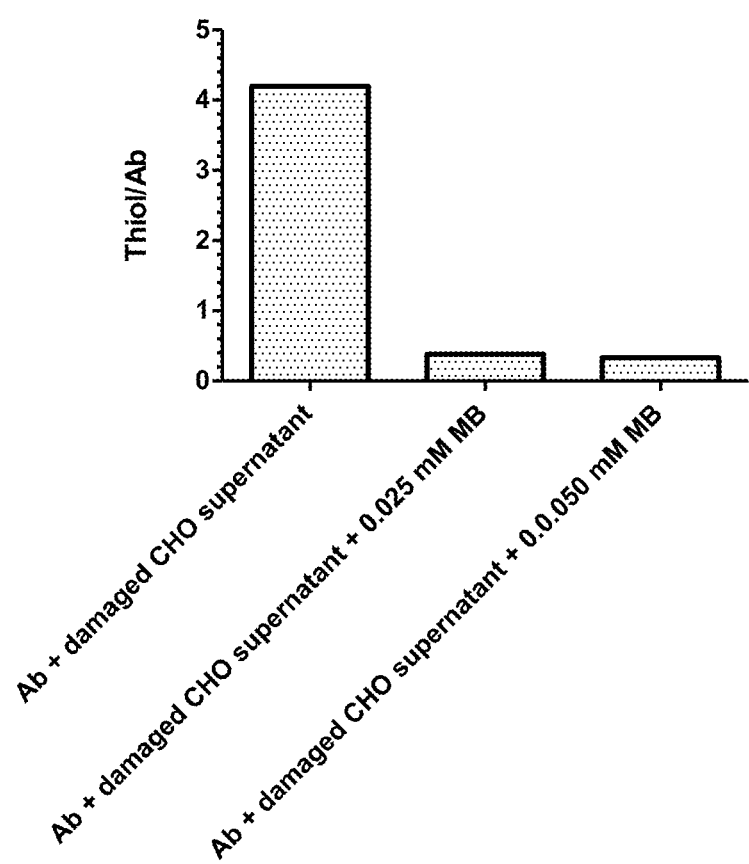
FIG. 1 is a graph that shows treatment of humanized anti-FOLR1 IgG1 antibody with damaged CHO cell supernatant with or without methylene blue (MB) at 0.025 mM and 0.05 mM for 2.2 hours, followed by measurement of thiol per antibody.

As described below, the present invention features compositions and methods for protecting against fragmentation and disulfide bond reduction in antibodies and other recombinant proteins.

The invention is based, at least in part, on the discovery of agents (e.g., methylene blue; a substituted benzoquinone; 1,2-naphthoquinone-4-sulfonic acid; anthraquinone-2-sulfonic acid; lipoic acid; disulfiram; a soluble cystine analog; a combination of glutathione reductase and oxidized glutathione (GSSG); oxidized glutathione alkyl esters (including methyl esters, ethyl esters, and isopropyl esters), and 5,5'-dithiobis(2-nitrobenzoic acid) (DTNB)) that minimize native disulfide bond reduction, thereby increasing the expression and/or production of recombinant proteins, antibodies, or fragments thereof, with intact native disulfide bonds. Such agents are advantageously non-toxic and do not result in the unintended covalent modification of antibodies or recombinant proteins.

Recombinant Protein and/or Antibody Production

The production and purification of antibodies and recombinant proteins typically includes cell separation step that can result in the release of intracellular reducing proteins and peptides containing thiol groups. Such reducing proteins and peptides likely contribute to the undesirable reduction of inter-chain disulfide bonds in antibodies and recombinant proteins. As reported herein below, a number of agents of the invention (e.g., methylene blue; a substituted benzoquinone; 1,2-naphthoquinone-4-sulfonic acid; anthraquinone-2-sulfonic acid; lipoic acid; disulfiram; a soluble cystine analog; a combination of glutathione reductase and oxidized glutathione (GSSG); oxidized glutathione alkyl esters (including methyl esters, ethyl esters, and isopropyl esters), and 5,5'-dithiobis(2-nitrobenzoic acid) (DTNB)) have been identified that minimize the reduction of antibodies and recombinant proteins. These agents can be added to cell culture media, pre-harvest cell culture fluid, and/or harvest cell culture fluid at virtually any point during the expression, production, and/or purification of antibodies or other recombinant proteins, or fragments thereof, in a mammalian host cell.

Such anti-reduction agents (e.g., methylene blue; a substituted benzoquinone; 1,2-naphthoquinone-4-sulfonic acid; anthraquinone-2-sulfonic acid; lipoic acid; disulfiram; a soluble cystine analog; a combination of glutathione reductase and oxidized glutathione (GSSG); oxidized glutathione alkyl esters (including methyl esters, ethyl esters, and isopropyl esters), and 5,5'-dithiobis(2-nitrobenzoic acid) (DTNB)) advantageously minimize or prevent native disulfide bonds reduction, thereby increasing the expression and/or production of antibodies, or fragment thereof, having intact native disulfide bonds. Such anti-reduction agents are particularly advantageous because they do not result in the unintended covalent modification of the antibody, or fragment thereof, and would not increase the immunogenicity of an antibody, or fragment thereof, used for therapeutic purposes. In addition, agents of the invention unexpectedly decrease the extent of disulfide reduction even at concentrations that are below the level of the total thiol in the cell culture media, pre-harvest cell culture fluid, and/or harvest cell culture fluid.

Accordingly, the present invention provides cell culture compositions comprising agents described herein (e.g., methylene blue; a substituted benzoquinone; 1,2-naphthoquinone-4-sulfonic acid; anthraquinone-2-sulfonic acid; lipoic acid; disulfiram; a soluble cystine analog; a combination of glutathione reductase and oxidized glutathione (GSSG); oxidized glutathione alkyl esters (including methyl esters, ethyl esters, and isopropyl esters), and 5,5'-dithiobis (2-nitrobenzoic acid) (DTNB) and combinations thereof) that prevent or minimize protein or antibody reduction. The invention further provides methods of using such cell culture compositions for culturing mammalian host cells that express recombinant proteins, antibodies, or fragments thereof.

Compositions

Compositions of the present invention are useful for minimizing reduction of a disulfide bond in a recombinant protein, antibody or fragment thereof that is expressed in a mammalian host cell. The compositions of the invention include cell culture media, pre-harvest cell culture fluid, and/or harvest cell culture fluid. Such compositions can include aqueous compositions useful in the production of recombinant proteins, such as antibodies. Exemplary cell culture medias are listed in Table 4.

TABLE 4

Cell culture medias.

| Description | Basal/Feed Media | Manufacturer |
|---|---|---|
| CD CHO | Basal Media | Life Technologies |
| CD FortiCHO | Basal Media | Life Technologies |
| CD Efficient Feed A | Feed Media | Life Technologies |
| CD Efficient Feed B | Feed Media | Life Technologies |
| CD Efficient Feed C | Feed Media | Life Technologies |
| ExCell 325 PF | Basal Media | SAFC |

TABLE 4-continued

Cell culture medias.

| Description | Basal/Feed Media | Manufacturer |
|---|---|---|
| ExCell CHOZN Media | Basal Media | SAFC |
| ExCell CHOZN Feed | Feed Media | SAFC |
| Hyclone CDM4CHO | Basal Media | ThermoFisher |
| Hyclone Hycell | Basal Media | ThermoFisher |
| Hyclone CellBoost | Feed Media | ThermoFisher |

The compositions include an agent of the invention, such as an anti-reduction agent, in an amount sufficient to minimize reduction of a disulfide bond. As described herein, the anti-reduction agent includes one or more of the following: methylene blue, a quinone, a disulfide, a salt thereof, and any combinations thereof.

Methylene Blue

Methylene blue is a heterocyclic aromatic chemical compound with a molecular formula of $C_{16}H_{18}N_3SCl$. See Table 1.

TABLE 1

Structural formula of methylene blue.

| Compound | Structural Formula |
|---|---|
| Methylene blue | 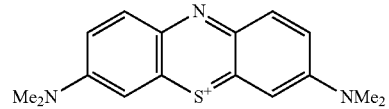 |

Recent studies have found that methylene blue may have a neuroprotective effect. In low doses, methylene blue protects the brain from disease by acting as an antioxidant in the mitochondria. It functions as an alternative mitochondrial electron transfer carrier to enhance cellular oxygen consumption and thus provide neuroprotection in vitro.

Compositions and methods for culturing mammalian host cells that express an antibody or fragment thereof can include methylene blue as an anti-reduction agent in an amount sufficient to minimize reduction of a disulfide bond in the antibody or fragment thereof. In one embodiment, methylene blue can be added to a final concentration in the range of about 0.01 mM to about 100 mM (e.g., 0.01, 0.1, 0.5, 1, 5, 10, 15, 20, 25, 30, 35, 40, 45, 50, 55, 60, 65, 70, 75, 80, 85, 90, 95, 100), about 0.05 mM to about 50 mM, and about 0.1 mM to about 10 mM. In particular embodiments, a composition of the invention (e.g., cell culture media, pre-harvest cell culture fluid, and/or harvest cell culture fluid) comprises about 0.025 and/or about 0.05 mM of methylene blue.

In yet another embodiment, methylene blue can be added at a molar ratio of about 0.01 to about 10 of the total thiol concentration in the cell culture media, pre-harvest cell culture fluid, and/or harvest cell culture fluid, about 0.05 to about 2.5 of the total thiol concentration, about 0.07 to about 1 of the total thiol concentration, and/or about 0.1 to about 0.8 of the total thiol concentration. In another embodiment, methylene blue can be added at sub-stoichiometric concentrations or to a molar concentration of the anti-reduction agent that is less than the molar concentration of total thiol in the cell culture media, pre-harvest cell culture fluid, and/or harvest cell culture fluid.

Quinones

Quinones are oxidized, conjugated compounds that are derived from aromatic compounds, such as benzene or naphthalene. Quinones are electrophilic acceptors that are stabilized by conjugation. They readily react with electron-donating substituents. Depending on the quinone and the site of reduction, reduction can either re-aromatise the quinone or break the conjugation.

Some examples of specific quinones useful as anti-reduction agents in the present invention include, but are not limited to, substituted benzoquinone; 1,2-naphthoquinone-4-sulfonic acid; anthraquinone-2-sulfonic acid; coenzyme Q0, coenzyme Q2-3, a salt thereof, and any combinations thereof. In one particular embodiment, an anti-reduction agent of the invention is a Coenzyme Q analog, such as Q0 (2,3-dimethoxy-5-methyl-p-benzoquinone) or Q2 (2,3-dimethoxy-5-methyl-6-geranyl-p-benzoquinone).

A substituted benzoquinone can include such structures as represented by formula (I):

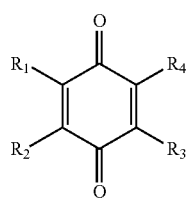

(I)

where $R_1$, $R_2$, $R_3$, and $R_4$ can be each independently selected from the group consisting of H, alkyl, alkoxy, COOH, and $SO_3H$. Coenzyme Q analogs can include such examples as coenzyme Q0, coenzyme Q2, and combinations thereof. See Table 2 for structural formulas.

In one embodiment, the quinone is anthraquinone-2-sulfonic acid and is effective at lowering the antibody disulfide reduction.

| Quinone structural formulas. | |
|---|---|
| Compound | Structural Formula |
| Substituted benzoquinone | 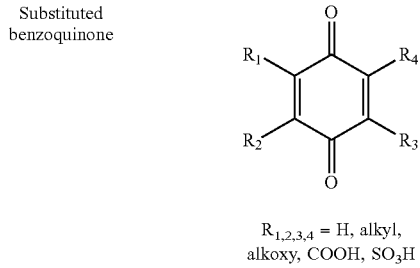<br>$R_{1,2,3,4}$ = H, alkyl, alkoxy, COOH, $SO_3H$ |
| Coenzyme Q0 | 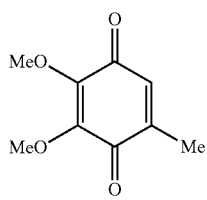 |

| Quinone structural formulas. | |
|---|---|
| Compound | Structural Formula |
| Coenzyme Q2 | ![structure] <br> n = 2 |
| 1,2-Naphthoquinone-4-sulfonic acid | ![structure] |
| Anthraquinone-2-sulfonic acid | ![structure] |

Compositions and methods for culturing mammalian host cells that express an antibody or fragment thereof can include one or more quinones as an anti-reduction agent in an amount sufficient to minimize reduction of a disulfide bond in the antibody or fragment thereof. In one embodiment, a quinone can be added to a final concentration in the range of about 0.01 mM to about 100 mM (e.g., 0.01, 0.1, 0.5, 1, 5, 10, 15, 20, 25, 30, 35, 40, 45, 50, 55, 60, 65, 70, 75, 80, 85, 90, 95, 100), about 0.05 mM to about 50 mM, and about 0.1 mM to about 10 mM. In particular embodiments, Q0 or Q2 (2,3-dimethoxy-5-methyl-6-geranyl-p-benzoquinone) is added to a final concentration of about 0.2 or 0.1 mM.

In yet another embodiment, a quinone can be added at a molar ratio of about 0.01 to about 10 of the total thiol concentration in the cell culture media, pre-harvest cell culture fluid, and/or harvest cell culture fluid, about 0.05 to about 2.5 of the total thiol concentration, about 0.07 to about 1 of the total thiol concentration, and about 0.1 to about 0.8 of the total thiol concentration.

Disulfides

Disulfides are compounds containing a linked pair of sulfur atoms or a disulfide bond. Examples of disulfides include disulfiram; lipoic acid; a soluble cystine analog; a combination of glutathione reductase and oxidized glutathione (GSSG); oxidized glutathione alkyl esters (including methyl esters, ethyl esters, and isopropyl esters); 5,5'-dithiobis(2-nitrobenzoic acid) (DTNB), a salt thereof, and any combinations thereof. Cystine analogs are also disulfides and include cystine dimethyl ester, cystine diethyl ester, cystine bis(t-butyl) ester, cystine methyl ester, cystine ethyl ester, cystine t-butyl ester, di-N-acetyl cystine, L-cystine bis(t-butyl ester), monesters of cystine, asymmetric esters of cystine, and any combinations thereof. The disulfides useful within the invention may also include symmetric and asymmetric disulfides of the sulfides recited herein. See Table 3 for disulfide structural formulas.

TABLE 3

Disulfide structural formulas.

| Compound | Structural Formula |
| --- | --- |
| Cystine dimethyl ester | MeOOC-CH(NH$_3^+$)-CH$_2$-S-S-CH$_2$-CH(NH$_3^+$)-COOMe |
| Cystine diethyl ester | EtOOC-CH(NH$_3^+$)-CH$_2$-S-S-CH$_2$-CH(NH$_3^+$)-COOEt |
| Cystine bis(t-butyl) ester | (H$_3$C)$_3$C-OOC-CH(NH$_3^+$)-CH$_2$-S-S-CH$_2$-CH(NH$_3^+$)-COO-C(CH$_3$)$_3$ |
| Cystine methyl ester | HOOC-CH(NH$_3^+$)-CH$_2$-S-S-CH$_2$-CH(NH$_3^+$)-COOMe |
| Cystine ethyl ester | HOOC-CH(NH$_3^+$)-CH$_2$-S-S-CH$_2$-CH(NH$_3^+$)-COOEt |
| Cystine t-butyl ester | HOOC-CH(NH$_3^+$)-CH$_2$-S-S-CH$_2$-CH(NH$_3^+$)-COO-C(CH$_3$)$_3$ |
| L-cystine bis(t-butyl ester) | (H$_3$C)$_3$CO-CO-CH(NH$_3^+$)-CH$_2$-S-S-CH$_2$-CH(NH$_3^+$)-CO-OC(CH$_3$)$_3$ |
| Di-N-acetylcystine | HOOC-CH(NHAc)-CH$_2$-S-S-CH$_2$-CH(NHAc)-COOH |
| Lipoic acid | 1,2-dithiolane-3-yl-(CH$_2$)$_4$-COOH |

TABLE 3-continued

Disulfide structural formulas.

| Compound | Structural Formula |
|---|---|
| Oxidized glutathione alkyl esters | [structure] |
| Disulfiram (Tetraethylthiuram disulfide) | $NEt_2-C(=S)-S-S-C(=S)-NEt_2$ |
| 5,5'-Dithiobis(2-nitrobenzoic acid) | [structure] |

Disulfiram is commonly used as a treatment for chronic alcoholism by blocking the processing of alcohol in the body by inhibiting acetaldehyde dehydrogenase. Lipoic acid is a strained 5-member cyclic disulfide. Cystine dimethyl ester (CDME) is a soluble, non-toxic disulfide that is typically used to prevent kidney stones. The disulfides possess high potential to be reduced and can thereby protect disulfide bonds in recombinant proteins, antibodies or fragments thereof. Lipoic acid contains a strained 5-membered cyclic disulfide (S. Sunner, Nature, 176, 217, 1955). The strained cyclic disulfide group in lipoic acid is unexpectedly more reactive toward thiol than non-cyclic disulfides, which would favor the reduction of lipoic acid by CHO cell thiol proteins in comparison to antibody disulfide bonds. Oxidized glutathione alkyl esters (including methyl esters, ethyl esters, and isopropyl esters), both symmetric and asymmetric, are also useful to protect disulfide bonds in recombinant proteins, antibodies or fragments thereof.

Disulfides are also useful anti-reduction agents for their unexpected solubilities in water, in particular cystine dimethyl ester dihydrochloride, cystine diethyl ester dihydrochloride, and cystine bis(t-butyl) ester. In one embodiment, cystines useful within the invention comprise L-cystine dimethyl ester dihydrochloride, L-cystine diethyl ester dihydrochloride, L-cystine bis(t-butyl) ester, cystine dimethyl ester, or any combinations thereof. Compositions and methods for culturing mammalian host cells that express an antibody or fragment thereof can include one or more disulfides as an anti-reduction agent in an amount sufficient to minimize reduction of a disulfide bond in the antibody or fragment thereof. The disulfide can be added to a final concentration in the range of about 0.01 mM to about 100 mM (e.g., 0.01, 0.1, 0.5, 1, 2, 2.5, 5, 10, 15, 20, 25, 30, 35, 40, 45, 50, 55, 60, 65, 70, 75, 80, 85, 90, 95, 100), about 0.05 mM to about 50 mM, and about 0.1 mM to about 10 mM.

Inorganic and Organic Redox Active Substances

Certain inorganic and organic redox active substances are also useful anti-reduction agents. These redox active substances can be used to modulate the redox potential of cell culture media, pre-harvest cell culture fluid, or harvest cell culture fluid to protect antibodies from disulfide reduction. These substances have an aptitude to accept electrons greater than the redox potential of inter- and intrachain disulfide bonds. As a result, they can neutralize reduction equivalents. Such substances include, but are not limited to, $ZnSO_4$, $CuSO_4$, $NiSO_4$, $NaNO_3$, and any combinations thereof. These substances can be added to a final concentration in the range of about 0.01 mM to about 100 mM (e.g., 0.01, 0.1, 0.5, 1, 2, 2.5, 5, 10, 15, 20, 25, 30, 35, 40, 45, 50, 55, 60, 65, 70, 75, 80, 85, 90, 95, 100), about 0.05 mM to about 50 mM, and about 0.1 mM to about 10 mM.

In one embodiment, the final concentration of one or more anti-reduction agents can be at least about 0.001 mM, 0.005 mM, 0.01 mM, 0.015 mM, 0.02 mM, 0.025 mM, 0.03 mM, 0.035 mM, 0.04 mM, 0.045 mM, 0.05 mM, 0.055 mM, 0.06 mM, 0.065 mM, 0.07 mM, 0.075 mM, 0.08 mM, 0.085 mM, 0.09 mM, 0.095 mM, 0.1 mM, 0.15 mM, 0.2 mM, 0.25 mM, 0.3 mM, 0.35 mM, 0.4 mM, 0.45 mM, 0.5 mM, 0.7 mM, 1.0 mM, 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, 100 mM, and any concentration in between. In another embodiment, one or more anti-reduction agents can be added to a final concentration in the range of about 0.01 mM to about 100 mM, about 0.05 mM to about 50 mM, and about 0.1 mM to about 10 mM. In a particular embodiment, one or more of the anti-reduction agents is added at a sub-stoichiometric concentration. In another embodiment, the anti-reduction agent is at a concentration of less than about 10 mM.

In yet another embodiment, one or more anti-reduction agents can be added at a molar ratio of about 0.01 to about 10 of the total thiol concentration in the cell culture media, pre-harvest cell culture fluid, and/or harvest cell culture fluid, about 0.05 to about 2.5 of the total thiol concentration, about 0.07 to about 1 of the total thiol concentration, and about 0.1 to about 0.8 of the total thiol concentration.

In another embodiment, one or more anti-reduction agents can be added at a molar ratio of about 0.001, 0.005, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.3, 0.35, 0.4, 0.45, 0.5, 0.7, 0.8, 0.9, and 1.0 of the total thiol concentration in the cell culture media, pre-harvest cell culture fluid, and/or harvest cell culture fluid.

The anti-reduction agents are also useful to lower a thiol:antibody ratio. The thiol:antibody ratio for the antibody or fragment thereof can be lowered in the presence of anti-reduction agent by at least about 10%, 15%, 20%, 25%, 30%, 35%, 40%, 45%, 50%, 55%, 60%, 70% or more than in the absence of the agent. In one particular embodiment, the antibody or fragment thereof has a thiol:antibody ratio of at least about 25% lower in the presence of the anti-reduction agent than in the absence of the anti-reduction agent. In another particular embodiment, the antibody or fragment thereof has a thiol:antibody ratio of at least about 50% lower in the presence of the anti-reduction agent than in the absence of the anti-reduction agent.

The ratio of non-reduced to reduced antibody or fragment thereof that is produced by a mammalian host cell is increased by adding a sufficient amount of an anti-reduction agent to a cell culture media, pre-harvest cell culture fluid, and/or harvest cell culture fluid. The ratio can be increased by at least about 1.5 fold, 2 fold, 2.5 fold, 3 fold, 3.5 fold, 4 fold, 4.5 fold, 5 fold, 5.5 fold, 6 fold, 6.5 fold, 7 fold, 7.5 fold, 8 fold, 8.5 fold, 9 fold, 9.5 fold, 10 fold, 12 fold, 15 fold, 17 fold, or more. In one embodiment, the ratio is increased by at least about 2-fold. In another embodiment, the ratio is increased by at least about 10-fold.

As described above, the anti-reduction agent can include a combination of methylene blue, one or more quinones, and/or one or more disulfides. In a particular embodiment, the composition includes a mixture of anthraquinone-2-sulfonic acid and cystine dimethyl ester; a mixture of lipoic acid and anthraquinone-2-sulfonic acid; or a mixture of lipoic acid and cystine dimethyl ester.

It is also useful that the anti-reduction agent does not covalently modify the antibody or fragment thereof. Covalent modification could increase the immunogenicity of antibody and could also adversely affect the physicochemical behavior of the antibody. Thus, after treatment with the anti-reduction agent of the invention, the antibody or fragment thereof substantially possesses its native folded structure and retains its antigen binding site without alteration.

Also useful are anti-reduction agents that do not detectably or substantially decrease viability of the host cells. In one embodiment, the anti-reduction agent of the present invention does not decrease viability by greater than about 30%, 25%, 20%, 15%, 10%, 9%, 8%, 7%, 6%, 5%, 4%, 3%, 2%, or less. In one embodiment, the anti-reduction agent does not decrease viability of the cells by greater than about 15%.

The compounds useful within the invention may possess one or more stereocenters, and each stereocenter may exist independently in either the (R) or (S) configuration. In one embodiment, compounds described herein are present in optically active or racemic forms. The compounds described herein encompass racemic, optically active, regioisomeric and stereoisomeric forms, or combinations thereof that possess the useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized in the composition described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods described herein include the use of crystalline forms (also known as polymorphs), solvates, amorphous phases, and/or acceptable salts of compounds having the structure of any compound useful within the invention, as well as derivatives thereof having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with acceptable solvents such as water, and ethanol. In another embodiment, the compounds described herein exist in unsolvated form.

In one embodiment, the compounds of the invention may exist as tautomers. All tautomers are included within the scope of the compounds presented herein.

The compounds described herein may form salts with acids or bases, and such salts are included in the present invention. The term "salts" embraces addition salts of free acids and addition salts of free bases that are useful within the methods of the invention.

Suitable acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable acceptable base addition salts of compounds of the invention include, for example, metallic salts including alkali metal, alkaline earth metal and transition metal salts such as, for example, calcium, magnesium, potassium, sodium and zinc salts. Acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

Antibody Production

Described herein are methods for minimizing disulfide bond reduction or fragmentation of an antibody or fragment thereof that is expressed in a mammalian host cell. As disulfide bond reduction and fragmentation can occur during multiple stages of the antibody production process, the methods described herein address these issues by adding a sufficient amount of an anti-reduction agent to a cell culture media, pre-harvest cell culture fluid, and/or harvest cell culture fluid.

In one aspect, a method is provided for minimizing disulfide bond reduction in an antibody or fragment thereof that is expressed in a mammalian host cell includes adding a composition comprising one or more agents of the invention (e.g., methylene blue; a substituted benzoquinone; 1,2-naphthoquinone-4-sulfonic acid; anthraquinone-2-sulfonic acid; lipoic acid; disulfiram; a soluble cystine analog; a combination of glutathione reductase and oxidized glutathione (GSSG); and 5,5'-dithiobis(2-nitrobenzoic acid) (DTNB)) to a cell culture media, pre-harvest cell culture fluid, and/or harvest cell culture fluid. The anti-reduction agent is one or more of methylene blue, a quinone, a disulfide, a salt thereof and any combinations thereof.

In another aspect, a method is provided for increasing production of an antibody or fragment thereof with intact native disulfide bonds that is expressed in a mammalian host cell. The method includes adding a sufficient amount of an anti-reduction agent to a cell culture media, pre-harvest cell culture fluid, and/or harvest cell culture fluid, where the anti-reduction agent is at least one of methylene blue, a quinone, a disulfide, a salt thereof, and any combinations thereof.

In yet another aspect, a method of increasing a ratio of non-reduced to reduced antibody or fragment thereof that is produced by a mammalian host cell is described. The method includes adding a sufficient amount of an anti-reduction agent, such as one or more of methylene blue, a quinone, a disulfide, a salt thereof, and any combinations thereof, to a cell culture media, pre-harvest cell culture fluid, and/or harvest cell culture fluid. In one embodiment, the method increases the ratio by at least about 2-fold. In another embodiment, the ratio is increased by at least about 10-fold.

The methods provide for adding the anti-reduction agent at various stages in the production process. In one embodiment, the anti-reduction agent is added to the cell culture medium. The anti-reduction agent can be added within about 15 minutes of harvesting the cell culture, about 30 minutes, 45 minutes, 60 minutes, 75 minutes, 90 minutes, 105 minutes 2 hours, 4 hours, 6 hours, 8 hours, 12 hours, 18 hours, 24 hours, 36 hours, 48 hours, or any time point in between. In a particular embodiment, the anti-reduction agent is added to the cell culture medium within 48 hours of harvesting the cell culture. In another particular embodiment, the anti-reduction agent is added to the cell culture medium within 24 hours of harvesting the cell culture. In yet another particular embodiment, the anti-reduction agent is added to the cell culture medium within 12 hours of harvesting the cell culture.

In another embodiment, the anti-reduction agent is added to the pre-harvest cell culture fluid. In yet another embodiment, the anti-reduction agent is added to the harvest cell culture fluid.

The methods also provide for anti-reduction agents that do not substantially decrease viability of the host cells. Adding the anti-reduction agent does not decrease viability by greater than about 30%, 25%, 20%, 15%, 10%, 9%, 8%, 7%, 6%, 5%, 4%, 3%, 2%, or less. In one embodiment, adding the anti-reduction agent does not decrease viability of the cells by greater than about 15%.

Any mammalian host cell can be used with the methods and compositions described herein. Some examples include Chinese hamster ovary (CHO) cells, SP2/0, and NS0 cells.

In one embodiment, the antibody or fragment thereof includes an IgG1, IgG2, IgG3, and IgG4 isotype antibody. In another embodiment, the antibody or fragment thereof is an anti-FOLR1 antibody, an anti-CD56 antibody, an anti-CD37 antibody, an anti-EGFR antibody, an anti-IGF-1 receptor antibody, anti-muc1 (e.g., DS6-humanized or mouse), which is described in WO2005/009369 and WO2007/024222, each of which is incorporated herein by reference in its entirety, an anti-CA6 glycotope antibody, an anti-CD19 (e.g., B4 antibody (huB4 antibody), or an anti-CD33 antibody. Such antibodies are described in International Application Nos.: WO2004/043344, WO2003/106621, WO2005/061541, WO2011/112978, WO2012/058592, and WO2012/058588A2, which are incorporated by reference herein.

In one embodiment, an anti-FOLR1 antibody is an antibody that is capable of binding FOLR1 with sufficient affinity such that the antibody is useful as a diagnostic and/or therapeutic agent in targeting FOLR1. The extent of binding of an anti-FOLR1 antibody to an unrelated, non-FOLR1 protein is less than about 10% of the binding of the antibody to FOLR1 as measured, e.g., by a radioimmunoassay (MA) or ELISA. Anti-FOLR1 antibodies are known in the art and are disclosed, for example, in U.S. Pat. No. 8,557,966 and US Appl. Pub. Nos. 2012/0282175 and 2012/0009181, each of which is herein incorporated by reference in its entirety.

The full-length amino acid (aa) and nucleotide (nt) sequences for FOLR1 are known in the art and are provided below:

```
human folate receptor 1 amino acid sequence
                                         SEQ ID NO: 1
MAQRMTTQLLLLLVWVAVVGEAQTRIAWARTELLNVCMNAKHHKEKPGPE

DKLHEQCRPWRKNACCSTNTSQEAHKDVSYLYRFNWNHCGEMAPACKRHF

IQDTCLYECSPNLGPWIQQVDQSWRKERVLNVPLCKEDCEQWWEDCRTSY

TCKSNWHKGWNWTSGFNKCAVGAACQPFHFYFPTPTVLCNEIWTHSYKVS

NYSRGSGRCIQMWFDPAQGNPNEEVARFYAAAMSGAGPWAAWPFLLSLAL

MLLWLLS human folate receptor 1 nucleic acid sequence
                                         SEQ ID NO: 2
atggctcagcggatgacaacacagctgctgctccttctagtgtgggtggc tgtagtaggggaggctcagacaaggattgcatgggccaggactgagcttc tcaatgtctgcatgaacgccaagcaccacaaggaaaagccaggccccgag gacaagttgcatgagcagtgtcgaccctggaggaagaatgcctgctgttc taccaacaccagccaggaagcccataaggatgtttcctacctatatagat tcaactggaaccactgtggagagatggcacctgcctgcaaacggcatttc atccaggacacctgcctctacgagtgctcccccaacttggggccctggat ccagcaggtggatcagagctggcgcaaagagcgggtactgaacgtgcccc tgtgcaaagaggactgtgagcaatggtgggaagattgtcgcacctcctac acctgcaagagcaactggcacaagggctggaactggacttcagggtttaa
```

```
caagtgcgcagtgggagctgcctgccaacctttccatttctacttcccca cacccactgttctgtgcaatgaaatctggactcactcctacaaggtcagc aactacagccgagggagtggccgctgcatccagatgtggttcgacccagc ccagggcaacccaatgaggaggtggcgaggttctatgctgcagccatga gtggggctgggccctgggcagcctggcctttcctgcttagcctggcccta atgctgctgtggctgctcagc
```

A specifically useful antibody for detection of FOLR1 is the mouse monoclonal anti-huFOLR1 clone BN3.2 (Leica # NCL-L-FRalpha). An example of a therapeutically effective anti-FOLR1 antibody is huMov19 (M9346A). The polypeptides of SEQ ID NOs: 3-5 comprise the variable domain of the heavy chain of huMov19 (M9346A), and the variable domain light chain version 1.00, the variable domain light chain version 1.60 of huMov19, respectively. In certain embodiments, the huMov19 (M9346A) antibody is encoded by the plasmids deposited with the American Type Culture Collection (ATCC), located at 10801 University Boulevard, Manassas, Va. 20110 on Apr. 7, 2010 under the terms of the Budapest Treaty and having ATCC deposit nos. PTA-10772 and PTA-10773 or 10774. Also included are any of the anti-FOLR1 antibodies described in U.S. Provisional Application No. 61/875,475, filed on Sep. 9, 2013. In an exemplary embodiment, the 353-2.1 antibody is included as described therein.

In another particular embodiment, the anti-CD56 antibody is huN901. The CD56 antigen is a neural cell adhesion molecule (NCAM) that is expressed on the surface of tumor cells of neuroendocrine origin, including small cell lung carcinomas (SCLC), carcinoid tumors and Merkel cell carcinomas (MCC). CD56 is expressed on approximately 56% of ovarian tumors. See, e.g., Whiteman, K. R. et. al., AACR Annual Meeting, Abstract No. 2135, "Preclinical Evaluation of IMGN901 (huN901-DM1) as a Potential Therapeutic for Ovarian Cancer" (April 2008). CD56 is also expressed on approximately 70% of multiple myelomas. See, e.g., Tassone, P. et al., Cancer Res. 64:4629-4636 (2004).

The preparation of different versions of humanized N901, is described, for example, by Roguska et al, Proc. Natl. Acad. Sci. USA, 91:969-973 (1994), and Roguska et al, Protein Eng., 9:895:904 (1996), the disclosures of which are incorporated by reference herein in their entirety. In particular embodiments, an humanized N901 antibody comprises or consists of a sequence described in Roguska supra. To denote a humanized antibody, the letters "hu" or "h" appear before the name of the antibody. For example, humanized N901 may be referred to as huN901 or hN901. The sequences for huN901 are disclosed, for example, in U.S. Patent Publication No. 2012/0269827 which is incorporated by reference herein in its entirety.

Sparging

Sparging is a technique of infusing, such as bubbling, gas through a liquid. A gas can be introduced into the liquid in the form of small bubbles. The sparging device is typically fabricated with small apertures through which gas is injected into the liquid, to provide a relatively fine dispersion of gas bubbles in the liquid undergoing treatment. In some systems, the sparger can be positioned at the bottom of the culture so that the small gas bubbles rise slowly through the liquid to provide an extended period of gas-liquid contact.

The present invention includes sparging the cell culture media, pre-harvest cell culture fluid, and/or harvest cell culture fluid with oxygen, $O_2$. In one aspect, a method of minimizing disulfide bond reduction in an antibody or fragment thereof that is expressed in a mammalian host cell is provided. The method includes culturing the host cell in a concentration of at least about 20% dissolved $O_2$.

Unlike methods that sparge with air, which can achieve only minimal $O_2$ concentrations dissolved in the culture media, it has been discovered that high $O_2$ concentrations are important for preserving disulfide bonds and/or minimizing reduction of antibodies during the production process. Thus, sparging with $O_2$ or a combination of air supplemented with $O_2$ can achieve optimal concentrations of dissolved $O_2$, higher than those obtained with air sparging, to reduce and/or prevent antibody fragmentation. In one embodiment, the dissolved $O_2$ concentration in the cell culture media, pre-harvest cell culture fluid, and/or harvest cell culture fluid is in the range of at least about 20% to about 100% $O_2$.

The percentage of $O_2$ saturation in the cell culture media, pre-harvest cell culture fluid, and/or harvest cell culture fluid can be in a range of about 100% of air saturation (about 20% $O_2$) to about 500% of air saturation (about 100% $O_2$) via sparging with $O_2$ gas. The percentage of $O_2$ saturation can be in a range of about 100 to about 125%, about 100 to about 150%, about 125 to about 150%, about 150 to about 200%, about 200 to about 250%, about 250 to about 300%, about 300 to about 350%, about 350 to about 400%, about 400 to about 450%, and about 450% to about 500% of air saturation. The percentage of $O_2$ saturation in the cell culture media, pre-harvest cell culture fluid, and/or harvest cell culture fluid can be about 100%, 110%, 120%, 125%, 130%, 140%, 150%, 160%, 170%, 175%, 180%, 190%, 200%, 225%, 250%, 375%, 400%, 425%, 450%, 475%, and about 500% of air saturation.

The use of sparging with $O_2$ can also be combined with the addition of anti-reduction agents. In one embodiment, methods are included for minimizing disulfide bond reduction in an antibody or fragment thereof by adding a sufficient amount of one or more anti-reduction agents to a cell culture media, pre-harvest cell culture fluid, and/or harvest cell culture fluid and culturing the host cell in a concentration of at least about 20% dissolved $O_2$.

Sparging with $O_2$ can also be employed on a large scale or production scale to reduce fragmentation and/or minimize reduction of antibodies or fragments thereof during the large scale production process.

Therapeutic Antibodies or Fragments Thereof

In one aspect, a method is described for producing a therapeutic antibody, or fragment thereof, by exposing a mammalian host cell that produces the therapeutic antibody, or fragment thereof, to a composition that includes an anti-reduction agent of the invention in a cell culture media, pre-harvest cell culture fluid, and/or harvest cell culture fluid, wherein the anti-reduction agent is at least one of methylene blue, a quinone, and a disulfide.

In another aspect, a method is provided for producing a therapeutic antibody, or fragment thereof, by exposing a mammalian host cell that produces the therapeutic antibody, or fragment thereof, to a concentration of at least about 20% $O_2$. The $O_2$ concentration can be achieved via $O_2$ sparging as described herein.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991); and "Antibodies: A Laboratory Manual" (Harlow and Lane, 1988). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Antibodies and other proteins are often expressed recombinantly. In one embodiment, a vector encoding an antibody or protein of interest is transferred to a host cell by conventional techniques and the transfected cells are then cultured to produce the antibody or recombinant protein. During the course of antibody production, cell damage can occur, particularly during the cell-separation process. This damage can be simulated by methods that disrupt cells. For example, by exposing cells to multiple freeze-thaw cycles, by chemical means, for example, by exposing the cells to detergents, or by mechanical means, for example, using a microfluidizer.

For all of the examples described below, cell damage was simulated by multiple freeze-thaw cycles of cells, by addition of RIPA buffer (50 mM Tris-HCl, pH 7.4, 1% NP-40, 0.5% sodium deoxycholate, 0.1% sodium dodecylsulfate), or by using microfluidizer. This damaged cell supernatant or lysate was then incubated with a buffered solution containing antibody with or without the anti-reduction agent being tested, following which the extent of the antibody-disulfide reduction was measured using Ellman's assay for thiol (P. W. Riddles, R. L. Blakeley, and B. Zerner, Methods Enzymol., 91, 49-60, 1983) or by non-reducing SDS protein LabChip analysis. The total thiol level present in the mixture of damaged cell supernatant/lysate was measured initially. Unexpectedly, several substances were found to lower the antibody-disulfide reduction even upon addition at levels below the level of the total thiol present in the mixture of the damaged cell supernatant/lysate and antibody.

Example 1: Methylene Blue Decreased Antibody Disulfide Bond Reduction

A simulated, damaged CHO cell suspension was prepared using 300 million CHO cells per ml phosphate buffered saline (PBS), which was subjected to three freeze-thaw cycles under vacuum, followed by pelleting of cell debris by centrifugation, and storage of the supernatant at −80° C.

The concentration of thiol in the suspension of damaged CHO cells was measured as 4 mM using DTNB ((5,5′-dithiobis(2-nitrobenzoic acid); Ellman's reagent). Humanized anti-folate receptor 1 (FOLR1) IgG1 (1 mg) was immobilized on 0.05 ml of Protein A bead (RepliGen) and then treated with pre-mixed 0.5 ml PBS and 0.1 ml damaged CHO cell supernatant. The concentration of thiol in this mixture was 0.67 mM.

The sample was rotated for about 2.2 hours at ambient temperature, following which the supernatant was removed and the beads were washed with PBS four times (1.5 ml each). The thiol content of the immobilized antibody on the beads was then analyzed by the addition of 0.6 ml of PBS containing 0.5 mM DTNB, rotation for about 10 minutes, centrifugation, and measurement of the absorbance of the supernatant at 412 nm.

The number of thiol residues per antibody molecule after incubation with damaged CHO cell supernatant was calculated as 4.2 thiol/antibody. A similar value of thiol/antibody was measured using another humanized IgG1 antibody, huN901, incubated with the damaged CHO cell supernatant, suggesting that the mechanism for the reduction of disulfide bonds in IgG1 molecules by the damaged CHO cell supernatant is general and not specific to a particular IgG1.

Methylene blue was then tested at different concentrations to determine whether it could protect against disulfide bond reduction during the incubation of antibody with damaged CHO cell supernatant. FIG. 1 is a graph showing the results of immobilized 1 mg humanized IgG1 with pre-mixed 0.5 ml PBS and 0.1 ml damaged CHO cell supernatant in the presence of methylene blue, rotation for 2.2 hours at ambient temperature, and a similar thiol analysis of immobilized antibody as above. Unexpectedly, very low concentrations of methylene blue (0.025 and 0.05 mM) protected against the reduction of antibody disulfide bonds. Surprisingly, these concentrations were significantly lower than that of thiol (0.67 mM) in the mixture of PBS and damaged CHO cell supernatant.

As shown in FIG. 1, only 0.38 and 0.33 thiol per antibody were detected in the antibody samples containing mixtures of damaged CHO cell supernatant with methylene blue (0.025 mM and 0.05 mM respectively) after 2.2 hours of incubation, in contrast to the 4.2 thiol per antibody detected in the antibody sample containing damaged CHO supernatant only (without methylene blue) after 2.2 hours of incubation.

In a similar experiment, a sample containing 1 mg immobilized antibody was incubated with a mixture of damaged CHO cell supernatant and 0.05 mM methylene blue for 2.2 hours, followed by washing of beads as above, after which the antibody was eluted from Protein A bead using 100 mM acetic acid containing 150 mM NaCl, neutralized to pH 7 by addition of 1.25 M $KH_2PO_4$ solution. Using an aliquot of the neutralized eluted antibody sample, the thiol per antibody was measured as 0.002 thiol per antibody using DTNB, thus indicating the protection against antibody disulfide reduction by methylene blue.

In addition to the finding that methylene blue protects against antibody disulfide reduction, it was unexpectedly found that methylene blue offered protection from antibody disulfide reduction at lower, sub-stoichiometric concentrations (0.025 mM and 0.05 mM) compared to the concentration of total thiol in the CHO supernatant/PBS mixture (0.67 mM).

It is also useful that the anti-reduction agent added to protect the disulfide bonds in antibody from reduction by the reducing proteins in the damaged cell supernatant does not covalently modify the antibody at thiol residues. Covalent modification of thiol residues derived from reduction of native inter-chain disulfides could increase the immunogenicity of antibody and could also adversely affect the physicochemical behavior of the antibody.

To assess if there was any covalent modification of the antibody upon addition of methylene blue, the absorbance of methylene blue-treated anti-FOLR1 IgG1 was monitored at the absorbance maxima of methylene blue (610 nm). The molecular weight of the antibody was assessed by mass spectrometry. The eluted neutralized antibody sample described above (following methylene blue treatment) did not show blue color and had an absorbance of 0.000 at 610 nm, which is the absorbance maxima for methylene blue (extinction coefficient, 610 nm=8800 M-1 cm-1), suggesting that methylene blue did not covalently modify the antibody.

Figure 2:
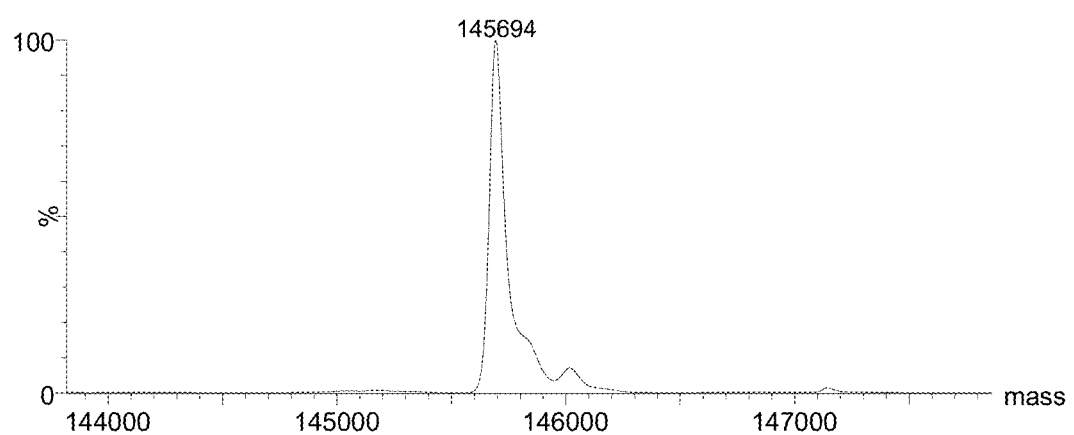
FIG. 2 shows the mass spectrum of a deglycosylated, humanized antibody sample upon treatment with 0.05 mM methylene blue and damaged CHO cell supernatant for 2.2 hours.

Another aliquot of the eluted neutralized antibody was deglycosylated and analyzed by mass spectrometry. As shown in FIG. 2, the antibody sample that was treated with 0.05 mM methylene blue showed a major mass peak at 145694, which was similar to that of the untreated antibody, suggesting that methylene blue treatment did not lead to the modification of the antibody.

Example 2: Coenzyme Q Analogs Decreased Antibody Disulfide-Reduction

Figure 3:
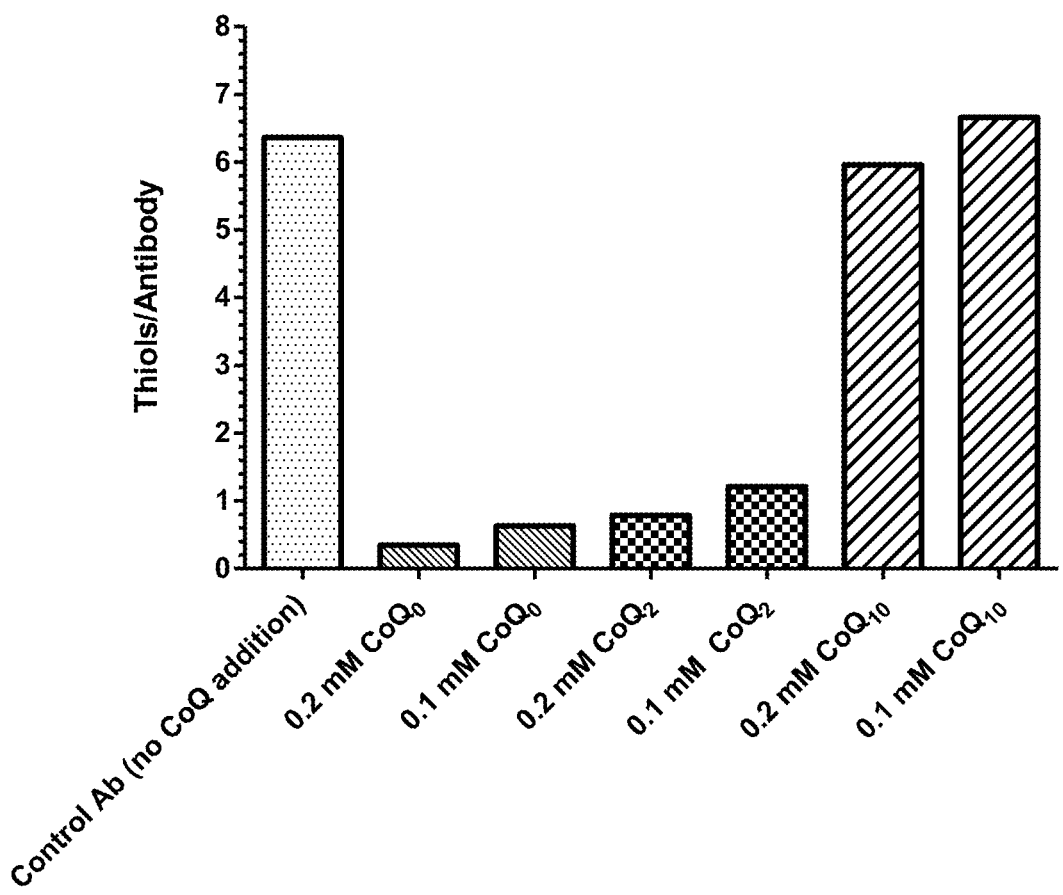
FIG. 3 is a graph that shows the effect of coenzyme Q analogs, which protect against the reduction of disulfide bonds in humanized N901 IgG1 by damaged CHO cell lysate.

Coenzyme Q analogs were tested at different concentrations to determine whether they had a protective effect on disulfide reduction during the incubation of antibody with damaged CHO cell supernatant (FIG. 3). Humanized N901 (Anti-CD56 IgG1; 1 mg) was immobilized on 0.05 ml of Protein A bead (RepliGen) and then treated with pre-mixed 0.4 ml PBS and 0.1 ml damaged CHO cell supernatant (described in Example 1) with or without the addition of coenzyme Q analogs. The concentration of thiol in these mixtures was 0.8 mM.

The samples were rotated for about 1.5 hours at ambient temperature, following which the supernatant was removed and the beads washed with PBS three times. The thiol content of the immobilized antibody on the beads was then analyzed by the addition of 0.6 ml of mixture of PBS and 0.5 mM DTNB, rotation for about 10 minutes, centrifugation, and measurement of the absorbance of the supernatant at 412 nm. The number of thiol residues per antibody molecule after incubation with damaged CHO cell supernatant (without any coenzyme Q analog) was measured as 6.4 thiol/antibody.

In contrast, as shown in FIG. 3, the co-incubation of antibody and damaged CHO supernatant with coenzyme Q0 (2,3-dimethoxy-5-methyl-p-benzoquinone) resulted in a significant protection from antibody disulfide reduction, with only 0.34 and 0.63 thiol per antibody at 0.2 mM and 0.1 mM coenzyme Q0 respectively.

Coenzyme Q0 is known to react with thiols in a stoichiometric manner (W. Li, J. Heinze, and W. Haehnel, J. Am. Chem. Soc., 127, 6140-6141, 2005). It was highly unexpected, however, to observe that coenzyme Q0 was effective in lowering the antibody disulfide reduction at sub-stoichiometric molar concentrations (0.2 and 0.1 mM) compared to the total thiol concentration in the damaged CHO cell supernatant mixture (0.8 mM).

Also, as shown in FIG. 3, coenzyme Q2 (2,3-dimethoxy-5-methyl-6-geranyl-p-benzoquinone), decreased antibody disulfide-reduction by damaged CHO supernatant at low concentrations (0.2 and 0.1 mM) that were sub-stoichiometric in molar terms compared to the total thiol concentration in the damaged CHO cell supernatant mixture (0.8 mM).

In contrast, coenzyme Q10 did not show significant protection toward antibody-disulfide reduction by damaged CHO supernatant when added at 0.2 and 0.1 mM concentrations. It is possible that the low solubility of coenzyme Q10 hinders its ability to protect the antibody-disulfide from reduction.

A sample of humanized N901 antibody incubated with coenzyme Q0 was analyzed by mass spectrometry and showed a mass of 146148, which was similar to that of control, unreduced humanized N901 antibody (mass 146150), thus showing that the antibody was not covalently modified by coenzyme Q0.

Example 3: 1,2-naphthoquinone-4-sulfonic Acid Decreased Antibody Reduction

The effect of 1,2-naphthoquinone-4-sulfonic acid (NQS) on antibody-disulfide reduction was studied by incubating 1,2-naphthoquinone-4-sulfonic acid at several concentrations with antibody and damaged CHO lysate. The damaged CHO cell lysate was generated by the addition of 0.5 ml RIPA buffer (50 mM Tris-HCl, pH 7.4, 1% NP-40, 0.5% sodium deoxycholate, 0.1% sodium dodecylsulfate) to 100 million CHO cells. The thiol concentration in CHO cell lysate was measured by Ellman's assay as 2.1 mM.

Each sample contained pre-mixed 0.5 ml RIPA buffer (50 mM Tris-HCl, pH 7.4, 1% NP-40, 0.5% sodium deoxycholate, 0.1% sodium dodecylsulfate) with 1 mg humanized N901 antibody, with or without 1,2-naphthoquinone-4-sulfonic acid (25 micromolar, or 50 micromolar, or 100 micromolar), which was added to a cell pellet of 100 million CHO cells, and the resuspended cells were incubated at ambient temperature for 30 minutes, following which the cell debris were pelleted by centrifugation (16,000 g, 5 min). The supernatant from each sample was added to 50 microliter immobilized-Protein A beads (RepliGen) and rotated at ambient temperature for 3 hours, after which the supernatant was removed and the beads washed with PBS.

Figure 4:
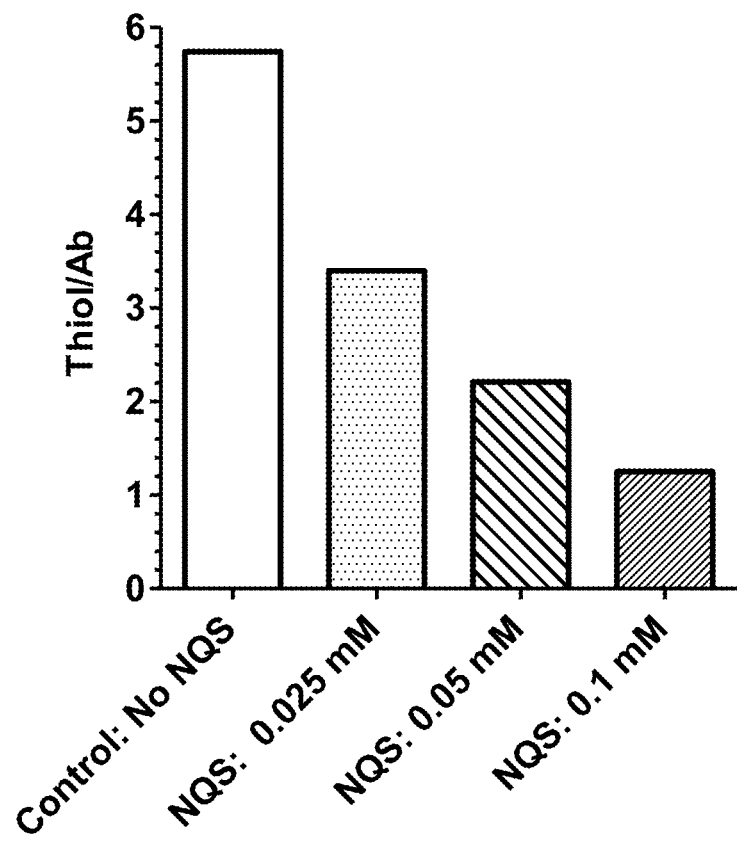
FIG. 4 is a graph that shows the effect of 0.025 mM, 0.05 mM, and 0.1 mM 1,2-naphthoquinone-4-sulfonic acid (NQS), which protects against the reduction of antibody disulfide bonds by a CHO cell lysate.

The thiol content of the immobilized antibody was determined by the addition of 0.6 ml of PBS containing 0.5 mM DTNB (Ellman's reagent) to the beads, rotation for about 10 minutes, centrifugation, and absorbance measurement of supernatant at 412 nm. As shown in FIG. 4, the control antibody sample (without 1,2-naphthoquinone-4-sulfonic acid) upon reduction by CHO cell lysate showed a thiol/antibody ratio of 5.74.

In contrast, addition of low concentrations of naphthoquinone-4-sulfonic acid (NQS) to the mixture of antibody sample and CHO lysate significantly decreased the thiol/antibody ratio. The thiol/antibody ratio was 3.4, 2.2, and 1.25 upon addition of 0.025 mM, 0.05, and 0.1 mM naphthoquinone-4-sulfonic acid (NQS), respectively. The concentrations (0.025-0.1 mM) of NQS that were effective at decreasing the extent of antibody reduction caused by CHO lysate were surprisingly much lower than the thiol concentration in the CHO lysate (2.1 mM).

Example 4: Anthraquinone-2-sulfonic Acid Decreased Antibody-Disulfide Reduction

The effect of anthraquinone-2-sulfonic acid (AQS) on antibody-disulfide reduction was studied during co-incubation of anthraquinone-2-sulfonic acid with antibody and damaged CHO lysate. Each sample contained pre-mixed 1 ml RIPA buffer (50 mM Tris-HCl, pH 7.4, 1% NP-40, 0.5% sodium deoxycholate, 0.1% sodium dodecylsulfate) with 1 mg humanized N901 antibody, with or without 0.2 mM anthraquinone-2-sulfonic acid (AQS), which was added to a cell pellet of 100 million CHO cells, and the resuspended cells were incubated at ambient temperature for 30 minutes, following which the cell debris were pelleted by centrifugation (16,000 g, 5 min). The thiol concentration in CHO cell lysate was 1 mM (Ellman's assay).

Figure 5:
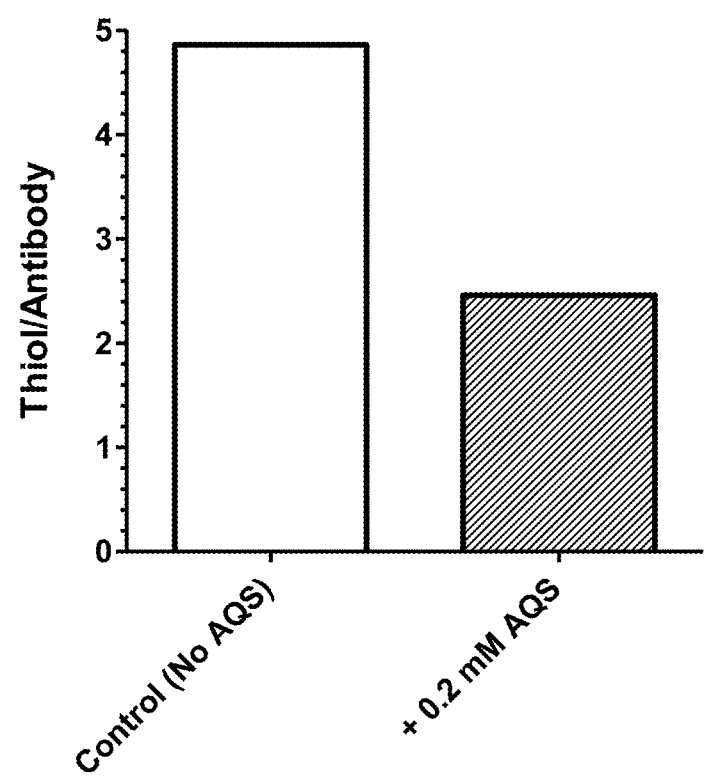
FIG. 5 is a graph that shows the effect of 0.2 mM anthraquinone-2-sulfonic acid (AQS), which protects against the reduction of disulfide bonds in an antibody by a CHO cell lysate.

The supernatant from each sample was added to 50 microliter immobilized-Protein A beads (RepliGen) and rotated at ambient temperature for 3 hours, after which the supernatant was removed and the beads washed with PBS. The thiol content of the immobilized antibody was determined by the addition of 0.6 ml of PBS containing 0.5 mM DTNB (Ellman's reagent) to the beads, rotation for about 10 minutes, centrifugation, and absorbance measurement of supernatant at 412 nm. As shown in FIG. 5, the control antibody sample (without any anthraquinone-2-sulfonic acid) incubated with CHO cell lysate for 3 hours underwent reduction of antibody-disulfide resulting in 4.86 thiol/antibody.

In contrast, the antibody sample (with 0.2 mM anthraquinone-2-sulfonic acid) incubated with CHO cell lysate for 3 hours showed significantly less disulfide-reduction resulting in 2.46 thiol/antibody (49% decrease in antibody-disulfide reduction).

In another experiment, 1 mg huN901 antibody was incubated with CHO lysate, with or without 0.4 mM anthraquinone-2-sulfonic acid for 4 hours. The mixture was then analyzed for thiol/antibody as above. In this experiment, the control antibody sample (without any anthraquinone-2-sulfonic acid) following incubation with CHO cell lysate for 4 hours showed 4.34 thiol/antibody.

In contrast, the antibody sample (with 0.4 mM anthraquinone-2-sulfonic acid) following incubation with CHO cell lysate for 4 hours showed significantly less disulfide-reduction, resulting in a value of 1.65 thiol/antibody (62% decrease in antibody-disulfide reduction).

In a separate experiment, the reactivity of anthraquinone-2-sulfonic acid (AQS) with a model thiol (L-cysteine ethyl ester) at ambient temperature was investigated by incubating 1 mM AQS with 1 mM cysteine ethyl ester at ambient temperature in PBS, using Ellman's assay of thiol groups to measure the extent of reaction. At time points of 1 hour, 2 hours, 3 hours, and 4 hours, the percent decrease in thiol values for the 1 mM AQS with 1 mM cysteine ethyl ester mixture versus thiol in a 1 mM cysteine ethyl ester (No AQS) control were 2%, 8%, 12%, and 20%, respectively.

It was surprising to observe a 49% decrease in antibody-disulfide reduction by CHO lysate following 3 hours incubation with 0.2 mM AQS, and a 62% decrease in antibody-disulfide reduction by CHO lysate following 4 hours incubation with 0.4 mM AQS. The extent of protection against antibody disulfide-reduction was much greater than expected given the thiol reaction kinetics observed at 3 hours (12% lower thiol) and 4 hours (20% lower thiol), which were based on the reaction of 1 mM cysteine ethyl ester with 1 mM AQS.

The effect of incubating cells with anthraquinone-2-sulfonic acid (AQS) was tested using Calu3 human lung cancer cells. Effects on cell viability were assayed by microscopic observation of cells and by ATP-based viability assay using Cell Titer Glo reagent (Promega). Upon incubation of Calu3 cells with 0.25 and 0.5 mM AQS for 1 day, no visible cytotoxic effects were observed and the luminescence values obtained using Cell Titer Glo reagent were similar (100% and 85%, respectively) to that of control cells without AQS, demonstrating that AQS is not cytotoxic at these concentrations.

In another experiment to test the effect of AQS on the viability of cells, CHO cells producing antibody were kept in continuous culture for about two weeks, and then were treated with 0.25 mM, 0.5 mM, and 0.75 mM AQS for 1 day. Cell viability was measured after this treatment. The viability count using trypan blue for control, untreated cells was 63.8%, which was similar to that for AQS-treated cells (66.2%, 64.8%, and 61.7% for 0.25, 0.5, and 0.75 mM AQS-treated cells, respectively). AQS, therefore, was not cytotoxic to antibody-producing cells.

Figure 6A:
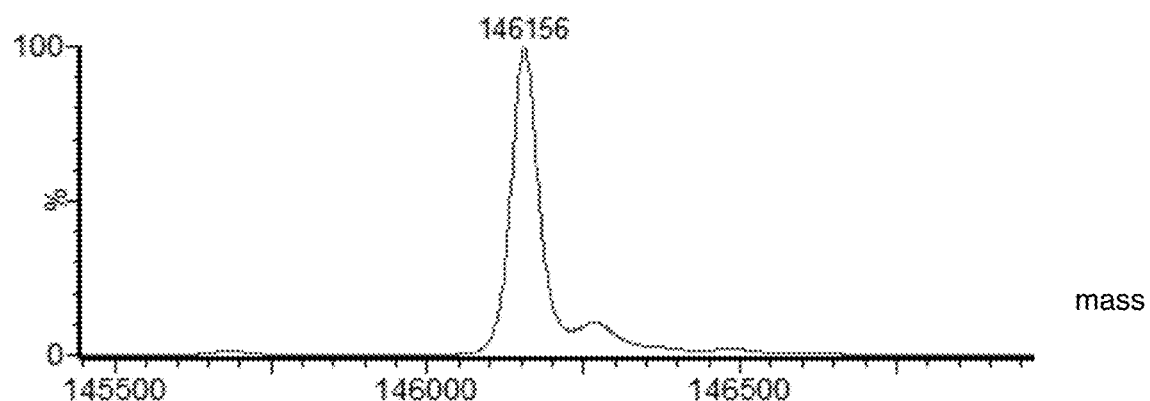
FIG. 6A shows the mass spectrum of deglycosylated antibody sample from antibody sample treated with anthraquinone-2-sulfonic acid (AQS) and a CHO cell lysate.
Figure 6B:
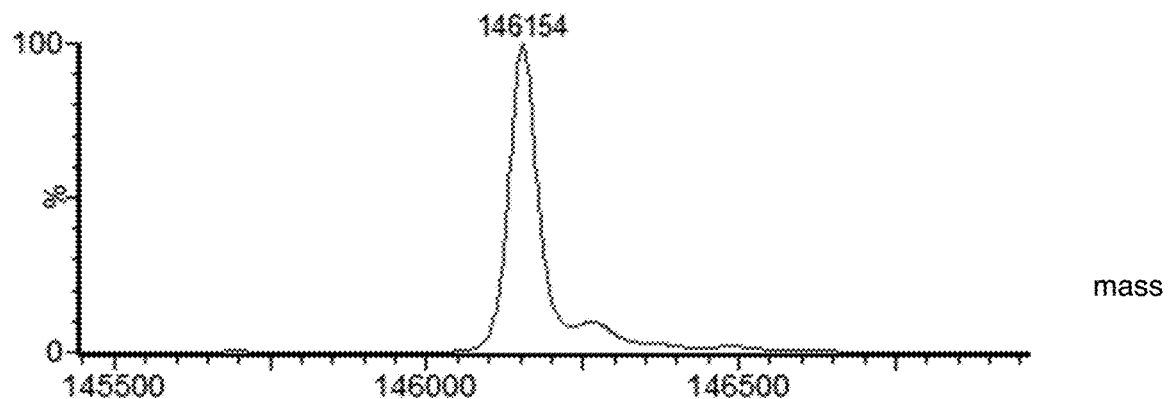
FIG. 6B shows the mass spectrum of deglycosylated antibody sample from control, unreduced humanized IgG1 antibody sample.

To test the effect of AQS-treatment on covalent modification of antibody, humanized N901 IgG1 (2 mg in 1 ml PBS) was treated with 1 mM AQS and 0.35 ml CHO cell lysate (prepared by lysis and centrifugation of 100 million CHO cells in 1 ml RIPA buffer), then added to 100 microliter Protein A beads, and rotated for 3 hours. The immobilized antibody was washed with PBS, eluted in 100 mM acetic acid containing 150 mM NaCl, neutralized to pH 7 with 1.25 M $KH_2PO_4$ solution, and dialyzed. The dialyzed antibody was deglycosylated and analyzed by mass spectrometry, which showed a mass of 146156 that was similar to that of control, unreduced antibody (mass 146154) (FIG. 6B), indicating that AQS did not covalently modify the antibody (FIG. 6A).

Example 5: Lipoic Acid Decreased Antibody Reduction

Humanized anti-folate receptor-1 IgG1 (1 mg) was immobilized on 0.05 ml of Protein A beads (RepliGen) and then treated with pre-mixed 0.5 ml PBS and 0.1 ml damaged CHO cell supernatant with or without 0.5 mM and 2 mM lipoic acid (also named as 1,2-dithiolane-3-pentanoic acid; or 6,8-dithiooctanoic acid; or DL-6,8-thioctic acid; added using a stock solution of lipoic acid in DMSO), pre-incubated for 20 min before addition to immobilized antibody. The concentration of total thiol (derived from damaged cells) in this mixture was 0.67 mM.

The samples were rotated for about 2.5 hours at ambient temperature, then centrifuged to pellet beads, following which the supernatants were removed and the beads washed with PBS four times. The thiol content of the immobilized antibody on the beads was then analyzed by the addition of 0.6 ml PBS containing 0.5 mM DTNB to the beads, which were incubated with rotation for about 5 minutes and centrifuged to pellet the beats. The absorbance of the supernatant was measured at 412 nm.

Figure 7:
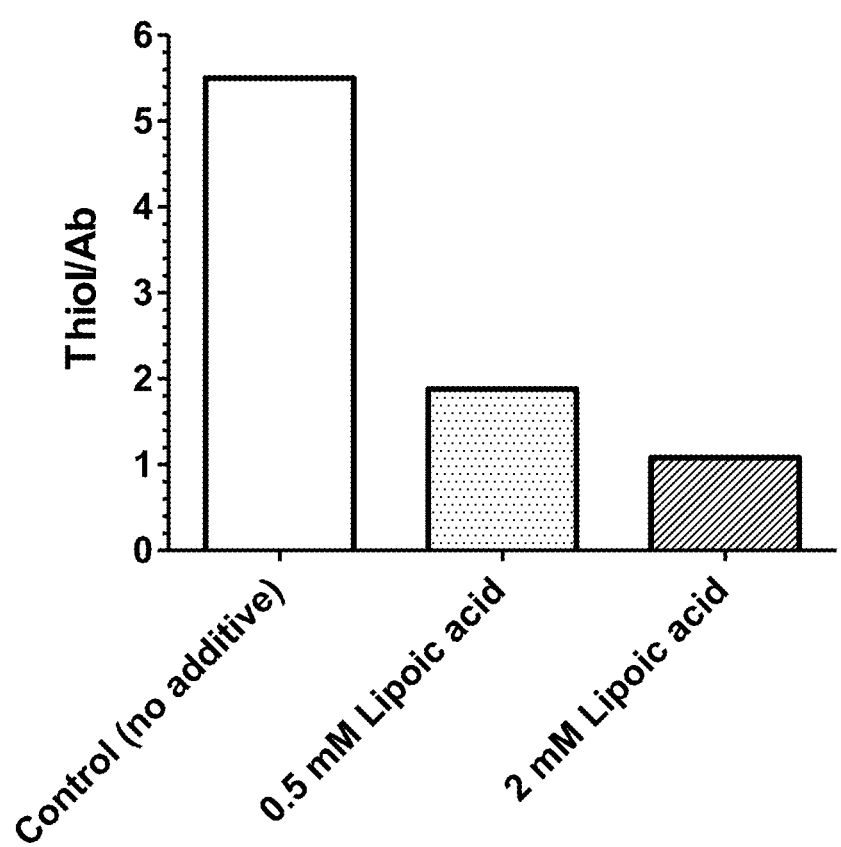
FIG. 7 is a graph that shows the effect of lipoic acid treatment, which protects native disulfide bonds in humanized IgG1 antibody exposed to damaged CHO cell supernatant.

In the control antibody sample without lipoic acid, the number of thiol residues per antibody molecule after incubation with damaged CHO cell supernatant was calculated as 5.5. For the 0.5 mM and 2 mM lipoic acid-treated mixtures of antibody and damaged CHO cell supernatant, the thiol/antibody ratios were 1.88 and 1.08, respectively (FIG. 7). Even at a lipoic acid concentration of 0.5 mM, which was lower than the total thiol concentration of 0.67 mM, a significant decrease of thiol/Ab was obtained for the mixture of damaged CHO cell supernatant with antibody.

In another experiment, the viability of CHO cells treated with 0.75 mM lipoic acid for 1 day was measured as 98.1%, which was similar to the viability of control, untreated cells (98.9% viability). Lipoic acid treatment, therefore, was not cytotoxic to CHO cells.

Figure 8A:
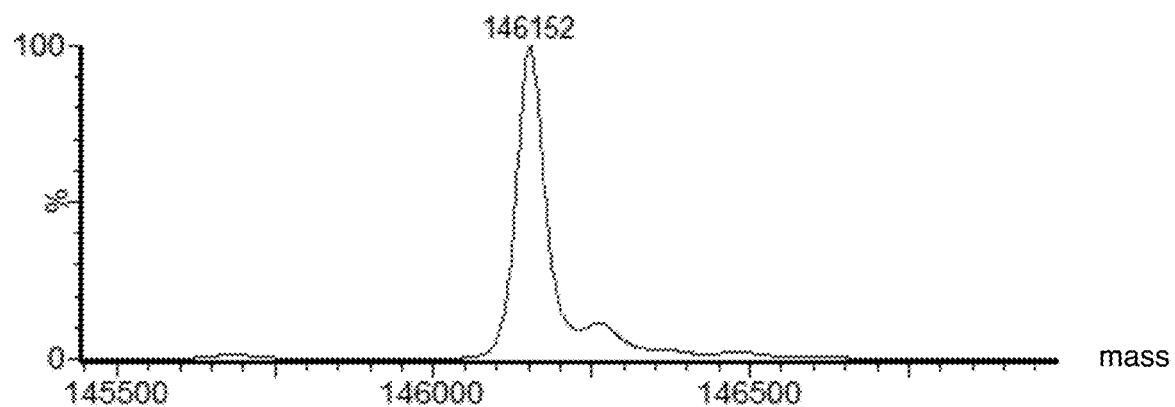
FIG. 8A shows the mass spectrum of deglycosylated antibody sample from antibody sample treated with lipoic acid and CHO cell lysate.
Figure 8B:
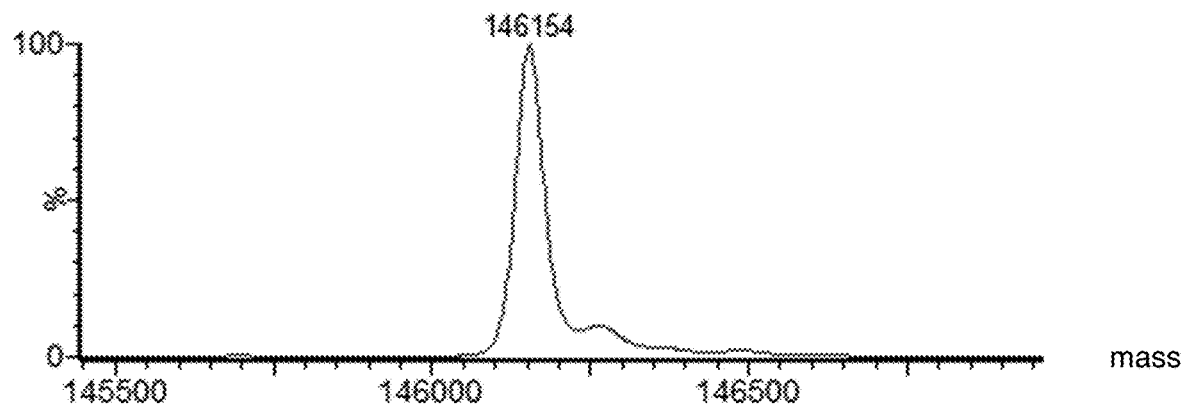
FIG. 8B shows the mass spectrum of deglycosylated antibody sample from unreduced humanized IgG1 antibody sample.

To test the effect of lipoic acid-treatment on covalent modification of antibody, humanized N901 IgG1 (2 mg in 1 ml PBS) was treated with 1 mM lipoic acid and 0.35 ml CHO cell lysate (prepared by lysis and centrifugation of 100 million CHO cells in 1 ml RIPA buffer), then added to 100 microliter Protein A beads, and rotated for 3 hours. The immobilized antibody on beads was washed with PBS, eluted in 100 mM acetic acid containing 150 mM NaCl, neutralized to pH 7 with 1.25 M $KH_2PO_4$ solution, and dialyzed. The dialyzed antibody was deglycosylated and analyzed by mass spectrometry, which showed a mass of 146152 that was similar to that of control, unreduced antibody (mass 146154) (FIG. 8B), indicating that lipoic acid did not covalently modify the antibody (FIG. 8A).

Lipoic acid contains a strained 5-membered cyclic disulfide (S. Sunner, Nature, 176, 217, 1955). The strained cyclic disulfide group in lipoic acid is more reactive toward thiol than non-cyclic disulfides, which would favor the reduction of lipoic acid by CHO cell thiol proteins in comparison to antibody disulfide bonds.

However, the reduced lipoic acid is a 1,3-dithiol, which has a higher reduction potential than monothiols (W. J. Lees and G. M. Whitesides, J. Org. Chem., 58, 642-647, 1993), and it is possible that reduced lipoic acid (dihydrolipoic acid) could reduce antibody disulfide bonds. It was therefore unexpected that lipoic acid decreased antibody disulfide reduction by damaged CHO cell suspension or lysate.

Example 6: Cystine Dimethyl Ester and Cystine Diethyl Ester Each Decreased Antibody Reduction The effect of L-cystine dimethyl ester (CDME) on antibody-disulfide reduction was studied following co-incubation of CDME at several concentrations with antibody and damaged CHO lysate. Each sample contained pre-mixed 1 ml RIPA buffer (50 mM Tris-HCl, pH 7.4, 1% NP-40, 0.5% sodium deoxycholate, 0.1% sodium dodecylsulfate) with 1 mg humanized N901 antibody, with or without 0.05-0.5 mM L-cystine dimethyl ester (CDME), which was added to a cell pellet of 100 million CHO cells, and the resuspended cells were incubated at ambient temperature for 30 minutes, following which the cell debris were pelleted by centrifugation (16,000 g, 5 min). The thiol concentration in CHO cell lysate was 1 mM (Ellman's assay).

The supernatant from each sample was added to 50 microliter immobilized-Protein A beads (RepliGen) and rotated at ambient temperature for 3 hours, after which the supernatant was removed and the beads washed with PBS. The thiol content of the immobilized antibody was determined by the addition of 0.6 ml of PBS containing 0.5 mM DTNB (Ellman's reagent) to the beads, rotation for about 10 minutes, centrifugation, and absorbance measurement of the supernatant at 412 nm.

Figure 9:
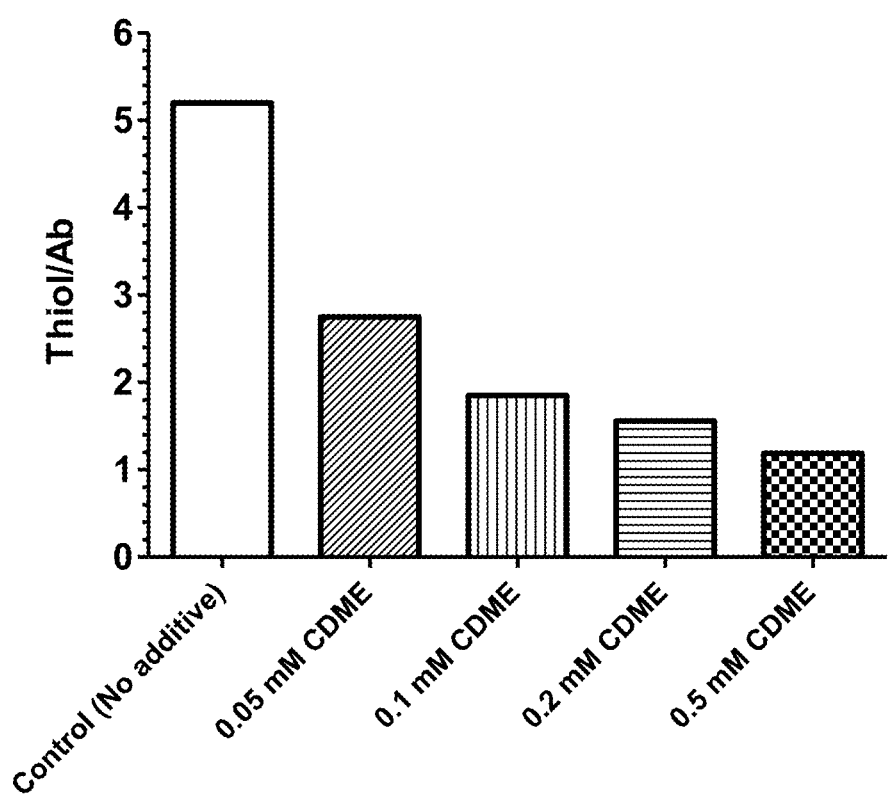
FIG. 9 is a graph that shows the effect of L-cystine dimethyl ester (CDME), which protects against the reduction of disulfide bonds in antibody exposed to a CHO cell lysate.

The control, antibody sample (without any CDME) showed 5.20 thiol/antibody generated by reduction of antibody disulfide by CHO lysate. In contrast, as shown in FIG. 9, treatment with 0.05 mM, 0.1 mM, 0.2 mM, and 0.5 mM CDME significant decreased antibody-disulfide reduction by CHO lysate, resulting in 2.75, 1.85, 1.56, and 1.19 thiol/antibody, respectively. Unexpectedly, CDME decreased the disulfide-reduction in antibody by CHO lysate, even at low concentrations of CDME (0.05-0.5 mM) that were significantly lower than the total thiol concentration in CHO lysate mixture (1 mM).

Figure 10:
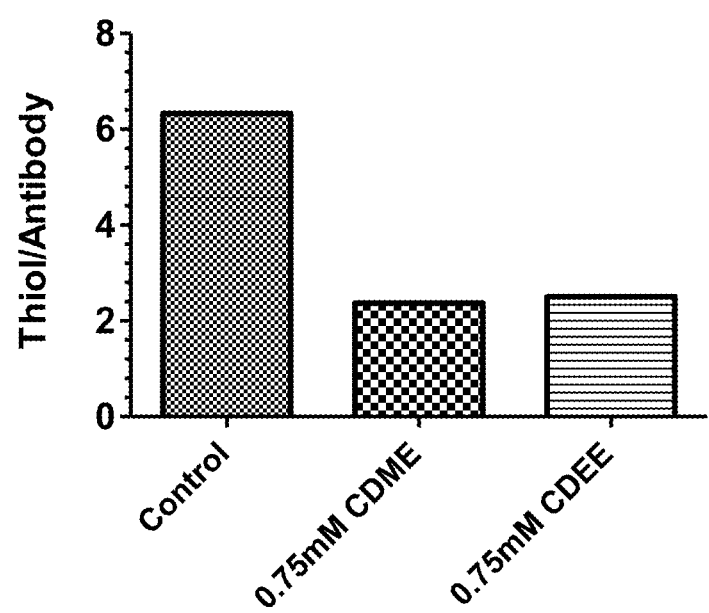
FIG. 10 is a graph that shows the effect of L-cystine dimethyl ester (CDME) and L-cystine diethyl ester (CDEE), which protect against the reduction of disulfide bonds in an antibody by a CHO cell lysate.
Figure 11:
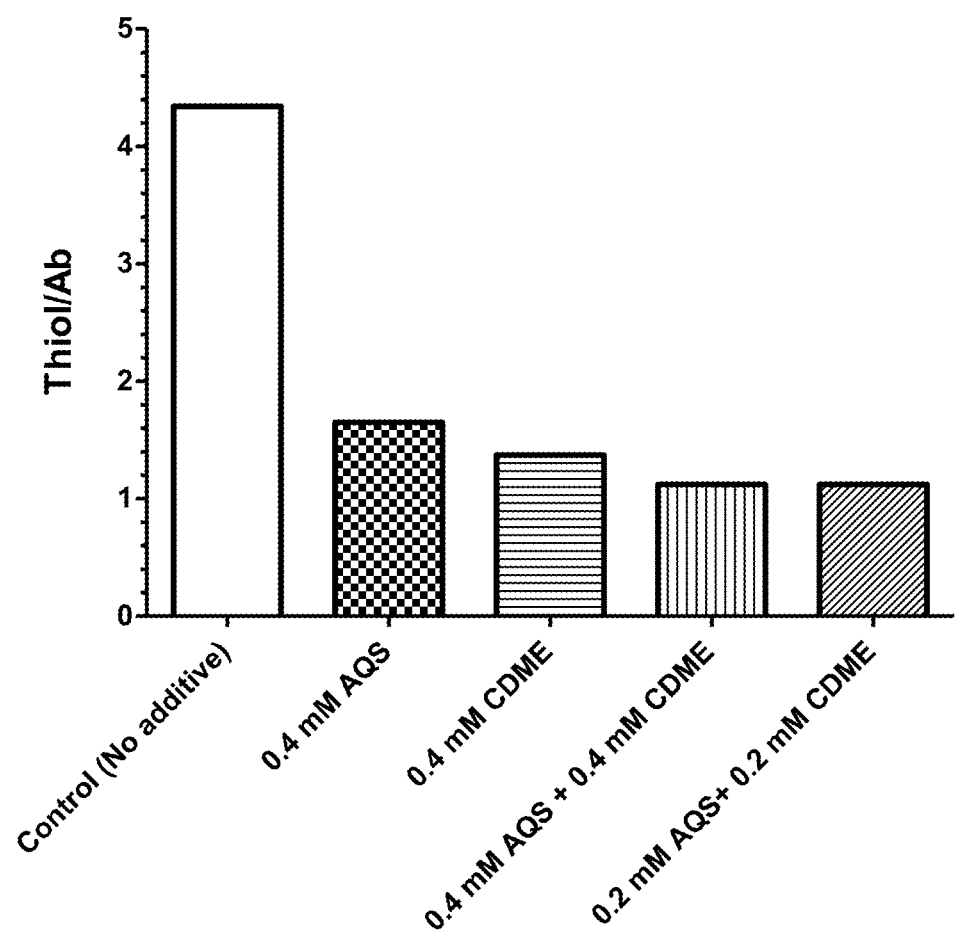
FIG. 11 is a graph that shows the effect of a combination of L-cystine dimethyl ester (CDME) and anthraquinone-2-sulfonic acid (AQS), which protects against the reduction of disulfide bonds in antibody by a CHO cell lysate.

In another experiment, cystine dimethyl ester (CDME) and cystine diethyl ester (CDEE) were added at 0.75 mM each to a mixture of 2 mg humanized N901 IgG1 and CHO lysate, and the samples were rotated at 4° C. overnight, after which the thiol/antibody was determined using PBS and DTNB mixture as described above. As shown in FIG. 10, addition of 0.75 mM of CDME or CDEE decreased the extent of disulfide reduction of antibody caused by CHO lysate to 0.96 and 1.02 thiol/antibody, respectively, compared to the thiol/antibody value of 2.29 for the control sample without any CDME or CDEE. FIG. 11 shows that incubation of antibody with a combination of anthraquinone-2-sulfonic acid (AQS) and CDME at 0.2 mM each or 0.4 mM each decreased the extent of antibody-disulfide reduction by CHO lysate significantly.

In contrast to the control sample (without AQS or CDME) that showed 4.34 thiol/antibody, treatment with a combination of AQS and CDME decreased the antibody-disulfide reduction to 1.12 thiol/antibody, both for 0.2 mM each, and 0.4 mM each of AQS and CDME (FIG. 11). These values of thiol/antibody obtained with the combination of AQS and CDME were lower than those with 0.4 mM AQS alone (1.65 thiol/antibody) or with 0.4 mM CDME alone (1.37 thiol/antibody), indicating that the combinations were even more effective in decreasing antibody reduction than the individual agents.

Figure 12:
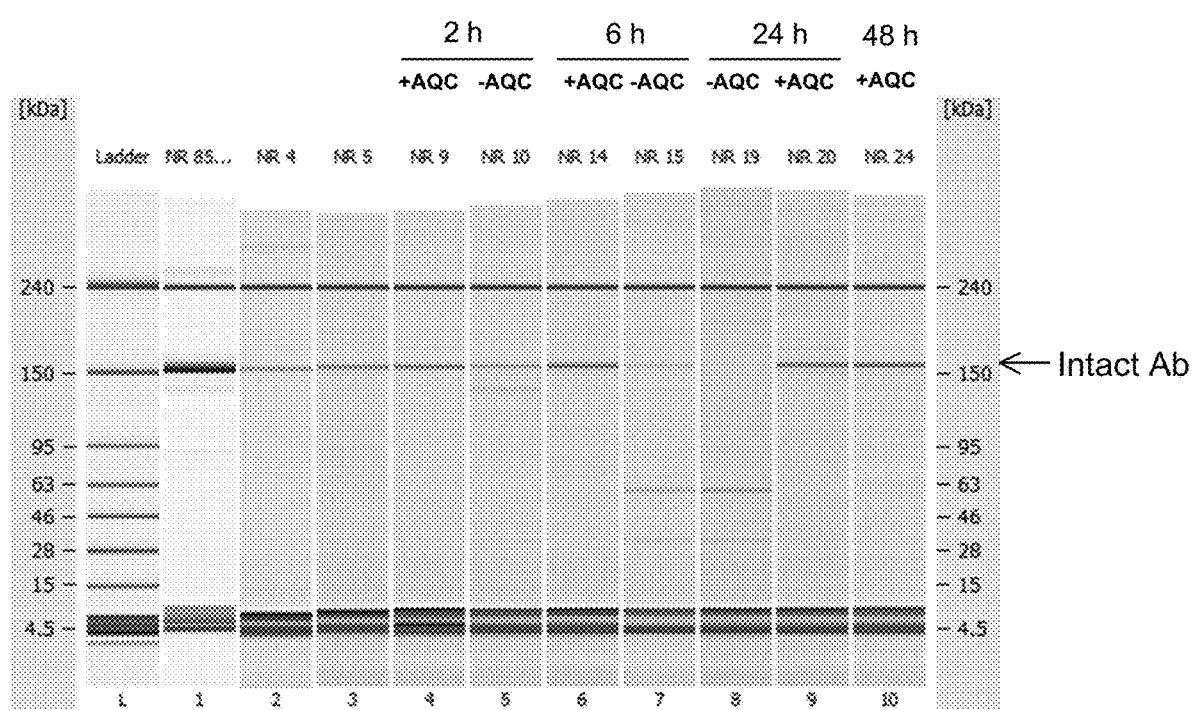
FIGS. 12A and 12B show the effect of a combination of L-cystine dimethyl ester (CDME) and anthraquinone-2-sulfonic acid (AQS) on antibody fragmentation in harvest cell culture fluid derived from humanized IgG1-producing CHO cells. This combination is referred to as "AQC."

FIG. 12A and FIG. 12B show the results of an experiment in which a CHO cell culture producing recombinant humanized IgG1 antibody was subjected to depth filtration and the resulting harvest cell culture fluid (HCCF) was frozen at −80° C. After thaw, two samples were prepared which were kept under nitrogen in bottles at ambient temperature. To one sample was added a combination of 0.5 mM anthraquinone-2-sulfonic acid (AQS) and 0.5 mM cystine dimethyl ester dihydrochloride (CDME), termed "AQC".

Another sample, without any added AQS or CDME, served as the control. At various time points, samples were quenched with 5 mM N-ethylmaleimide (NEM), purified using immobilized Protein A, and subjected to non-reducing SDS-Protein Lab Chip electrophoretic analysis.

FIG. 15A shows the non-reducing SDS-Protein Lab Chip electrophoretic data, which are quantitatively shown in FIG. 15B. The combination of AQS and CDME ("AQC") significantly decreased antibody fragmentation at all time points from 2 hours to 68 hours compared to the control without any AQS or CDME added (FIG. 15A, 15B). For example, at 24 hours the control sample (without any AQS or CDME) showed 89.6% fragmentation of antibody, whereas the sample treated with the combination of AQS and CDME ("AQC") showed only 5% fragmentation, which was similar to that of untreated antibody.

A significant decrease in the percentage fragmentation (and correspondingly higher percentage of intact antibody) was seen at all time points analyzed for the sample treated with the combination of AQS and CDME compared to the control sample without any AQS or CDME (FIG. 15B).

Figure 13A:
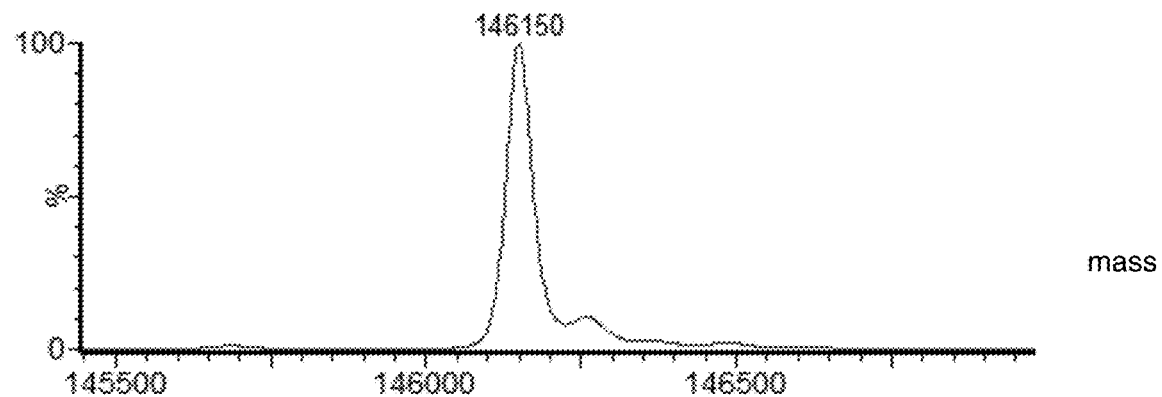
FIG. 13A shows the mass spectrum of deglycosylated antibody sample from antibody sample treated with L-cystine dimethyl ester (CDME) and CHO cell lysate.
Figure 13B:
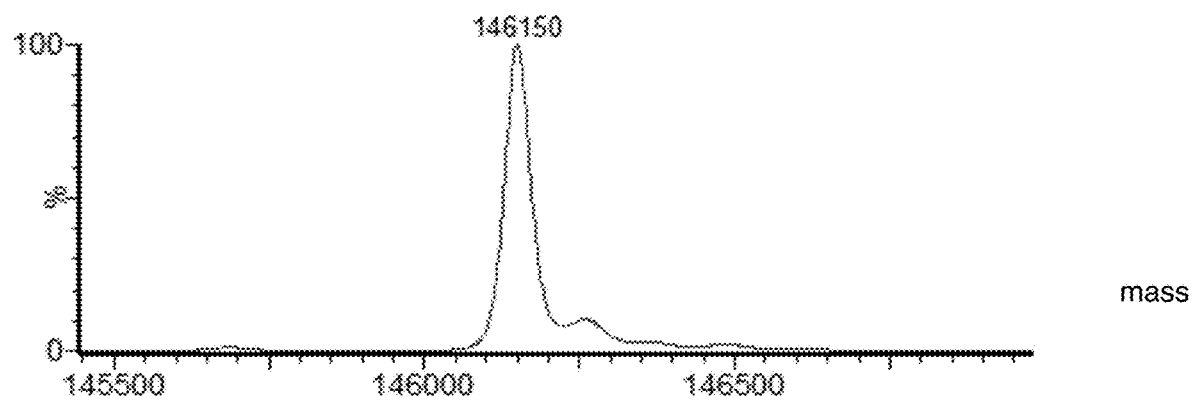
FIG. 13B shows the mass spectrum of deglycosylated antibody sample from control, unreduced humanized IgG1 antibody sample.

To test the effect of CDME-treatment on covalent modification of antibody, humanized N901 IgG1 (2 mg in 1 ml PBS) was treated with 1 mM CDME and 0.35 ml CHO cell lysate (prepared by lysis and centrifugation of 100 million CHO cells in 1 ml RIPA buffer), then added to 100 microliter Protein A beads, and rotated for 3 hours. The immobilized antibody was washed with PBS, eluted in 100 mM acetic acid containing 150 mM NaCl, neutralized to pH 7 with 1.25 M $KH_2PO_4$ solution, and dialyzed. The dialyzed antibody was deglycosylated and analyzed by mass spectrometry, which showed a mass of 146150 that was similar to that of untreated antibody (mass 146154) (FIG. 13B), indicating that cystine dimethyl ester treatment did not covalently modify the antibody (FIG. 13A).

The aqueous solubilities of L-cystine dimethyl ester dihydrochloride and L-cystine diethyl ester dihydrochloride were compared to those of L-cystine and L-cystine dihydrochloride. Unexpectedly, the solubilities of L-cystine dimethyl ester dihydrochloride and L-cystine diethyl ester dihydrochloride in water were found to be much higher than those of L-cystine and L-cystine dihydrochloride.

In contrast to L-cystine, which could be dissolved in water at only about 0.5 mM, the L-cystine dimethyl ester dihydrochloride and L-cystine diethyl ester dihydrochloride could be dissolved in water even at 1000 mM. The aqueous solubility of L-cystine dimethyl ester dihydrochloride and L-cystine diethyl ester dihydrochloride, therefore, was 2000 times higher than that of L-cystine.

For addition of concentrated solutions of L-cystine dimethyl ester dihydrochloride and L-cystine diethyl ester dihydrochloride to media at pH 7, it would be desirable to add neutralized stock solutions at about pH 7. The aqueous solubility of L-cystine dimethyl ester dihydrochloride and L-cystine diethyl ester dihydrochloride were investigated after neutralization to about pH 7 by addition of IN NaOH.

Unexpectedly, it was found that even after neutralization to about pH 7, the L-cystine dimethyl ester dihydrochloride and L-cystine diethyl ester dihydrochloride samples remained soluble at concentrations higher than 100 mM. The unexpectedly high aqueous solubilities of L-cystine dimethyl ester dihydrochloride (CDME) and L-cystine diethyl ester dihydrochloride (CDEE) after neutralization to about pH 7 allow the addition of concentrated solutions of these agents (CDME, or CDEE) to cell culture medium to obtain final concentrations in mM range without altering the pH of the medium.

If desired, concentrated solutions of L-cystine dimethyl ester dihydrochloride or L-cystine diethyl ester dihydrochloride and base (such as NaOH) can also be added to the medium without altering the pH of the medium.

The disulfide-reduction protection offered by a saturated solution of L-cystine dihydrochloride was compared with a L-cystine dimethyl ester (L-CDME) dihydrochloride solution. The saturated solution of L-cystine dihydrochloride was prepared by suspending 11.7 mg of cystine dihydrochloride (FW 313.2) in 7.47 ml of 50 mM potassium phosphate buffer, pH 7. The pH was adjusted to pH 7.1 and the sample was rotated overnight at ambient temperature followed by centrifugation to remove undissolved L-cystine dihydrochloride. This saturated solution of L-cystine was at a concentration less than 5 mM, which would have been the theoretical concentration if all of the initially added 11.7 mg L-cystine dihydrochloride had dissolved completely in 7.47 ml. In contrast, a fully soluble 5 mM L-cystine dimethyl ester dihydrochloride solution could be readily prepared in 50 mM potassium phosphate buffer, pH 7, and its pH was adjusted to pH 7.1. L-cystine dimethyl ester is soluble at much higher concentrations; the concentration of 5 mM used in this experiment was for comparison with L-cystine.

Figure 14:
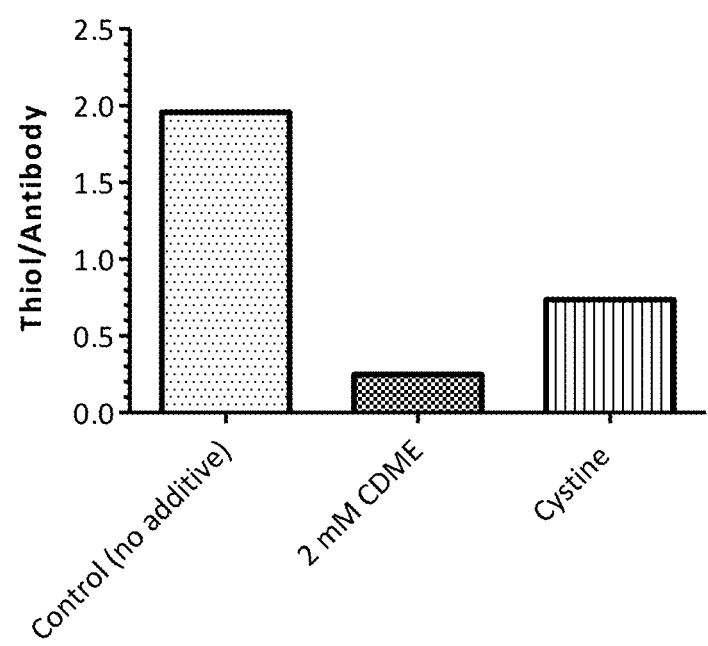
FIG. 14 is a graph that shows that L-cystine dimethyl ester (CDME) is more effective than L-cystine for protection against the reduction of disulfide bonds in an antibody by a CHO cell lysate.

Humanized FOLR1 IgG1 antibody (3 mg) in 0.3 ml of 50 mM potasssium phosphate buffer, pH 7, was incubated with 0.59 ml of above saturated L-cystine solution, or with 0.59 ml of 5 mM L-CDME solution, or with 0.59 ml of 50 mM potasssium phosphate buffer, pH 7. Lysates of CHO cells (~60 million cells lysed in 0.6 ml RIPA buffer and clarified by centrifugation) were added to each of these mixtures. The pH values of all samples were adjusted to 7. Each sample was at a final volume of 1.5 ml, which contained 2 mg/ml humanized antibody, without any protectant (control), or with L-cystine (derived from saturated L-cystine solution), or with 2 mM L-CDME. The samples were incubated with 200 microliter immobilized-Protein A beads (RepliGen) and rotated at ambient temperature for 3 hours, after which the supernatant was removed and the beads washed with PBS. The thiol content of the immobilized antibody was determined by the addition of 0.2 ml of PBS containing 0.5 mM DTNB (Ellman's reagent) to the beads, rotation for about 10 minutes, centrifugation, and absorbance measurement of the supernatant at 412 nm. As shown in FIG. 14, the control sample showed reduction of disulfide bonds in antibody resulting in 1.96 thiol per antibody. The sample derived from saturated L-cystine dihydrochloride showed a lower extent of antibody-disulfide reduction, with about 0.74 thiol per antibody. It was highly surprising and unexpected that 2 mM L-CDME was superior to L-cystine toward antibody-disulfide reduction, resulting in only about 0.25 thiol per antibody.

Figure 15:
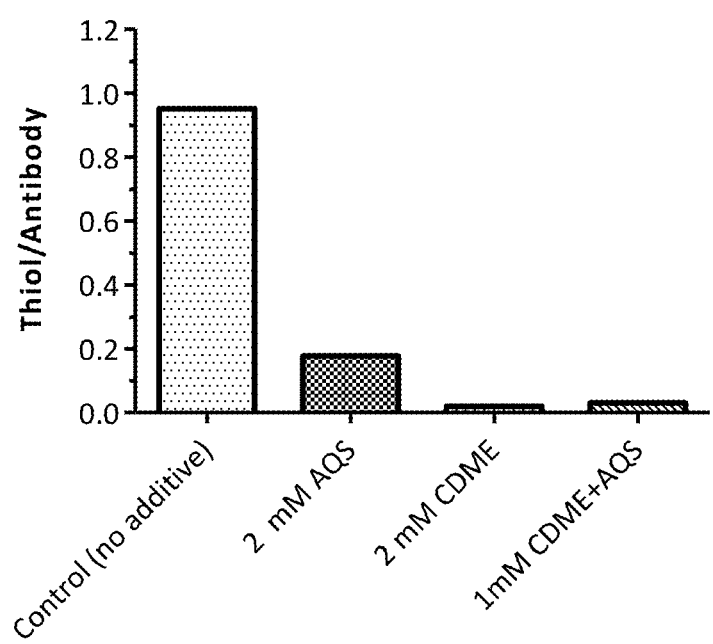
FIG. 15 is a graph that shows the effect of 2 mM L-cystine dimethyl ester (CDME), 2 mM anthraquinone-2-sulfonic acid (AQS), and their combination (1 mM CDME+1 mM AQS), which protect against the reduction of disulfide bonds in an antibody by a CHO cell lysate.

Humanized FOLR1 IgG1 antibody (2 mg/ml) in 50 mM potassium phosphate buffer, pH 7, was incubated with 2 mM CDME, or 2 mM AQS, or a mixture of 1 mM CDME and 1 mM AQS, followed by addition of lysate of CHO cells (~40 million cells lysed in 0.4 ml RIPA buffer and clarified by centrifugation). The pH values of all samples were adjusted to 7. The samples were incubated with 200 microliter immobilized-Protein A beads (RepliGen) and rotated at ambient temperature for 3 hours, after which the supernatant was removed and the beads washed with PBS. The thiol content of the immobilized antibody was determined by the addition of 0.2 ml of PBS containing 0.5 mM DTNB (Ellman's reagent) to the beads, rotation for about 10 minutes, centrifugation, and absorbance measurement of the supernatant at 412 nm. As shown in FIG. 15, the control sample showed reduction of disulfide bonds in antibody resulting in 0.95 thiol per antibody. The 2 mM AQS containing sample showed a lower extent of antibody-disulfide reduction, with about 0.18 thiol per antibody. The 2 mM CDME and the 1 mM CDME+1 mM AQS combination treated samples showed much lower levels of Ab-disulfide reduction, resulting in only about 0.02 and 0.03 thiol per antibody, respectively.

Figure 16:
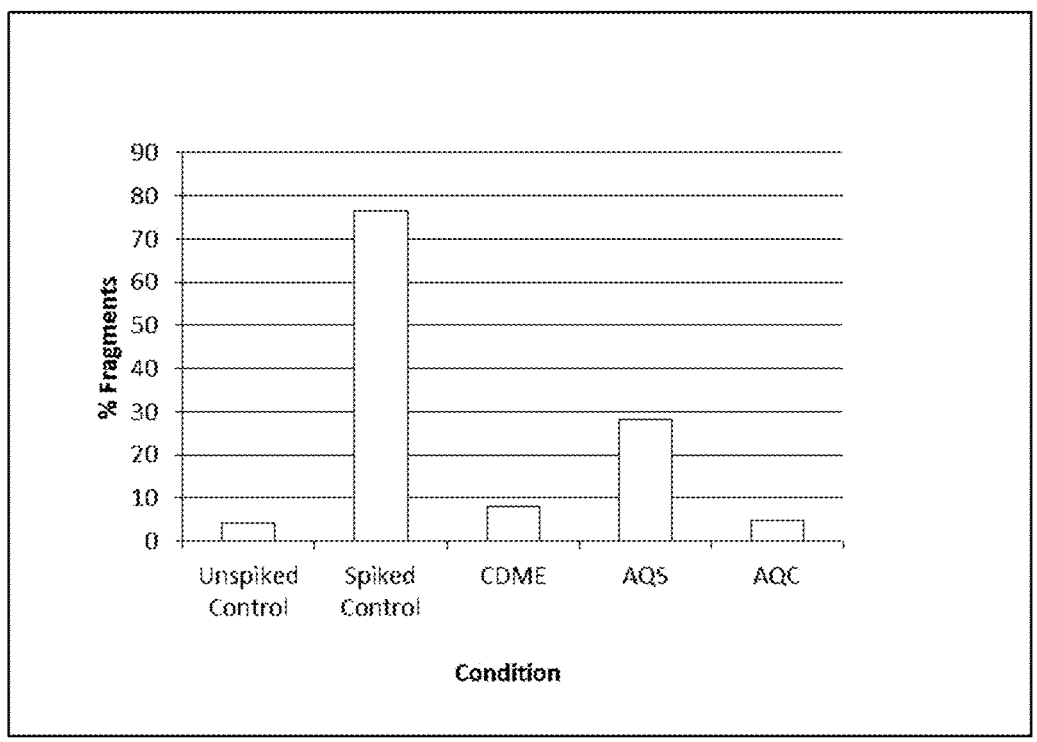
FIG. 16 is a graph that shows the effect of 1 mM L-cystine dimethyl ester (CDME), 1 mM anthraquinone-2-sulfonic acid (AQS), and their combination (1 mM CDME+1 mM AQS), which protect against the fragmentation of an antibody by a microfluidized CHO lysate (20% v/v).

In another experiment, a 14 day harvest cell culture fluid of humanized FOLR1 IgG1 producing CHO cells was treated with 20% (v/v) of microfluidized CHO cells in the absence or presence of additives (1 mM CDME, 1 mM AQS, or 1 mM CDME+1 mM AQS, termed "AQC"). The microfluidization was carried out using 3 liter CHO cells from a bioreactor, which were resuspended into 300 ml PBS, processed through microfluidizer, centrifuged and filtered through 0.22 micrometer membrane. The samples of HCCF+microfluidized CHO cells (20% v/v), without or with CDME, AQS, or CDME+AQS, were incubated for 6 h. The samples were quenched with 5 mM N-ethylmaleimide (NEM), purified using immobilized Protein A, and subjected to non-reducing SDS-Protein Lab Chip electrophoretic analysis. As shown in FIG. 16, 78% fragmentation was observed for the no additive control. In contrast, much lower fragmentations were observed for samples which contained 1 mM CDME, 1 mM AQS, and 1 mM CDME and 1 mM AQS (termed "AQC").

In another experiment, the viability of CHO cells treated with 0.75 mM L-cystine dimethyl ester (CDME) for 1 day was measured as 98.9%, which was similar to the viability of control, untreated cells (98.9% viability). L-cystine dimethyl ester (CDME) treatment, therefore, was not cytotoxic to CHO cells.

Figure 17:
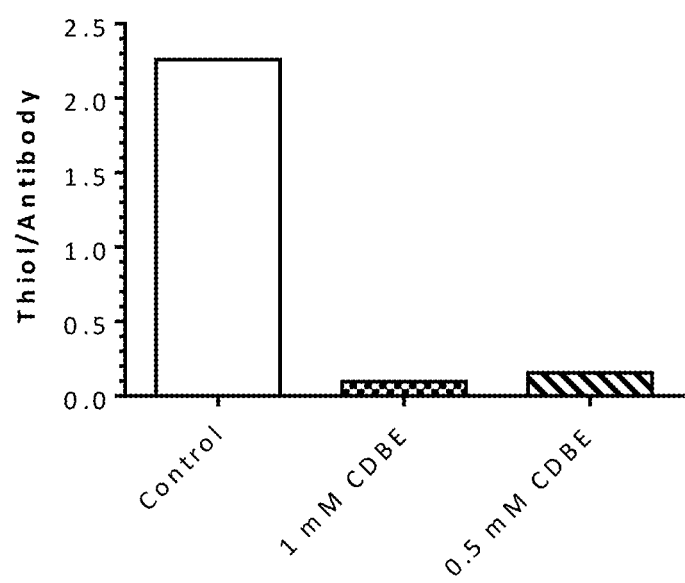
FIG. 17 is a graph that shows the effect of 0.5 and 1 mM L-cystine bis(t-butyl) ester (CDBE), which protect against the reduction of disulfide bonds in an antibody by a CHO cell lysate.

To test the effect of L-cystine bis(t-butyl ester) (CDBE) on protecting antibody disulfide bonds from reduction by CHO lysate, humanized FOLR1 IgG1 antibody (2 mg) was incubated with CHO lysate in RIPA buffer (0.6 ml lysate of 60 million CHO cells in 0.6 ml RIPA buffer, clarified by centrifugation) without or with 0.5 or 1 mM CDBE. The samples were rotated at ambient temperature with 200 microliter immobilized-Protein A beads (RepliGen) for 2 hours, after which the supernatant was removed and the beads washed with PBS. The thiol content of the immobilized antibody was determined by the addition of 0.2 ml of PBS containing 0.5 mM DTNB (Ellman's reagent) to the beads, centrifugation, and absorbance measurement of the supernatant at 412 nm. As shown in FIG. 17, the control sample (without any CDBE) showed reduction of disulfide bonds in antibody resulting in 2.26 thiol per antibody. The 0.5 mM CDBE and the 1 mM CDBE treated samples showed much lower levels of Ab-disulfide reduction, resulting in only about 0.16 and 0.10 thiol per antibody, respectively (that is, about 93% and 96% decrease in disulfide reduction compared to the control without CDBE, respectively).

In another experiment, the use of 0.25 and 2 mM CDBE during the incubation of antibody with CHO cell lysate showed about 78% and 98% decrease in disulfide reduction compared to the control without CDBE, respectively.

The solubility of L-cystine bis(t-butyl ester) (CDBE) was explored by dissolving L-cystine bis(t-butyl ester) dihydrochloride in water. Unexpectedly, L-cystine bis(t-butyl ester) dihydrochloride was found to be soluble in water even at a high concentration of 500 mM.

To test the effect of Di-N-acetyl L-cystine on protecting antibody disulfide bonds from reduction by CHO lysate, humanized FOLR1 IgG1 antibody (3 mg) was incubated with CHO lysate (0.6 ml lysate of 60 million CHO cells in 0.6 ml RIPA buffer, clarified by centrifugation) in 100 mM phosphate buffer (total volume 1.5 ml; pH 7), without any added compound or with 5 mM Di-N-acetyl L-cystine or with 2 mM L-cystine dimethyl ester. The samples were rotated at ambient temperature with 200 microliter immobilized-Protein A beads (RepliGen) for 2 hours, after which the supernatant was removed and the beads washed with PBS. The thiol content of the immobilized antibody was determined by the addition of 0.2 ml of PBS containing 0.5 mM DTNB (Ellman's reagent) to the beads, centrifugation, and absorbance measurement of the supernatant at 412 nm. The control sample (without any added compound) showed reduction of disulfide bonds in antibody resulting in 1.16 thiol per antibody. The 5 mM Di-N-acetyl L-cystine and 2 mM L-cystine dimethyl ester treated samples showed significantly lower levels of Ab-disulfide reduction, resulting in only about 0.42 and 0.13 thiol per antibody, respectively (that is, about 64% and 89% decrease in disulfide reduction compared to the control without any added compound, respectively).

Example 7: Oxidized Glutathione (GSSG) Alone or in Combination with Glutathione Reductase Decreased Antibody Reduction The effect of a combination of glutathione reductase and oxidized glutathione (GSSG) on antibody-disulfide reduction was studied by co-incubating antibody and CHO cell lysate. Each sample contained 1 ml pre-mixed RIPA buffer (50 mM Tris-HCl, pH 7.4, 1% NP-40, 0.5% sodium deoxycholate, 0.1% sodium dodecylsulfate) with 1 mg humanized N901 antibody, with or without 2 mM GSSG alone or a combination of 2 mM GSSG and 1.5 units (15 microgram) glutathione reductase (purified from Baker's yeast). Each sample was added to a cell pellet of 100 million CHO cells, and the resuspended cells were incubated at ambient temperature for 30 minutes, following which the cell debris were pelleted by centrifugation (16,000 g, 5 min). The thiol concentration in CHO cell lysate was 1 mM (Ellman's assay).

The supernatant from each sample was added to 50 microliter immobilized-Protein A beads (RepliGen) and rotated at ambient temperature for 2.5 hours, after which the supernatant was removed and the beads washed with PBS. The thiol content of the immobilized antibody was determined by the addition of 0.6 ml of PBS containing 0.5 mM DTNB (Ellman's reagent) to the beads, rotation for about 10 minutes, centrifugation, and absorbance measurement of the supernatant at 412 nm. The control, antibody sample (without any GSSG or glutathione reductase added) showed 5.63 thiol/antibody generated by reduction of antibody disulfide by CHO lysate.

Figure 18:
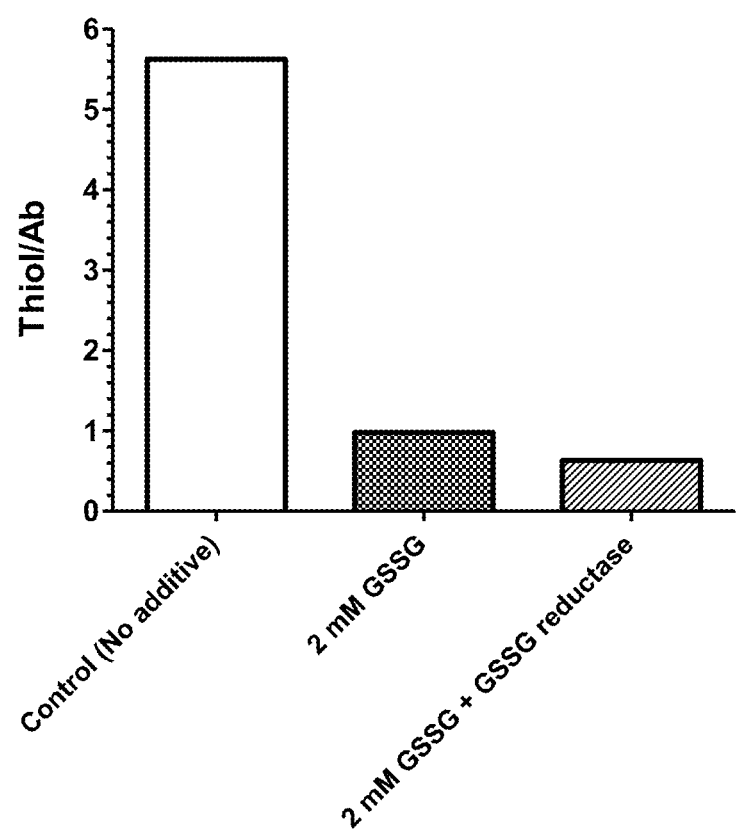
FIG. 18 is a graph that shows the effect of a combination of glutathione reductase and oxidized glutathione (GSSG), which protects against reduction of disulfide bonds in antibody by CHO cell lysate.

As shown in FIG. 18, treatment with GSSG alone decreased antibody-disulfide reduction by CHO lysate, resulting in 0.98 thiol/antibody. The combination of GSSG and glutathione reductase lowered the thiol/antibody ratio further to 0.63. The combination of GSSG and glutathione reductase, therefore, was even more effective than GSSG alone in decreasing the reduction of antibody disulfide bonds induced by CHO cell lysate.

Example 8: Disulfiram Decreased Antibody Reduction

Humanized N901 IgG1 (1 mg) was immobilized on 0.05 ml of Protein A bead (RepliGen) and treated with pre-mixed 0.45 ml PBS and 0.05 ml damaged CHO cell supernatant with or without 0.1 mM and 0.2 mM disulfiram (also named as tetraethylthiuram disulfide; added using a stock solution of disulfiram in DMSO). The concentration of total thiol (derived from damaged cells) in this mixture was 0.4 mM.

The samples were rotated for about 2.5 hours at ambient temperature, then centrifuged to pellet beads, following which the supernatants were removed and the beads washed with PBS four times. The thiol content of the immobilized antibody on the beads was then analyzed by the addition of 0.6 ml PBS containing 0.5 mM DTNB to the beads, rotation for about 30 minutes, centrifugation, and measurement of the absorbance of the supernatant at 412 nm.

Figure 19:
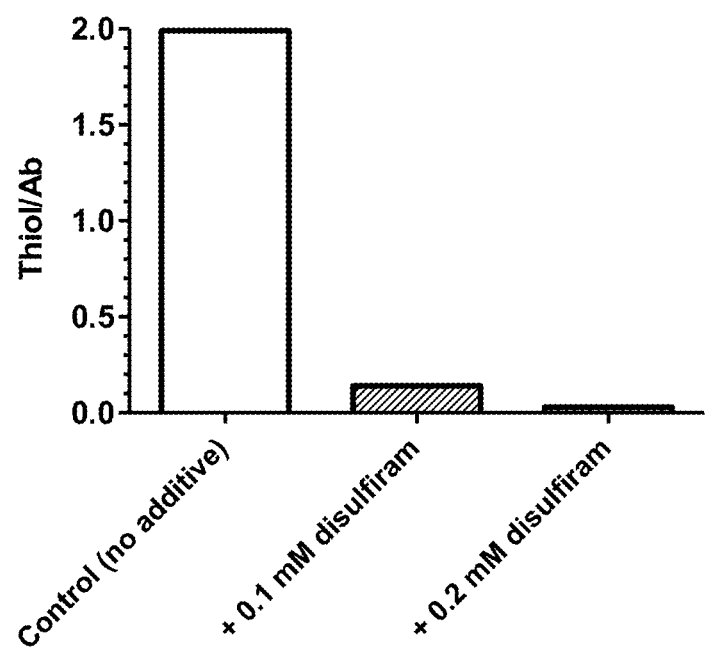
FIG. 19 is a graph that shows the effect of disulfiram, which protects against the reduction of disulfide bonds in antibody by damaged CHO cell supernatant.

In the control antibody sample without disulfiram, the number of thiol residues per antibody molecule after incubation with damaged CHO cell supernatant was calculated as 1.99. For the 0.1 mM and 0.2 mM disulfiram-treated mixtures of antibody and damaged CHO cell supernatant, the thiol/antibody ratios were 0.14 and 0.03, respectively (FIG. 19).

The effective concentrations of disulfiram (0.1 and 0.2 mM) that decreased antibody-disulfide reduction induced by damaged CHO cell supernatant were unexpectedly lower than the total thiol concentration of damaged CHO cell supernatant.

Example 9: Sparging with $O_2$ to Obtain Optimal Culturing Concentrations

The purpose of this experiment is to investigate antibody disulfide reduction in centrifuge-harvested cell culture fluid (HCCF) when the cell culture fluid is maintained at different levels of dissolved oxygen (DO) ranging from 0% to 150% air saturation. These levels of dissolved oxygen are achieved by sparging the harvested cell culture fluid with a mixture of nitrogen and oxygen gas. For each condition, 1 L of continuously centrifuged HCCF is held in a 5 L bioreactor at ambient temperature with moderate agitation (100 rpm), and a constant flow rate of nitrogen of 100 ml/min, and a dissolved oxygen set point of 0%, 50%, 100%, or 150% air saturation, which is controlled by the addition of oxygen gas. Samples are drawn periodically and analyzed for antibody disulfide reduction using a Non-Reduced GelChip.

Figure 20:
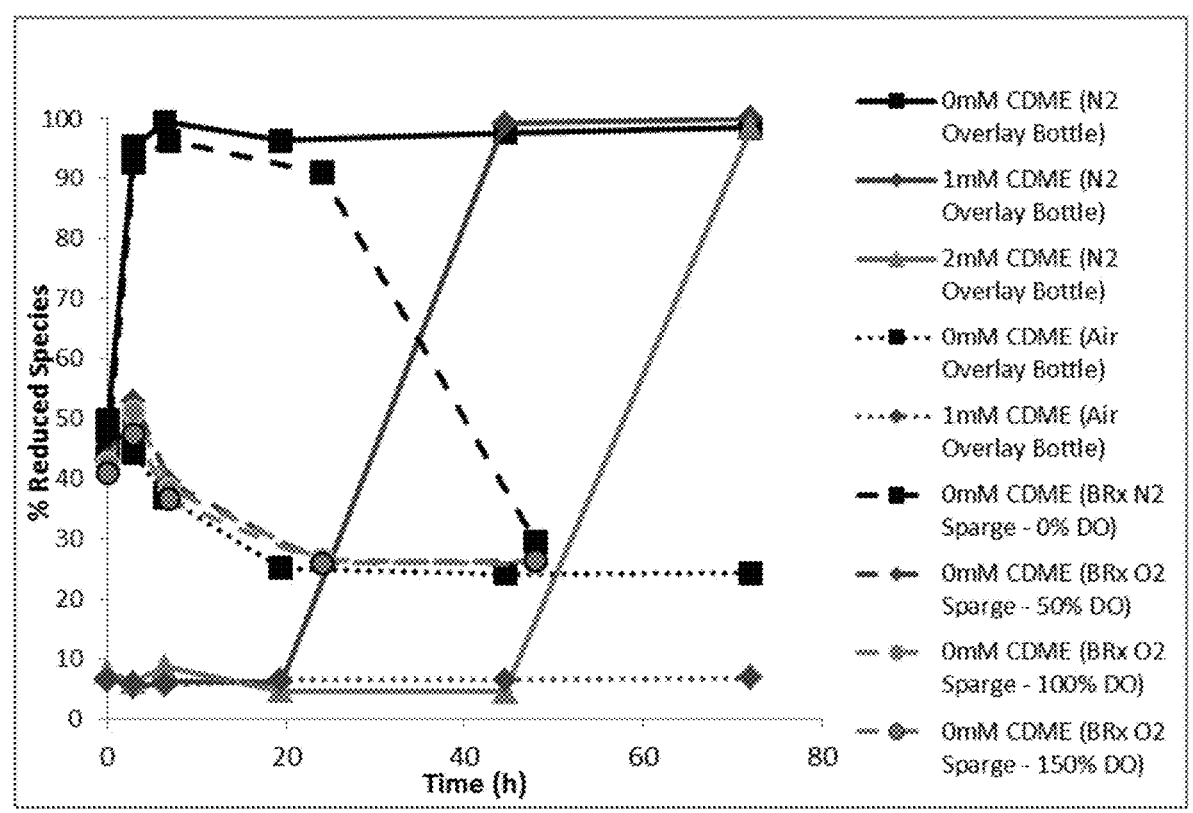
FIG. 20 is a graph that shows the disulfide-protective effect of various combinations of L-cystine dimethyl ester (CDME) with air, oxygen, and nitrogen.

Example 10: Protection of Reduction of Disulfide Bonds in Antibody Using Combinations of Air and CDME A CHO cell culture producing recombinant humanized IgG1 antibody was subjected to centrifugation and the resulting harvest cell culture fluid (HCCF) was frozen at −80° C. After thaw, samples were prepared, which were kept under nitrogen, or air, or with combinations of air and CDME (1 mM), or with combinations of nitrogen and CDME (1 mM, or 2 mM). At various time points, samples were quenched with N-ethylmaleimide (NEM), purified using immobilized Protein A, and analyzed for fragments using non-reducing SDS-Protein Lab Chip electrophoresis. FIG. 20 shows that the control sample kept under nitrogen, which was initially about 48% fragmented, became nearly completely fragmented (99.4%) within 6.5 hours and stayed reduced. In contrast, the sample overlayed with air became less fragmented with time, reaching a plateau of about 25% fragmentation at 20 hours. Additionally, sparging with oxygen at various percentages of dissolved $O_2$ showed protection against fragmentation whereas samples kept under nitrogen alone had no protection against fragmentation. The protection against disulfide reduction is enhanced by the combination of air overlay with CDME (even at low concentration of ~1 mM), which lowered the fragmentation further throughout the course of the study, up to 72 hours. Based on the levels of protection seen with air overlay alone and with oxygen sparging, the combination of oxygen sparging with CDME is also expected to be highly effective against antibody disulfide bond reduction. The combinations of CDME and nitrogen, were slightly less protective than those with CDME and air; the combinations of 1 mM and 2 mM CDME with nitrogen protected the antibody from reduction up to 20 hours, and 45 hours, respectively. Overall, the fragmentation with air and CDME together were significantly less than with nitrogen and CDME together. Therefore, CDME alone or a combination of oxygen sparging or air overlay with CDME is especially protective of the reduction of disulfide bonds of an antibody.

Figure 21:
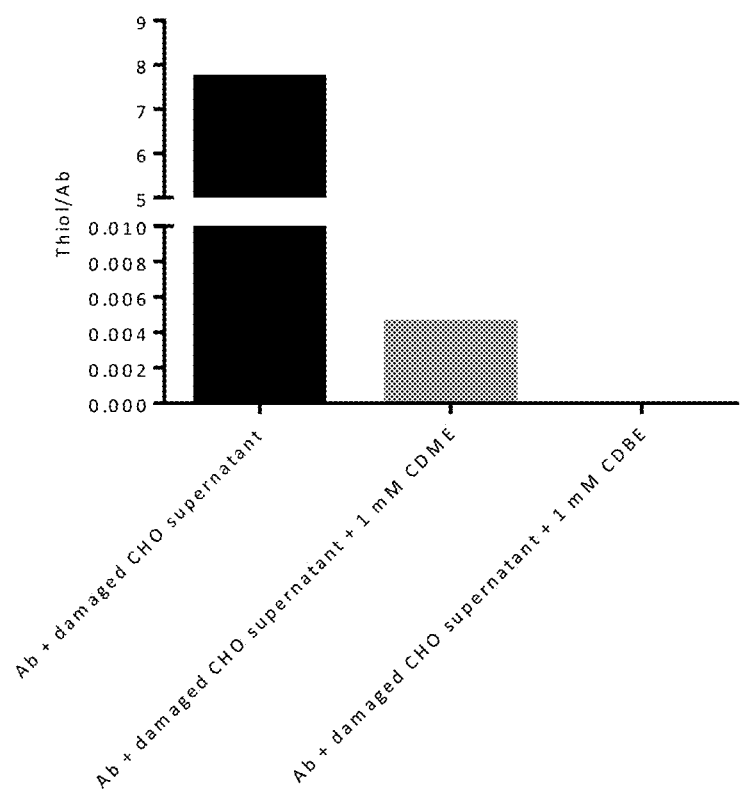
FIG. 21 is a graph that shows the disulfide-protective effect of 1 mM CDME or 1 mM CDBE treatment on a humanized IgG4 antibody.

Example 11: Protection of Reduction of Disulfide Bonds of Humanized IgG4 Antibody A solution of humanized IgG4 in PBS (0.5 mg/ml; final concentration) was incubated with 30% v/v CHO cell lysate (~60 million cells lysed in 0.6 ml RIPA buffer and clarified by centrifugation) with or without 1 mM CDME in a total volume of 2 ml. All samples were adjusted to pH 7 and incubated with 200 µl protein A beads for 4 hours while rotating at room temperature. After the incubation the supernatant was removed and beads washed three times with 10 ml PBS. To analyze the thiol content of the protein A-bound IgG4 antibody, the beads were incubated with a 0.5 mM DTNB solution for 5 min and the absorbance of the supernatant measured at 412 nm. As shown in FIG. 21, the control sample showed reduction of disulfide bonds to an extent of 7.7 thiol groups per antibody. In the sample incubated with 1 mM CDME, the extent of reduction was much lower, resulting in only 0.004 thiol groups per antibody. For the antibody incubated with 1 mM CDBE, the absorbance measured was zero; and thus no reduced disulfides were detected in these samples. Therefore, CDME and CDBE were efficient in protecting the disulfide bonds of an IgG4 antibody from reduction by lysed CHO cells.

Figure 22:
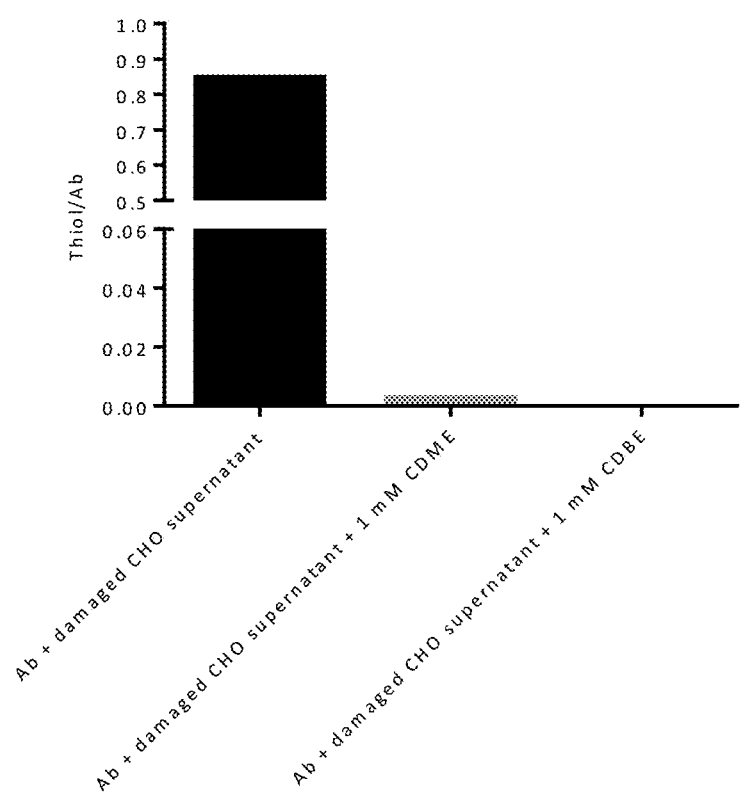
FIG. 22 is a graph that shows the disulfide-protective effect of 1 mM CDME or 1 mM CDBE treatment on a humanized IgG2 antibody.

Example 12: Protection of Reduction of Disulfide Bonds of Humanized IgG2 Antibody Humanized IgG2 antibody (1 mg/ml; final concentration) was incubated with 40% v/v CHO cell lysate (~40 million cells lysed with 0.4 ml RIPA buffer and debris removed by centrifugation) in a total volume of 1 ml. The control sample was adjusted to pH 7 and rotated at RT for 5 hours with 100 µl protein A beads. Additionally, IgG2 antibody was treated as described for the control and contained either 1 mM CDME or 1 mM CDBE. After the incubation time of 5 hours, the supernatant was removed and the beads were washed three times with 10 ml PBS before the thiol amount of the immobilized antibody was analyzed by adding 0.5 mM DTNB and measuring the absorbance at 412 nm. The control sample showed 0.84 reduced thiols per antibody and samples incubated with 1 mM CDME or 1 mM CDBE showed near-zero reduction as shown in FIG. 22. Therefore, CDME and CDBE were efficient in protecting the disulfide bonds of IgG2 antibody from reduction by lysed CHO cells.

Figure 23:
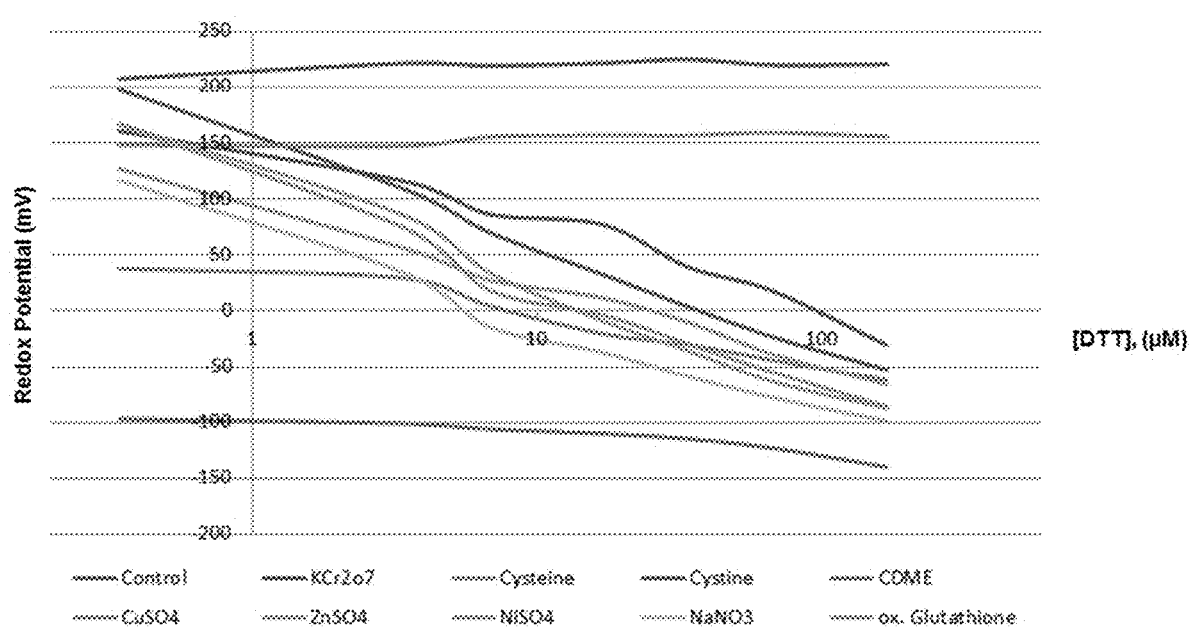
FIG. 23 is a graph that shows the effect of various additives on redox potential over a range of concentration of DTT.

Example 13: Protection of Reduction of Disulfide Bonds of Humanized IgG2 Antibody by Using Zinc, Nitrate, Nickel, and Other Transition Elements Purified M9346A antibody was adjusted to 5 mg/mL final concentration in formulation buffer (25 mM histidine, 10% sucrose, 0.01% polysorbate-20, pH 6.3) with or without addition of 1 mM of a given media additive, and increasing amounts of DTT were added. DTT concentration ranged from 0.34 µM to 3.4 µM to 6.8 µM to 17 µM to 34 to 68 µM to 170 µM. The corresponding ratio of the M9346A antibody (at 5 mg/mL) to DTT ranged from 100 to 10 to 5 to 2 to 1 to 0.5 to 0.2. The mixtures were incubated in a water bath at 37° C. for 1 h. Redox potential was measured using a redox probe. Free thiols were alkylated by addition of 10% (v/v) of 50 mM N-ethyl-maleimide (NEM) solution. Samples were analyzed by non-reduced sodium dodecyl sulfate denaturing capillary electrophoresis (NR-CE-SDS). As expected, control conditions without media additives showed a linear decline in redox potential when plotted against DTT concentration on a logarithmic scale (FIG. 23, blue curve). Addition of several additives led to modulation of the redox potential: several compounds, both organic and inorganic, showed constant redox potential across all DTT concentrations (examples include CDME, dichromate, and copper).

Other substances modulated the redox potential in variable ways. Addition of cysteine led to constant redox potential at low concentrations of DTT, followed by a slow decrease at higher DTT concentrations (FIG. 23, dark green curve). Other additives led to step-wise modulation of redox potential, e.g. cystine.

When analyzing these samples for quantification of reduced species, we found that numerous components protected antibodies from disulfide reduction over a wide span of DTT concentrations.

Figure 24:
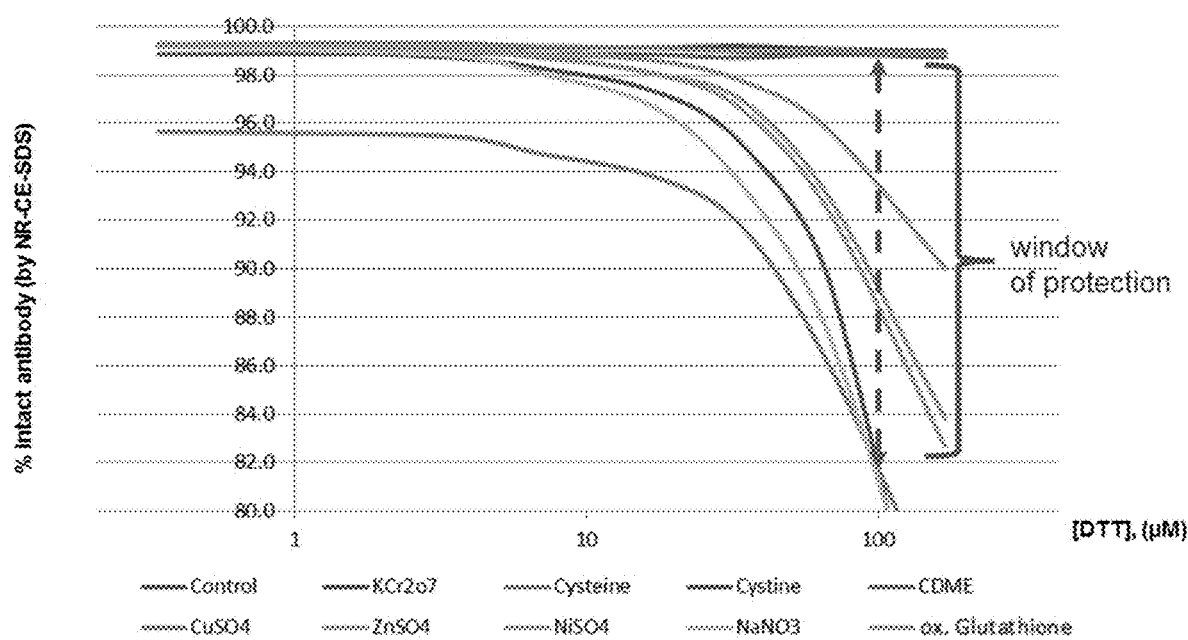
FIG. 24 is a graph that shows the effect of various additives on percent of intact antibody over a range of concentration of DTT.
Figure 25:
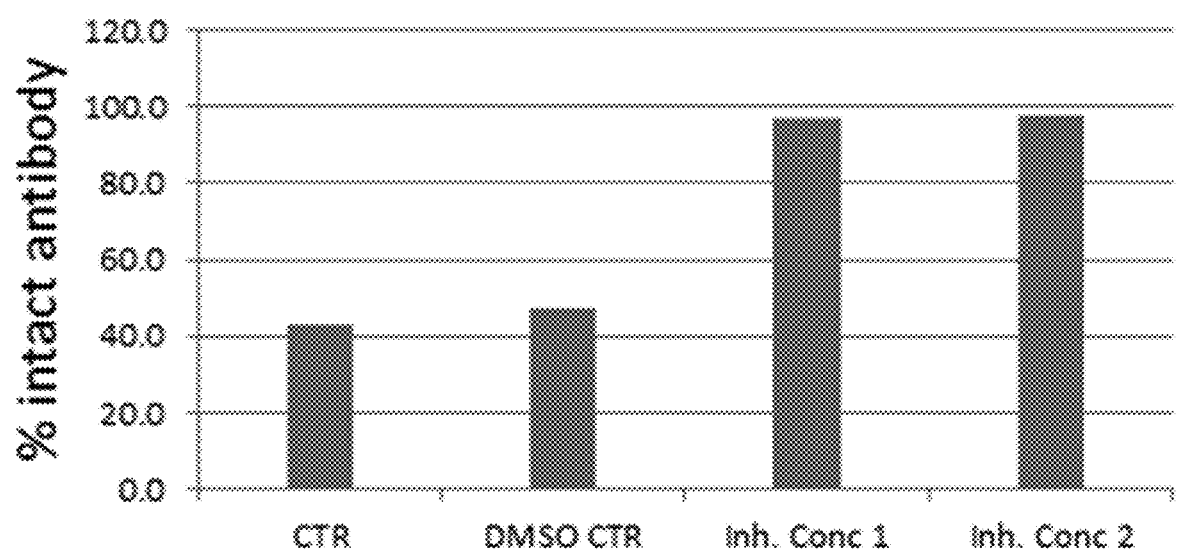
FIG. 25 is a graph that shows the percent intact antibody obtained when Thioredoxin Reductase is inhibited.

At 100 µM DTT, 80% of offered mAb remained intact in control condition (FIG. 24, blue curve). Numerous additives showed greater percentages of intact antibody under the same conditions, spanning a window from 80-100% intact antibody. For example, addition of 1 mM nickel sulfate yielded ~90% intact antibody, and 1 mM copper sulfate,

Example 14: Protection of Reduction of Disulfide Bonds of Humanized IgG2 Antibody Antibody reduction was induced in a biological assay by adding cell lysate to purified monoclonal antibody. Purified M9346A antibody was adjusted to 5 mg/mL final concentration in lysis buffer A (25 mM Tris, 150 mM NaCl, 0.1% Tween-20, Complete® protease inhibitor cocktail, pH 7.5) with or without addition of 1 mM of a given media additive. Increasing amounts of CHO cell lysate were added to mimic different percentages of cell lysis, ranging from 30-180%. Fresh NADPH was added to a concentration of 400 µM. The mixtures were incubated in a water bath at 37° C. for 1 h. Free thiols were alkylated by addition of 10% (v/v) of 50 mM N-ethyl-maleimide (NEM) solution. Samples were analyzed by non-reduced sodium dodecyl sulfate denaturing capillary electrophoresis (NR-CE-SDS). It was consistently found that 40% intact antibody was left after incubation with cell lysate to mimic 120% cell lysis (FIG. 25, control condition). Addition of a specific inhibitor of thioredoxin reductase at two different concentrations revealed that antibody fragmentation is mediated by Thioredoxin Reductase, as nearly 100% intact antibody was recovered after addition of inhibitor, but not solvent alone (FIG. 25, DMSO control).

Figure 26:
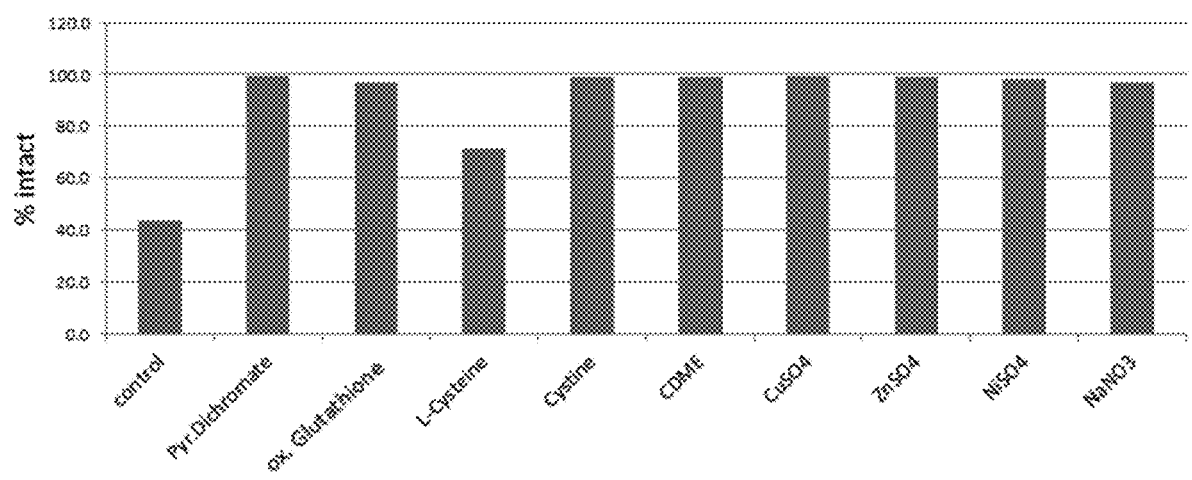
FIG. 26 is a graph showing the results of a biological assay using various additives to protect M9346A from disulfide reduction.

Using this assay, media additives were tested at 1 mM each. All of them protected M9346A from disulfide reduction (FIG. 26). Eight of nine tested compounds protected M9346A nearly completely, only cysteine showed partial protection, with ~70% of intact antibody.

Figure 27:
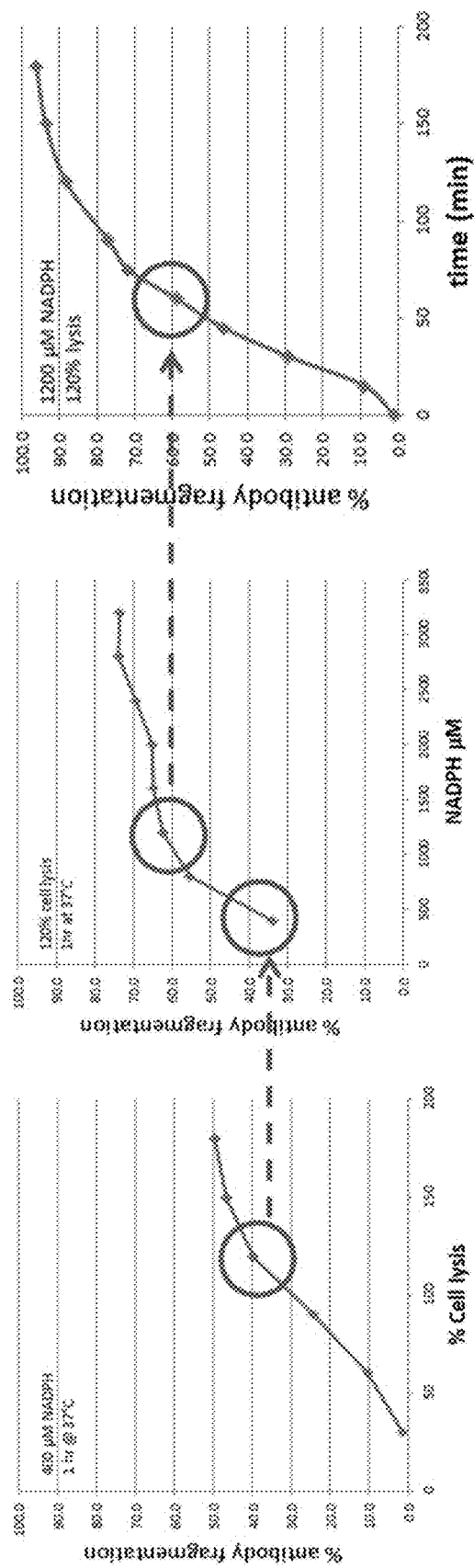
FIG. 27 is a series of graphs showing the data that resulted from a biological assay with varying stringency parameters.

To test the capacity for protection further, the stringency of the assay was increased. Antibody fragmentation began to saturate at lysate concentrations mimicking greater than 120% cell lysis (FIG. 27, left panel). Therefore, the modeled percentage of lysis was kept constant at 120% and increased the concentration of available NADPH, ranging from 400 µM to 3200 µM (FIG. 27, middle panel). Antibody fragmentation steeply increased through concentrations ranging from 400 µM to 1200 µM, but plateaued beyond 1200 µM. Therefore, NADPH concentrations were kept constant at 1200 µM and incubation time was increased from 1 h to 3 h (FIG. 27, right panel).

Figure 28:
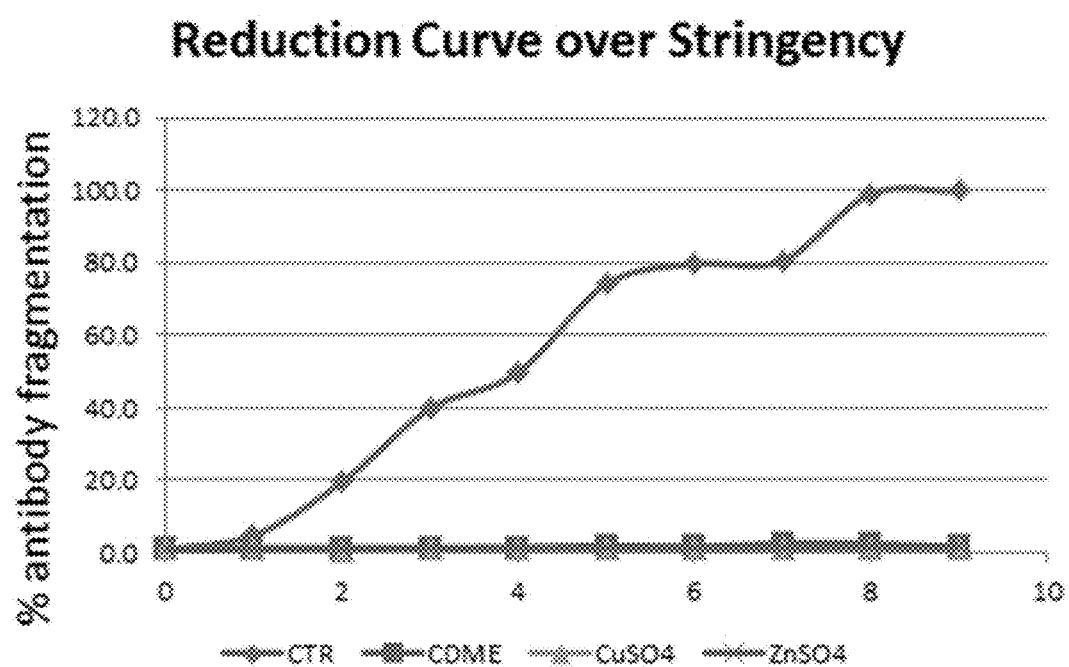
FIG. 28 is a graph showing the results of a stringency evaluation of various media additives.

Increasing assay stringency was achieved by modulating percentage of modeled cell lysis, NADPH concentration, and incubation time (stringency levels 0-9), and multiple levels of antibody fragmentation were generated, covering the entire range from fully intact antibody to completely reduced antibody (FIG. 28, blue curve).

We found that 1 mM CDME, copper, or zinc were protective of disulfide reduction, even at conditions where the control without any additive was 100% fragmented (FIG. 28).

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

---

What is claimed is:

1. A method of inhibiting disulfide bond reduction in a recombinant antibody expressed in a host cell, the method comprising adding an anti-reduction agent to a final concentration of 1 mM to a cell culture media, pre-harvest cell culture fluid, or harvest cell culture fluid comprising the antibody, wherein the anti-reduction agent is selected from the group consisting of $ZnSO_4$, $CuSO_4$, $NiSO_4$, and $NaNO_3$.

2. A method of increasing production of antibody with intact native disulfide bonds that is expressed in a mammalian host cell, the method comprising adding an anti-reduction agent to a final concentration of 1 mM to a cell culture media, pre-harvest cell culture fluid, or harvest cell culture fluid comprising the antibody, wherein the anti-reduction agent is selected from the group consisting of $ZnSO_4$, $CuSO_4$, $NiSO_4$, and $NaNO_3$.

3. The method of claim 2, wherein greater than about 80% of the antibody produced has intact native disulfide bonds.

4. The method of claim 3, wherein greater than about 90% of the antibody produced has intact native disulfide bonds.

5. The method of claim 1, wherein the method comprises adding the anti-reduction agent to the cell culture media.

6. The method of claim 5, wherein the method comprises adding the anti-reduction agent to the cell culture medium within about 48 hours of harvesting the cell culture.

7. The method of claim 5, wherein the method comprises adding the anti-reduction agent to the cell culture medium within about 24 hours of harvesting the cell culture.

8. The method of claim 5, wherein the method comprises adding the anti-reduction agent to the cell culture medium within about 12 hours of harvesting the cell culture.

9. The method of claim 5, wherein the method comprises adding the anti-reduction agent to the cell culture medium within about 15 minutes of harvesting the cell culture.

10. The method of claim 1, wherein the method comprises adding the anti-reduction agent to the pre-harvest cell culture fluid.

11. The method of claim 1, wherein the method comprises adding the anti-reduction agent to the harvest cell culture fluid.

12. The method of claim 1, wherein the host cell is a Chinese Hamster Ovary (CHO) cell.

13. The method of claim 1, wherein the antibody is selected from an anti-folate receptor 1 ("anti-FOLR1") antibody, an anti-CD56 antibody, an anti-CD37 antibody, an anti-EGFR antibody, an anti-IGF-1R antibody, an anti-MUC1, an anti-CA6 glycotope, an anti-CD19 antibody, and an anti-CD33 antibody.

14. The method of claim 13, wherein the anti-FOLR1 antibody comprises a heavy chain represented by SEQ ID NO:3 and a light chain variable region sequence represented by SEQ ID NO.: 4 or 5.

15. The method of claim 13, wherein the anti-FOLR1 antibody is huMov19.

16. The method of claim 13, wherein the anti-CD56 antibody is huN901.

17. The method of claim 1, wherein the antibody is an antigen binding fragment of an antibody.

18. The method of claim 2, wherein the antibody is an antigen binding fragment of an antibody.

19. A method of inhibiting disulfide bond reduction in a recombinant antibody expressed in a host cell, the method comprising adding an anti-reduction agent to a final concentration in a range from about 1 mM to about 10 mM to a cell culture media, pre-harvest cell culture fluid, or harvest cell culture fluid comprising the antibody, wherein the anti-reduction agent is selected from the group consisting of $ZnSO_4$, $NiSO_4$ and $NaNO_3$.

* * * * *